United States Patent
Crescenzi et al.

(10) Patent No.: US 7,968,553 B2
(45) Date of Patent: Jun. 28, 2011

(54) TETRAHYDRO-4H-PYRIDO[1,2-A] PYRIMIDINES USEFUL AS HIV INTEGRASE INHIBITORS

(75) Inventors: Benedetta Crescenzi, Rome (IT); Olaf Kinzel, Rome (IT); Ester Muraglia, Rome (IT); Federica Orvieto, Rome (IT); Giovanna Pescatore, Cosenza (IT); Michael Rowley, Axa (IT); Vincenzo Summa, Velletri (IT)

(73) Assignee: Istituto Di Ricerche Di Biologia Molecolare P. Angeletti S.p.A., Rome (IT)

(*) Notice: Subject to any disclaimer, the term of this patent is extended or adjusted under 35 U.S.C. 154(b) by 726 days.

(21) Appl. No.: 12/075,514

(22) Filed: Mar. 12, 2008

(65) Prior Publication Data

US 2008/0176869 A1      Jul. 24, 2008

Related U.S. Application Data

(62) Division of application No. 10/540,449, filed as application No. PCT/GB03/05536 on Dec. 18, 2003, now Pat. No. 7,414,045.

(60) Provisional application No. 60/436,830, filed on Dec. 27, 2002, provisional application No. 60/528,776, filed on Dec. 12, 2003.

(51) Int. Cl.
A61K 31/517      (2006.01)
C07D 487/04      (2006.01)
A61K 31/519      (2006.01)
C07D 239/70      (2006.01)

(52) U.S. Cl. ............ 514/259.4; 540/579; 540/476; 514/259.41; 514/214.02; 544/282

(58) Field of Classification Search ............ 544/282; 514/259.4
See application file for complete search history.

(56) References Cited

U.S. PATENT DOCUMENTS

| | | |
|---|---|---|
| 6,262,055 B1 | 7/2001 | Young et al. |
| 6,306,891 B1 | 10/2001 | Selnick et al. |
| 6,380,249 B1 | 4/2002 | Young et al. |
| 7,169,780 B2 | 1/2007 | Crescenzi et al. |
| 2003/0055071 A1 | 3/2003 | Anthony et al. |
| 2004/0106627 A1 | 6/2004 | Gardelli et al. |
| 2004/0110804 A1 | 6/2004 | Walker et al. |
| 2004/0204498 A1 | 10/2004 | Walker et al. |
| 2004/0229892 A1 | 11/2004 | Naidu et al. |
| 2004/0229909 A1 | 11/2004 | Kiyama et al. |
| 2005/0025774 A1 | 2/2005 | Crescenzi et al. |
| 2005/0075356 A1 | 4/2005 | DiFrancesco et al. |
| 2005/0119482 A1 | 6/2005 | Egbertson et al. |
| 2006/0258860 A1 | 11/2006 | Crescenzi et al. |

FOREIGN PATENT DOCUMENTS

| | | |
|---|---|---|
| WO | WO 01/00578 A1 | 1/2001 |
| WO | WO 01/94351 A1 | 12/2001 |
| WO | WO 02/06246 A1 | 1/2002 |
| WO | WO 02/30426 A1 | 4/2002 |
| WO | WO 02/30930 A2 | 4/2002 |
| WO | WO 02/36734 A2 | 5/2002 |
| WO | WO 02/055079 A2 | 7/2002 |
| WO | WO 03/016275 A1 | 2/2003 |
| WO | WO 03/035076 A1 | 5/2003 |
| WO | WO 03/035077 A1 | 5/2003 |
| WO | WO 03/062204 A1 | 7/2003 |

OTHER PUBLICATIONS

Ratner, L., et al., "Complete Nucleotide Sequence of the AIDS Virus, HTLV-III", Nature, vol. 313, pp. 277-284, (1985).

Toh, H., et al., "Close Structural Resemblance Between Putative Polymerase of a Drosphila Transposable Genetic Element 17.6 and Pol Gene Product of Moloney Murine Leukemia Virus", EMBO Journal, vol. 4, No. 5, pp. 1267-1272, (1985).

Power, M.D., et al., "Nucleotide Sequence of SRV-1, a Type D Simian Acquired Immune Deficiency Syndrome Retrovirus", Science, vol. 231, pp. 1567-1572, (1986).

Pearl, L.H., et al., "A Structural Model for the Retroviral Proteases", Nature, vol. 329, pp. 351-354, (1987).

*Primary Examiner* — Susanna Moore
(74) *Attorney, Agent, or Firm* — Kenneth R. Walton

(57) ABSTRACT

Tetrahydro-4H-pyrido[1,2-a]pyrimidines and related compounds of Formula A:

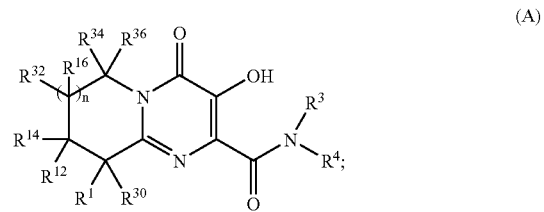

(A)

are described as inhibitors of HIV integrase and inhibitors of HIV replication, wherein n is an integer equal to zero, 1, 2 or 3, and $R^1$, $R^3$, $R^4$, $R^{12}$, $R^{14}$, $R^{16}$, $R^{30}$, $R^{32}$, $R^{34}$ and $R^{36}$ are defined herein. These compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines.

14 Claims, No Drawings

TETRAHYDRO-4H-PYRIDO[1,2-A] PYRIMIDINES USEFUL AS HIV INTEGRASE INHIBITORS

This application is a divisional application of U.S. application Ser. No. 10/540,449, U.S. Pat. No. 7,414,045 filed Jun. 22, 2005, which is the National Stage of International Application No. PCT/GB2003/005536, filed Dec. 18, 2003, which claims the benefit of U.S. Provisional Application No. 60/436,830 (filed Dec. 27, 2002) and U.S. Provisional Application No. 60/528,776 (filed Dec. 12, 2003).

FIELD OF THE INVENTION

The present invention is directed to tetrahydro-4H-pyrido [1,2-a]pyrimidines, related compounds, and pharmaceutically acceptable salts thereof, their synthesis, and their use as inhibitors of the HIV integrase enzyme. The compounds and pharmaceutically acceptable salts thereof of the present invention are useful for preventing or treating infection by HIV and for treating or delaying the onset of AIDS.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:

U.S. Pat. No. 6,380,249, U.S. Pat. No. 6,306,891, and U.S. Pat. No. 6,262,055 disclose 2,4-dioxobutyric acids and acid esters useful as HIV integrase inhibitors.

WO 01/00578 discloses 1-(aromatic- or heteroaromatic-substituted)-3-(heteroaromatic substituted)-1,3-propanediones useful as HIV integrase inhibitors.

US 2003/0055071 (corresponding to WO 02/30930), WO 02/30426, and WO 02/55079 each disclose certain 8-hydroxy-1,6-naphthyridine-7-carboxamides as HIV integrase inhibitors.

WO 02/036734 discloses certain aza- and polyaza-naphthalenyl ketones to be HIV integrase inhibitors.

WO 03/016275 discloses certain compounds having integrase inhibitory activity.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

WO 03/062204 discloses certain hydroxynaphthyridinone carboxamides that are useful as HIV integrase inhibitors.

SUMMARY OF THE INVENTION

The present invention is directed to novel pyridopyrimidine derivatives and related compounds. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts or hydrates (when appropriate), or as pharmaceutical composition ingredients, whether or not in combination with other HIV/AIDS antivirals, anti-infectives, immunomodulators, antibiotics or vaccines. More particularly, the present invention includes compounds of Formula A, and pharmaceutically acceptable salts thereof:

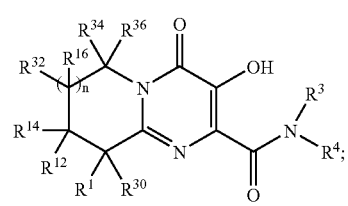

(A)

wherein $R^1$, $R^{12}$, and each $R^{16}$ are independently H, $NR^2R^5$, $OR^2$, $SR^2$, $SOR^2$, $SO_2R^2$, $SO_2NR^2R^5$, $OC(O)NR^2R^5$, $R^{11}$, $C_{1-6}$ alkyl, substituted alkyl, $SR^{18}$, $SO_2R^{18}$, or $N[SO_2N(C_{1-6}$ alkyl)$_2]R^{18}$; wherein substituted alkyl is $C_{1-6}$ alkyl substituted with O—$C_{1-6}$ alkyl, $C_{3-8}$ cycloalkyl, or aryl (e.g., phenyl or naphthyl), wherein the cycloalkyl is optionally substituted with from 1 to 3 $C_{1-6}$ alkyl groups and the aryl is optionally substituted with from 1 to 5 substituents each of which is independently $C_{1-6}$ alkyl, O—$C_{1-6}$ alkyl, $CF_3$, $OCF_3$, halo, CN, or $NO_2$; with the proviso that no more than one of $R^1$, $R^{12}$ and $R^{16}$ is other than H, $C_{1-6}$ alkyl, or substituted alkyl;

$R^2$ is

1) H, or

2) $C_{1-6}$ alkyl which is optionally substituted with aryl, $C_{3-8}$ cycloalkyl, or a 5- or 6-membered heteroaromatic ring containing from 1 to 4 heteroatoms independently selected from N, O and S;

$R^5$ is
1) H,
2) $C_{1-6}$ alkyl, optionally substituted at any carbon atom with halogen, aryl, $SO_2$—$C_{1-6}$ alkyl, $N(C_{1-6}$ alkyl$)_2$, or $SO_2NR^uR^v$, wherein $R^u$ and $R^v$ are each independently a $C_{1-6}$ alkyl group or $R^u$ and $R^v$ together with the N to which they are attached form a 4- to 7-membered saturated heterocyclic ring containing at least one carbon atom and from zero to 3 heteroatoms in addition to the N atom to which $R^u$ and $R^v$ are attached, wherein the additional heteroatoms are independently selected from N, O and S, and in which any ring S atom is optionally oxidized to SO or $SO_2$, and wherein the heterocyclic ring is optionally substituted with from 1 to 3 substituents each of which is independently a $C_{1-6}$ alkyl group,
3) $C(O)C_{1-6}$ alkyl, where the alkyl is optionally substituted at any carbon atom with halogen, aryl, $SO_2$—$C_{1-6}$ alkyl, $N(C_{1-6}$ alkyl$)_2$, or $SO_2NR^{u*}R^{v*}$, wherein $R^{u*}$ and $R^{v*}$ independently have the same definition as $R^u$ and $R^v$ respectively as set forth above,
4) $C(O)$—$C_{1-6}$ fluoroalkyl,
5) $C(O)R^7$,
6) $C(O)C(O)NR^8R^9$,
7) $SO_2NR^8R^9$,
8) $SO_2C_{1-6}$ alkyl, where the alkyl is optionally substituted at any carbon atom with halogen, aryl, $SO_2$—$C_{1-6}$ alkyl or $N(C_{1-6}$ alkyl$)_2$,
9) $C(O)NR^8R^9$,
10) $SO_2R^7$,
11) $C(O)C(O)R^{10}$, where $R^{10}$ is a 4- to 7-membered saturated heterocyclic ring containing at least one carbon atom and from 1 to 4 heteroatoms independently selected from N, O and S, and in which any ring S atom is optionally oxidized to SO or $SO_2$, and wherein the heterocyclic ring is optionally substituted with from 1 to 3 substituents each of which is independently a $C_{1-6}$ alkyl group,
12) $C(O)O$—$C_{1-6}$ alkyl, or
13) $SO_2R^{20}$, wherein $R^{20}$ is a saturated heterocyclic ring independently having the same definition as $R^{10}$ set forth above;

or alternatively $R^2$ and $R^5$ together with the nitrogen atom to which they are attached form a 4- to 7-membered saturated heterocyclic ring containing at least one carbon atom and from zero to 3 heteroatoms in addition to the N atom to which $R^2$ and $R^5$ are attached, wherein the additional heteroatoms are independently selected from N, O and S, and in which any ring S atom is optionally oxidized to SO or $SO_2$, and wherein the heterocyclic ring is optionally substituted with from 1 to 3 substituents each of which is independently a $C_{1-6}$ alkyl group;

$R^7$ and $R^{11}$ are each independently a 5- or 6-membered unsaturated heterocyclic ring or an unsaturated 9- or 10-membered heterobicyclic fused ring system, wherein the ring or bicyclic ring system contains from 1 to 4 heteroatoms independently selected from N, O and S, and in which any one or more of the N and S atoms is optionally oxidized, and wherein the ring is optionally substituted with from 1 to 3 substituents each of which is independently a $C_{1-6}$ alkyl group;

$R^8$ and $R^9$ are each independently selected from the group consisting of $C_{1-6}$ alkyl and aryl;

$R^{14}$, $R^{30}$, each $R^{32}$, $R^{34}$ and $R^{36}$ are independently:
(1) H,
(2) $C_{1-6}$ alkyl or
(3) $C_{1-6}$ alkyl substituted with O—$C_{1-6}$ alkyl, $C_{3-8}$ cycloalkyl, or aryl, wherein the cycloalkyl is optionally substituted with from 1 to 3 $C_{1-6}$ alkyl groups and the aryl is optionally substituted with from 1 to 5 substituents each of which is independently $C_{1-6}$ alkyl, O—$C_{1-6}$ alkyl, $CF_3$, $OCF_3$, halo, CN, or $NO_2$;

$R^{18}$ is $C_{1-6}$ alkyl substituted with $C(O)NR^wR^x$, wherein $R^w$ and $R^x$ are each independently a $C_{1-6}$ alkyl group or $R^w$ and $R^x$ together with the N to which they are attached form a 4- to 7-membered saturated heterocyclic ring containing at least one carbon atom and from zero to 3 heteroatoms in addition to the N atom to which $R^w$ and $R^x$ are attached, wherein the additional heteroatoms are independently selected from N, O and S, and wherein any of the ring S atoms is optionally oxidized to SO or $SO_2$, and wherein the saturated heterocyclic ring is optionally substituted with from 1 to 3 substituents each of which is independently a $C_{1-6}$ alkyl group;

$R^3$ is H or $C_{1-6}$ alkyl;

$R^4$ is
1) hydrogen,
2) $C_{1-6}$ alkyl which is optionally substituted with one or more substituents (e.g., optionally from 1 to 6, or 1 to 5, or 1 to 4, or 1 to 3, or 1 or 2 substituents; or is optionally mono-substituted) each of which is independently halogen, OH, O—$C_{1-6}$ alkyl, O—$C_{1-6}$ haloalkyl, $NO_2$, $N(R^aR^b)$, $C(O)R^a$, $CO_2R^a$, $SR^a$, $S(O)R^a$, $SO_2R^a$, or $N(R^a)CO_2R^b$,
3) $C_{1-6}$ alkyl which is optionally substituted with one or more substituents (e.g., optionally from 1 to 6, or 1 to 5, or 1 to 4, or 1 to 3, or 1 or 2 substituents; or is optionally mono-substituted) each of which is independently halogen, OH, or O—$C_{1-4}$ alkyl, and which is substituted with 1 or 2 substituents each of which is independently:
 i) $C_{3-8}$ cycloalkyl,
 ii) aryl,
 iii) a fused bicyclic carbocycle consisting of a benzene ring fused to a $C_{5-7}$ cycloalkyl,
 iv) a 5- or 6-membered saturated heterocyclic ring containing from 1 to 4 heteroatoms independently selected from N, O and S,
 v) a 5- or 6-membered heteroaromatic ring containing from 1 to 4 heteroatoms independently selected from N, O and S, or
 vi) a 9- or 10-membered fused bicyclic heterocycle containing from 1 to 4 heteroatoms independently selected from N, O and S, wherein at least one of the rings is aromatic,
4) $C_{2-5}$ alkynyl optionally substituted with aryl,
5) $C_{3-8}$ cycloalkyl optionally substituted with aryl,
6) aryl,
7) a fused bicyclic carbocycle consisting of a benzene ring fused to a $C_{5-7}$ cycloalkyl,
8) a 5- or 6-membered saturated heterocyclic ring containing from 1 to 4 heteroatoms independently selected from N, O and S,
9) a 5- or 6-membered heteroaromatic ring containing from 1 to 4 heteroatoms independently selected from N, O and S, or
10) a 9- or 10-membered fused bicyclic heterocycle containing from 1 to 4 heteroatoms independently selected from N, O and S, wherein at least one of the rings is aromatic;

wherein
each aryl in (3)(ii) or the aryl (4), (5) or (6) or each fused carbocycle in (3)(iii) or the fused carbocycle in (7) is optionally substituted with one or more substituents (e.g., optionally from 1 to 6, or 1 to 5, or 1 to 4, or 1 to 3, or 1 or 2 substituents; or is optionally mono-substituted) each of which is independently halogen, OH, $C_{1-6}$ alkyl, —$C_{1-6}$ alkylene-OR$^a$, $C_{1-6}$ haloalkyl, O—$C_{1-6}$ alkyl, O—$C_{1-6}$ haloalkyl, CN, NO$_2$, N(R$^a$R$^b$), —$C_{1-6}$ alkylene-N(R$^a$R$^b$), C(O)N(R$^a$R$^b$), C(O)R$^a$, CO$_2$R$^a$, —$C_{1-6}$ alkylene-CO$_2$R$^a$, OCO$_2$R$^a$, SR$^a$, S(O)R$^a$, SO$_2$R$^a$, N(R$^a$)SO$_2$R$^b$, SO$_2$N(R$^a$R$^b$), N(R$^a$)C(O)R$^b$, N(R$^a$)CO$_2$R$^b$, —$C_{1-6}$ alkylene-N(R$^a$)CO$_2$R$^b$, aryl, —$C_{1-6}$ alkylene-aryl, O-aryl, or —$C_{0-6}$ alkylene-HetA wherein HetA is a 5- or 6-membered heteroaromatic ring containing from 1 to 4 heteroatoms independently selected from N, O and S, and the heteroaromatic ring is optionally fused with a benzene ring, and is optionally substituted with one or more substituents (e.g., optionally from 1 to 6, or 1 to 5, or 1 to 4, or 1 to 3, or 1 or 2 substituents; or is optionally mono-substituted) each of which is independently $C_{1-6}$ alkyl, $C_{1-6}$ haloalkyl, O—$C_{1-6}$ alkyl, O—$C_{1-6}$ haloalkyl, oxo, or CO$_2$R$^a$;

each saturated heterocyclic ring in (3)(iv) or the saturated heterocyclic ring in (8) is optionally substituted with one or more substituents (e.g., optionally from 1 to 6, or 1 to 5, or 1 to 4, or 1 to 3, or 1 or 2 substituents; or is optionally mono-substituted) each of which is independently halogen, $C_{1-6}$ alkyl, $C_{1-6}$ haloalkyl, O—$C_{1-6}$ alkyl, O—$C_{1-6}$ haloalkyl, oxo, aryl, or a 5- or 6-membered heteroaromatic ring containing from 1 to 4 heteroatoms independently selected from N, O and S; and each heteroaromatic ring in (3)(v) or the heteroaromatic ring in (9) or each fused bicyclic heterocycle in (3)(vi) or the fused bicyclic heterocycle in (10) is optionally substituted with one or more substituents (e.g., optionally from 1 to 6, or 1 to 5, or 1 to 4, or 1 to 3, or 1 or 2 substituents; or is optionally mono-substituted) each of which is independently halogen, $C_{1-6}$ alkyl, $C_{1-6}$ haloalkyl, O—$C_{1-6}$ alkyl, O—$C_{1-6}$ haloalkyl, oxo, aryl, or $C_{1-6}$ alkylene-aryl;

or alternatively R$^3$ and R$^4$ together with the nitrogen to which both are attached form a $C_{3-7}$ azacycloalkyl which is optionally substituted with one or more substituents (e.g., optionally from 1 to 6, or 1 to 5, or 1 to 4, or 1 to 3, or 1 or 2 substituents; or is optionally mono-substituted) each of which is independently $C_{1-6}$ alkyl or oxo;

each R$^a$ and R$^b$ is independently hydrogen or $C_{1-6}$ alkyl; and n is an integer equal to zero, 1, 2, or 3.

The present invention also includes compounds of Formula I, and pharmaceutically acceptable salts thereof:

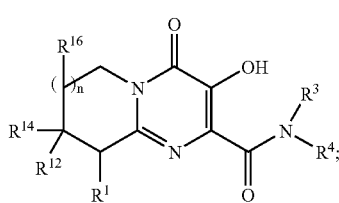

(I)

wherein R$^1$, R$^{12}$, and each R$^{16}$ are independently H, NR$^2$R$^5$, OR$^2$, SR$^2$, SOR$^2$, SO$_2$R$^2$, SO$_2$NR$^2$R$^5$, OC(O)NR$^2$R$^5$, R$^{11}$, $C_{1-6}$ alkyl, SR$^{18}$, SO$_2$R$^{18}$, or N[SO$_2$N($C_{1-6}$ alkyl)$_2$]R$^{18}$; with the proviso that no more than one of R$^1$, R$^{12}$ and R$^{16}$ is other than H or $C_{1-6}$ alkyl;

R$^{14}$ is H or $C_{1-6}$ alkyl; and all other variables are as defined above in Formula A.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes compounds of Formula A and Formula I above, and pharmaceutically acceptable salts thereof. These compounds and pharmaceutically acceptable salts thereof are HIV integrase inhibitors.

A first embodiment of the present invention is a compound of Formula I, or a pharmaceutically acceptable salt thereof, wherein R$^1$, R$^{12}$, and each R$^{16}$ are independently H, NR$^2$R$^5$, OR$^2$, SR$^2$, SOR$^2$, SO$_2$R$^2$, SO$_2$NR$^2$R$^5$, OC(O)NR$^2$R$^5$, R$^{11}$, CH$_3$, SR$^{18}$, SO$_2$R$^{18}$, or N[SO$_2$N($C_{1-3}$ alkyl)$_2$]R$^{18}$; with the proviso that no more than one of R$^1$, R$^{12}$ and R$^{16}$ is other than H or CH$_3$; and all other variables are as originally defined for Formula I.

A second embodiment of the present invention is a compound of Formula I, or a pharmaceutically acceptable salt thereof, wherein R$^1$ is H, NR$^2$R$^5$, OR$^2$, SR$^2$, SOR$^2$, SO$_2$R$^2$, SO$_2$NR$^2$R$^5$, OC(O)NR$^2$R$^5$, R$^{11}$, CH$_3$, SR$^{18}$, SO$_2$R$^{18}$, or N[SO$_2$N($C_{1-3}$ alkyl)$_2$]R$^{18}$; R$^{12}$ is H; each R$^{16}$ is H; and all other variables are as originally defined. In an aspect of this embodiment, R$^{14}$ is also H.

A third embodiment of the present invention is a compound of Formula I, or a pharmaceutically acceptable salt thereof, wherein R$^1$ is H, NR$^2$R$^5$, SCH$_2$C(O)N(CH$_3$)$_2$, SO$_2$CH$_2$C(O)N(CH$_3$)$_2$, or N[SO$_2$N(CH$_3$)$_2$]CH$_2$C(O)N(CH$_3$)$_2$; R$^{12}$ is H; each R$^{16}$ is H; and all other variables are as originally defined. In an aspect of this embodiment, R$^{14}$ is also H.

A fourth embodiment of the present invention is a compound of Formula I, or a pharmaceutically acceptable salt thereof, wherein R$^1$ is NR$^2$R$^5$; R$^{12}$ is H; each R$^{16}$ is H; and all other variables are as originally defined. In an aspect of this embodiment, R$^{14}$ is also H.

A fifth embodiment of the present invention is a compound of Formula I, or a pharmaceutically acceptable salt thereof, wherein R$^2$ is H, CH$_3$, CH$_2$CH$_3$, CH$_2$-cyclopropyl, CH$_2$-phenyl, CH(CH)$_3$-phenyl, or CH$_2$-pyridinyl (e.g., CH$_2$-pyridin-2-yl); and all other variables are as originally defined or as defined in any one of the first four embodiments.

A sixth embodiment of the present invention is a compound of Formula I, or a pharmaceutically acceptable salt thereof, wherein R$^2$ is CH$_3$; and all other variables are as originally defined or as defined in any one of the first four embodiments.

A seventh embodiment of the present invention is a compound of Formula I, or a pharmaceutically acceptable salt thereof, wherein R$^5$ is 1) H,
2) $C_{1-3}$ alkyl, optionally substituted at any carbon atom with halogen, phenyl, SO$_2$CH$_3$, N(CH$_3$)$_2$, or SO$_2$N(CH$_3$)$_2$,
3) C(O)—$C_{1-3}$ alkyl, where the alkyl group is optionally substituted with halogen, phenyl, SO$_2$CH$_3$, N(CH$_3$)$_2$, or SO$_2$NR$^{u*}$R$^{v*}$ wherein R$^{u*}$ and R$^{v*}$ are either both CH$_3$ or together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or $SO_2$, 4) $C(O)CF_3$,
5) $C(O)R^7$,
6) $C(O)C(O)NR^8R^9$,
7) $SO_2NR^8R^9$,
8) $SO_2$—$C_{1-3}$ alkyl, where the alkyl is optionally substituted with halogen, phenyl, $SO_2CH_3$ or $N(CH_3)_2$,
9) $C(O)NR^8R^9$,
10) $SO_2R^7$,
11) $C(O)C(O)R^{10}$, where $R^{10}$ is a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is attached to the rest of the compound via a ring nitrogen and is optionally substituted with from 1 to 3 methyl groups, and wherein any ring S is optionally oxidized to SO or $SO_2$,
12) $C(O)OCH_3$, or
13) $SO_2R^{20}$, wherein $R^{20}$ is a saturated heterocyclic ring independently having the same definition as $R^{10}$ set forth above;

and all other variables are as originally defined or as defined in any one of the first six embodiments.

An eighth embodiment of the present invention is a compound of Formula I, or a pharmaceutically acceptable salt thereof, wherein $R^2$ and $R^5$ together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or $SO_2$; and all other variables are as originally defined or as defined in any one of the first four embodiments.

A ninth embodiment of the present invention is a compound of Formula I, or a pharmaceutically acceptable salt thereof, wherein $R^7$ and $R^{11}$ are each independently an unsaturated heterocycle selected from the group consisting of pyrrolyl, pyrazolyl, imidazolyl, triazolyl, tetrazolyl, oxadiazolyl, pyridinyl, pyrazinyl, pyridazinyl, pyrimidinyl, furyl, thiazolyl, isothiazolyl, oxazolyl, isoxazolyl, quinolinyl, isoquinolinyl, quinazolinyl, cinnolinyl, and triazolopyrimidinyl, in which any one of the N atoms is optionally oxidized and wherein the heterocycle is optionally substituted with from 1 to 3 substituents each of which is methyl; and all other variables are as originally defined or as defined in any one of the preceding embodiments (to the extent such embodiments involve a definition of either or both $R^7$ and $R^{11}$).

A tenth embodiment of the present invention is a compound of Formula I, or a pharmaceutically acceptable salt thereof, wherein $R^8$ and $R^9$ are independently selected from the group consisting of $CH_3$ and phenyl; and all other variables are as originally defined or as defined in any one of the preceding embodiments (to the extent such embodiments involve a definition of $R^8$ and $R^9$).

An eleventh embodiment of the present invention is a compound of Formula I, or a pharmaceutically acceptable salt thereof, wherein $R^{10}$ in the definition of $R^5$ is a saturated heterocyclic ring containing at least one carbon atom, at least one nitrogen atom, and from zero to 3 additional heteroatoms independently selected from N, O and S, wherein any ring S atom is optionally oxidized to SO or $SO_2$, and wherein the heterocyclic ring is attached to the rest of the compound via a ring nitrogen and is optionally substituted with from 1 to 3 substituents each of which is independently a $C_{1-6}$ alkyl group; $R^{20}$ is a saturated heterocyclic ring independently having the same definition as $R^{10}$ just set forth; and all other variables are as originally defined or as defined in any one of the first six embodiments.

A twelfth embodiment of the present invention is a compound of Formula I, or a pharmaceutically acceptable salt thereof, wherein $R^{14}$ is H or $CH_3$; and all other variables are as originally defined or as defined in any one of the preceding embodiments.

A thirteenth embodiment of the present invention is a compound of Formula I, or a pharmaceutically acceptable salt thereof, wherein $R^{18}$ is $CH_2C(O)NR^wR^x$ wherein $R^w$ and $R^x$ are either both $CH_3$ or together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or $SO_2$; and all other variables are as originally defined or as defined in any one of the preceding embodiments (to the extent such embodiments involve a definition of $R^{18}$).

A fourteenth embodiment of the present invention is a compound of Formula I, or a pharmaceutically acceptable salt thereof, wherein $R^3$ is H or $CH_3$; and all other variables are as originally defined or as defined in any one of the preceding embodiments.

A fifteenth embodiment of the present invention is a compound of Formula I, or a pharmaceutically acceptable salt thereof, wherein $R^3$ is H; and all other variables are as originally defined or as defined in any one of the first thirteen embodiments.

A sixteenth embodiment of the present invention is a compound of Formula I, or a pharmaceutically acceptable salt thereof, wherein $R^4$ is $C_{1-3}$ alkyl substituted with an aryl selected from phenyl and naphthyl or with a heteroaryl selected from pyridinyl, pyrimidinyl, pyrazinyl, quinazolinyl, cinnolinyl, quinolinyl, and isoquinolinyl, wherein the aryl or heteroaryl is optionally substituted with from 1 to 3 substituents each of which is independently halo, $CH_3$, $CF_3$, $SO_2CH_3$, or $C(O)NH(CH_3)$; and all other variables are as originally defined or as defined in any one of the preceding embodiments.

A seventeenth embodiment of the present invention is a compound of Formula I, or a pharmaceutically acceptable salt thereof, wherein $R^4$ is:

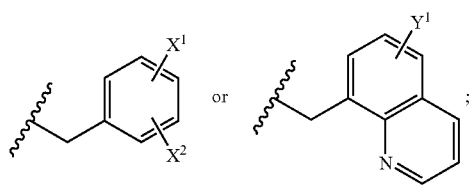

wherein $X^1$ and $X^2$ are each independently hydrogen, bromo, chloro, fluoro, $CH_3$, $CF_3$, $SO_2CH_3$, or $C(O)NH(CH_3)$; and $Y^1$ is hydrogen, bromo, chloro, fluoro, $CH_3$, or $CF_3$; and all other variables are as originally defined or as defined in any one of the first fifteen embodiments.

An eighteenth embodiment of the present invention is a compound of Formula I, or a pharmaceutically acceptable salt thereof, wherein $R^4$ is 1) p-fluorobenzyl, 2) 3-bromo-4-fluorobenzyl, 3) 3-chloro-4-fluorobenzyl, 4) 4-fluoro-3-methylbenzyl, 5) 3,4-difluorobenzyl, 6) 3-chlorobenzyl, 7) p-chlorobenzyl, 8) 3-chloro-4-methylbenzyl, 9) 3-methylbenzyl, 10) 4-fluoro-2-[(methylamino)-carbonyl]benzyl, or 11) quinolin-8-ylmethyl; and all other variables are as originally defined or as defined in any one of the first fifteen embodiments.

A nineteenth embodiment of the present invention is a compound of Formula I, or a pharmaceutically acceptable salt thereof, wherein $R^4$ is p-fluorobenzyl; and all other variables are as originally defined or as defined in any one of the first fifteen embodiments.

A twentieth embodiment of the present invention is a compound of Formula I, wherein each $R^a$ and $R^b$ is independently H or $C_{1-4}$ alkyl; and all other variables are as originally defined or as defined in any one of the foregoing embodiments.

A twenty-first embodiment of the present invention is a compound of Formula I, wherein each $R^a$ and $R^b$ is independently H or methyl; and all other variables are as originally defined or as defined in any one of the first nineteen embodiments.

A twenty-second embodiment of the present invention is a compound of Formula I, wherein n is an integer equal to zero, 1 or 2; and all other variables are as originally defined or as defined in any one of the preceding embodiments. In an aspect of this embodiment, n is 1 or 2. Other aspects of this embodiment include n is 1, and n is 2.

A first class of the present invention includes compounds of Formula I, and pharmaceutically acceptable salts thereof, wherein:

$R^1$, $R^{12}$, and each $R^{16}$ are each independently H, $NR^2R^5$, $OR^2$, $SR^2$, $SOR^2$, $SO_2R^2$, $SO_2NR^2R^5$, $OC(O)NR^2R^5$, $R^{11}$, $CH_3$, $SR^{18}$, $SO_2R^{18}$, or $N[SO_2N(C_{1-3}\ alkyl)_2]R^{18}$; with the proviso that no more than one of $R^1$, $R^{12}$, and $R^{16}$ is other than H or $CH_3$;

$R^2$ is H, $CH_3$, $CH_2CH_3$, $CH_2$-cyclopropyl, $CH_2$-phenyl, $CH(CH)_3$-phenyl, or $CH_2$-pyridinyl;

$R^5$ is

1) H,

2) $C_{1-3}$ alkyl, optionally substituted at any carbon atom with halogen, phenyl, $SO_2CH_3$, $N(CH_3)_2$, or $SO_2N(CH_3)_2$, 3) C(O)—$C_{1-3}$ alkyl, where the alkyl group is optionally substituted with halogen, phenyl, $SO_2CH_3$, $N(CH_3)_2$, or $SO_2NR^{u*}R^{v*}$ wherein $R^{u*}$ and $R^{v*}$ are either both $CH_3$ or together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or $SO_2$,

4) $C(O)CF_3$,

5) $C(O)R^7$,

6) $C(O)C(O)NR^8R^9$,

7) $SO_2NR^8R^9$,

8) $SO_2$—$C_{1-3}$ alkyl, where the alkyl is optionally substituted with halogen, phenyl, $SO_2CH_3$ or $N(CH_3)_2$,

9) $C(O)NR^8R^9$,

10) $SO_2R^7$,

11) $C(O)C(O)R^{10}$, where $R^{10}$ is a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is attached to the rest of the compound via a ring nitrogen and is optionally substituted with from 1 to 3 methyl groups, and wherein any ring S is optionally oxidized to SO or $SO_2$, 12) $C(O)OCH_3$, or 13) $SO_2R^{20}$, wherein $R^{20}$ is a saturated heterocyclic ring independently having the same definition as $R^{10}$ set forth above;

or alternatively $R^2$ and $R^5$ together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or $SO_2$;

$R^7$ and $R^{11}$ are each independently an unsaturated heterocycle selected from the group consisting of pyrrolyl, pyrazolyl, imidazolyl, triazolyl, tetrazolyl, oxadiazolyl, pyridinyl, pyrazinyl, pyridazinyl, pyrimidinyl, furyl, thiazolyl, isothiazolyl, oxazolyl, isoxazolyl, quinolinyl, isoquinolinyl, quinazolinyl, cinnolinyl, and triazolopyrimidinyl, in which any one of the N atoms is optionally oxidized and wherein the heterocycle is optionally substituted with from 1 to 3 substituents each of which is independently methyl;

$R^8$ and $R^9$ are independently selected from the group consisting of $CH_3$ and phenyl;

$R^{14}$ is H or $CH_3$;

$R^{18}$ is $CH_2C(O)NR^wR^x$ wherein $R^w$ and $R^x$ are either both $CH_3$ or together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or $SO_2$;

$R^3$ is hydrogen or $CH_3$;

$R^4$ is $C_{1-3}$ alkyl substituted with an aryl selected from phenyl and naphthyl or with a heteroaryl selected from pyridinyl, pyrimidinyl, pyrazinyl, quinazolinyl, cinnolinyl, quinolinyl, and isoquinolinyl, wherein the aryl or heteroaryl is optionally substituted with from 1 to 3 substituents each of which is independently halo, $CH_3$, $CF_3$, $SO_2CH_3$, or $C(O)NH(CH_3)$; and n is an integer equal to zero, 1, 2, or 3.

A second class of the present invention includes compounds of Formula II, and pharmaceutically acceptable salts thereof:

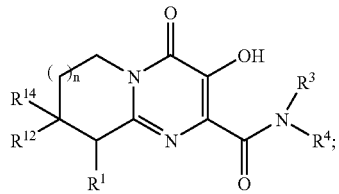

(II)

wherein $R^1$ is H, $NR^2R^5$, $OR^2$, $SR^2$, $SOR^2$, $SO_2R^2$, $SO_2NR^2R^5$, $OC(O)NR^2R^5$, $R^{11}$, $SR^{18}$, $SO_2R^{18}$, or $N[SO_2N(CH_3)_2]SO_2R^{18}$;

$R^2$ is H, $CH_3$, $CH_2CH_3$, $CH_2$-cyclopropyl, $CH_2$-phenyl, $CH(CH_3)_3$-phenyl, or $CH_2$-pyridinyl;

$R^5$ is
1) $C_{1-3}$ alkyl, optionally substituted at any carbon atom with halogen, phenyl, $SO_2CH_3$, $N(CH_3)_2$, or $SO_2N(CH_3)_2$,
2) $C(O)$—$C_{1-3}$ alkyl, where the alkyl group is optionally substituted with halogen, phenyl, $SO_2CH_3$, $N(CH_3)_2$, or $SO_2NR^{u*}R^{v*}$ wherein $R^{u*}$ and $R^{v*}$ are either both $CH_3$ or together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or $SO_2$,
3) $C(O)CF_3$,
4) $C(O)R^7$,
5) $C(O)C(O)NR^8R^9$,
6) $SO_2NR^8R^9$,
7) $SO_2$—$C_{1-3}$ alkyl, where the alkyl is optionally substituted with halogen, phenyl, $SO_2CH_3$ or $N(CH_3)_2$,
8) $C(O)NR^8R^9$,
9) $SO_2R^7$,
10) $C(O)C(O)R^{10}$, where $R^{10}$ is a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is attached to the rest of the compound via a ring nitrogen and is optionally substituted with from 1 to 3 methyl groups, and wherein any ring S is optionally oxidized to SO or $SO_2$,
11) $C(O)OCH_3$, or
12) $SO_2R^{20}$, wherein $R^{20}$ is a saturated heterocyclic ring independently having the same definition as $R^{10}$ set forth above;

or alternatively $R^2$ and $R^5$ together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or $SO_2$;

$R^{12}$ is H or $CH_3$;
$R^{14}$ is H or $CH_3$;
and all other variables are as defined in the first class.

A sub-class of the second class includes compounds of Formula II, and pharmaceutically acceptable salts thereof, wherein $R^3$ is hydrogen; and $R^4$ is:

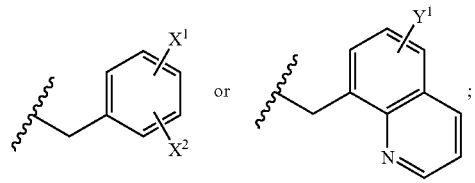

wherein $X^1$ and $X^2$ are each independently hydrogen, bromo, chloro, fluoro, $CH_3$, $CF_3$, $SO_2CH_3$, or $C(O)NH(CH_3)$; and $Y^1$ is hydrogen, bromo, chloro, fluoro, $CH_3$, or $CF_3$;

and all other variables are as defined in the second class.

A third class of the present invention includes compounds of Formula II, and pharmaceutically acceptable salts thereof, wherein $R^1$ is H, $NR^2R^5$, $SCH_2C(O)N(CH_3)_2$, $SO_2CH_2C(O)N(CH_3)_2$, or $N[SO_2N(CH_3)_2]CH_2C(O)N(CH_3)_2$;

$R^2$ is H, $CH_3$, $CH_2CH_3$, $CH_2$-cyclopropyl, $CH_2$-phenyl, $CH(CH_3)_3$-phenyl, or $CH_2$-pyridin-2-yl;

$R^5$ is
1) $CH_3$,
2) $CH_2$-phenyl,
3) $C(O)CH_3$,
4) $C(O)CH_2SO_2CH_3$,
5) $C(O)CH_2SO_2N(CH_3)_2$,
6) $C(O)C(CH_3)_2$—$SO_2N(CH_3)_2$,
7) $C(O)CH_2N(CH_3)_2$,
8) $C(O)CF_3$,
9) $SO_2CH_3$,
10) $SO_2N(CH_3)_2$,
11) $C(O)C(O)N(CH_3)_2$,
12) $C(O)N(CH_3)_2$,
13) $SO_2CH_2SO_2CH_3$,
14) $C(O)OCH_3$,
15) $C(O)$-T, wherein T is:

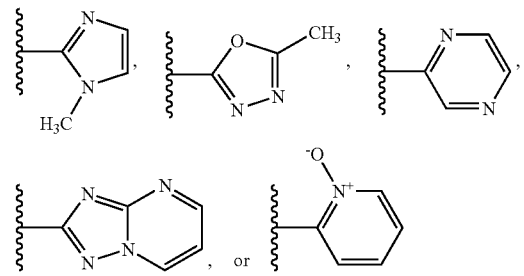

16)

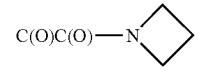

17)

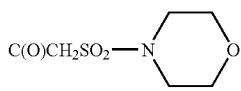

18) SO$_2$-Q, wherein Q is:

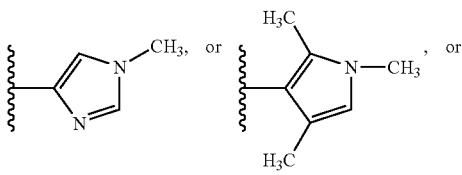

19) SO$_2$R$^{20}$, wherein R$^{20}$ is:

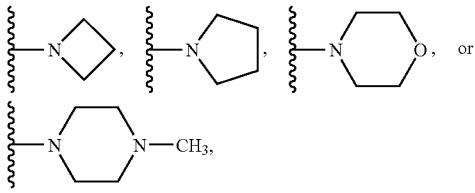

or alternatively R$^2$ and R$^5$ together with the nitrogen atom to which they are attached form a saturated heterocyclic ring selected from the group consisting of

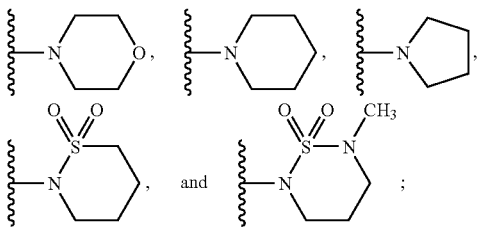

R$^3$ is hydrogen;
R$^4$ is:
1) p-fluorobenzyl,
2) 3-bromo-4-fluorobenzyl,
3) 3-chloro-4-fluorobenzyl,
4) 4-fluoro-3-methylbenzyl,
5) 3,4-difluorobenzyl,
6) 3-chlorobenzyl,
7) p-chlorobenzyl,
8) 3-chloro-4-methylbenzyl,
9) 3-methylbenzyl,
10) 4-fluoro-2-[(methylamino)carbonyl]benzyl, or
11) quinolin-8-ylmethyl;
R$^{12}$ and R$^{14}$ are each independently H or CH$_3$; and
n is an integer equal to zero, 1 or 2.

In a feature of the third class, R$^1$ is H or NR$^2$R$^5$; R$^2$ is CH$_3$; R$^5$ is 1) C(O)CH$_2$SO$_2$CH$_3$, 2) C(O)C(O)N(CH$_3$)$_2$, 3) SO$_2$N(CH$_3$)$_2$, or 4) SO$_2$R$^{20}$, wherein R$^{20}$ is:

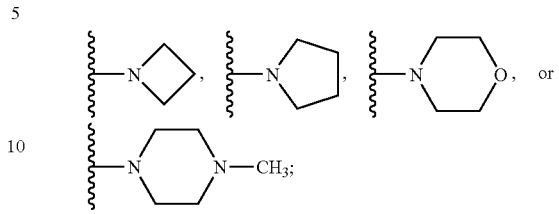

or alternatively R$^2$ and R$^5$ together with the nitrogen atom to which they are attached form

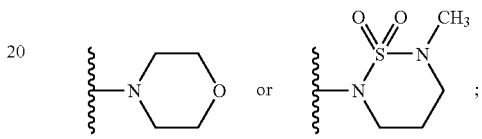

R$^3$ is hydrogen; R$^4$ is p-fluorobenzyl, 4-fluoro-3-methylbenzyl, 3-chlorobenzyl, or 3-chloro-4-methylbenzyl; R$^{12}$ and R$^{14}$ are both H, except that when R$^5$ is C(O)C(O)N(CH$_3$)$_2$ and R$^4$ is p-fluorobenzyl and n is 1, then R$^{12}$ and R$^{14}$ are either both H or both CH$_3$; and n is an integer equal to zero, 1 or 2.

In another feature of the third class, R$^1$ is NR$^2$R$^5$; n is an integer equal to 1 or 2; and all other variables are as defined in the preceding feature of the third class.

In still another feature of the third class, R$^1$ is NR$^2$R$^5$; R$^2$ is CH$_3$; R$^5$ is 1) C(O)C(O)N(CH$_3$)$_2$ or 2) SO$_2$R$^{20}$, wherein R$^{20}$ is

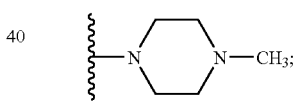

R$^3$ is hydrogen; R$^4$ is p-fluorobenzyl or 4-fluoro-3-methylbenzyl; R$^{12}$ and R$^{14}$ are both H, except that when R$^5$ is C(O)C(O)N(CH$_3$)$_2$ and R$^4$ is p-fluorobenzyl and n is 1, then R$^{12}$ and R$^{14}$ are either both H or both CH$_3$; and n is an integer equal to 1 or 2.

A twenty-third embodiment of the present invention is a compound of Formula III, or a pharmaceutically acceptable salt thereof:

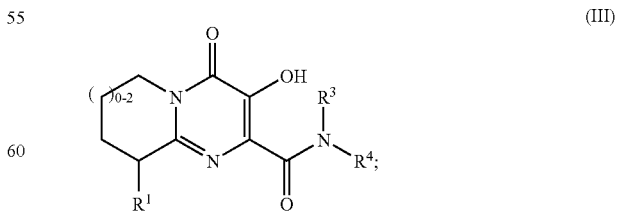

(III)

wherein
R$^1$ is hydrogen, NR$^2$R$^5$, OR$^2$, SR$^2$, SOR$^2$, SO$_2$R$^2$, SO$_2$NR$^2$R$^5$, OC(O)NR$^2$R$^5$, or R$^{11}$;

$R^2$ is 1) hydrogen, 2) $C_{1-6}$ alkyl, or 3)

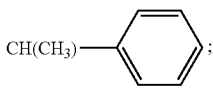

$R^5$ is
1) $C_{1-6}$ alkyl, unsubstituted or substituted at any carbon atom with halogen, aryl, $SO_2CH_3$ or $N(CH_3)_2$,
2) $C(O)C_{1-6}$ alkyl, where alkyl is unsubstituted or substituted at any carbon atom with halogen, aryl, $SO_2CH_3$ or $N(CH_3)_2$,
3) $C(O)CF_3$,
4) $C(O)R^7$,
5) $C(O)C(O)NR^8R^9$,
6) $SO_2NR^8R^9$,
7) $SO_2C_{1-6}$ alkyl, where alkyl is unsubstituted or substituted at any carbon atom with halogen, aryl, $SO_2CH_3$ or $N(CH_3)_2$,
8) $C(O)NR^8R^9$,
9) $SO_2R^7$, or
10) $C(O)C(O)R^{10}$, where $R^{10}$ is a 4, 5 or 6-membered saturated heterocyclic ring containing 1 or 2 heteroatoms independently selected from N, O and S;

or $R^2$ and $R^5$, together with the nitrogen atom to which they are attached, form a 5- or 6-membered saturated heterocyclic ring containing 1 or 2 heteroatoms independently selected from N, O and S;

$R^7$ and $R^{11}$ are independently a 5- or 6-membered unsaturated heterocyclic ring containing 1, 2 or 3 heteroatoms independently selected from N, O and S;

and $R^3$, $R^4$, $R^8$, and $R^9$ are as originally defined.

A fourth class of the invention includes compounds of Formula III, and pharmaceutically acceptable salts thereof, wherein $R^3$ is hydrogen; and $R^4$ is $(CH_2)_{1-3}R^6$, wherein $R^6$ is selected from the group consisting of $C_{1-6}$ alkyl, $C_{3-8}$ cycloalkyl, and aryl, and wherein $R^6$ is unsubstituted or substituted with halogen; and all other variables are as defined in the twenty-third embodiment.

In a subclass of the fourth class,
$R^4$ is

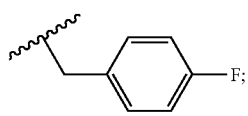

$R^2$ is
1) hydrogen,
2) $CH_3$, or
3)

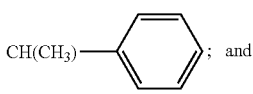
; and $R^5$ is
1) $C(O)CH_3$,
2) $C(O)CH_2SO_2CH_3$,
3) $CH_3$,
4) $C(O)C(O)N(CH_3)_2$,
5) $SO_2CH_3$,
6) $SO_2N(CH_3)_2$,
7) $C(O)CH_2N(CH_3)_2$,
8) $SO_2CH_2SO_2CH_3$,
9) $C(O)CF_3$,
10)

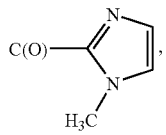

11)

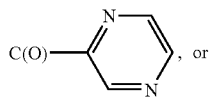
, or

12)

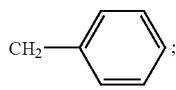
;

or $R^2$ and $R^5$, together with the nitrogen atom to which they are attached, form a heterocyclic ring selected from the group consisting of

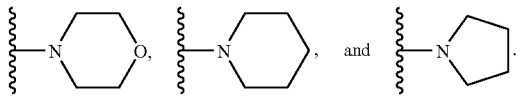

A twenty-fourth embodiment of the present invention is a compound, or a pharmaceutically acceptable salt thereof, selected from the group consisting of the compounds set forth in Table 1 below.

Other embodiments of the present invention include the following:

(a) A pharmaceutical composition comprising a compound of Formula (I) and a pharmaceutically acceptable carrier.

(b) A pharmaceutical composition which comprises the product prepared by combining (e.g., mixing) an effective amount of a compound of Formula (I) and a pharmaceutically acceptable carrier.

(c) The pharmaceutical composition of (a) or (b), further comprising a therapeutically effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A combination useful for inhibiting HIV integrase, for treating or preventing infection by HIV, or for preventing, treating or delaying the onset of AIDS, which is a therapeutically effective amount of a compound of Formula I and a therapeutically effective amount of an HIV infection/AIDS treatment agent selected from the group consisting of HIV/ AIDS antiviral agents, immunomodulators, and anti-infective agents.

(f) The combination of (e), wherein the HIV infection/ AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject a therapeutically effective amount of a compound of Formula I.

(h) A method of preventing or treating infection by HIV in a subject in need thereof which comprises administering to the subject a therapeutically effective amount of a compound of Formula I.

(i) The method of (h), wherein the compound of Formula (I) is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject a therapeutically effective amount of a compound of Formula I.

(k) The method of (j), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

As used herein, the term "$C_{1-6}$ alkyl" (or "$C_1$-$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. Unless otherwise indicated, "alkyl" can be unsubstituted or substituted with one or more substituents selected from the group consisting of halogen, OH, CN, O—$C_{1-6}$ alkyl, O—$C_{1-6}$ haloalkyl, C(O)R$^e$, COOR$^e$, SR$^e$, S(O)R$^e$, NR$^e$R$^f$, C(O)—$C_{0-6}$alkylene-NR$^e$R$^f$, NR$^e$C(O)—$C_{0-6}$ alkylene-NR$^f$R$^g$, SO$_2$R$^e$, NR$^e$SO$_2$R$^f$, SO$_2$NR$^e$R$^f$, NR$^e$C(O)R$^f$, and N(R$^e$)C(NR$^f$)NR$^g$ R$^h$, wherein R$^e$, R$^f$, R$^g$ and R$^h$ are independently selected from the group consisting of hydrogen and $C_{1-6}$ alkyl.

The term "$C_0$" as employed in expressions such as "$C_{0-6}$ alkyl" means a direct covalent bond.

The term "—$C_{1-6}$ alkylene-" (e.g., as in the substituent "—$C_{1-6}$ alkylene-OR$^a$") refers to any linear or branched chain alkylene (or alternatively "alkanediyl") having from 1 to 6 carbon atoms. A class of alkylenes of particular interest with respect to the invention is —(CH$_2$)$_{1-6}$—, and sub-classes of particular interest include —(CH$_2$)$_{1-4}$—, —(CH$_2$)$_{1-3}$—, —(CH$_2$)$_{1-2}$—, and —CH$_2$—. Also of interest is the alkylene —CH(CH$_3$)—.

The term "$C_{2-5}$ alkynyl" (or "$C_2$-$C_5$ alkynyl") means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "$C_{3-7}$ azacycloalkyl" (or "$C_3$-$C_7$ azacycloalkyl") means a saturated cyclic ring consisting of one nitrogen and from three to seven carbon atoms (i.e., azetidinyl, pyrrolidinyl, piperidinyl, azepanyl, or octahydroazocinyl).

The term "halogen" (or "halo") refers to fluorine, chlorine, bromine and iodine (alternatively referred to as fluoro, chloro, bromo, and iodo).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series (CH$_2$)$_{0-4}$CF$_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein refers to (i) a $C_3$ to $C_8$ monocyclic, saturated or unsaturated ring, (ii) a $C_7$ to $C_{12}$ bicyclic ring system, or (iii) a $C_{11}$ to $C_{16}$ tricyclic ring system, wherein each ring in (ii) or (iii) is independent of, bridged with, or fused to the other ring or rings and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a C7 to C10 bicyclic ring system in which each ring is saturated or unsaturated and two adjacent carbon atoms are shared by each of the rings in the ring system. Fused tricyclic carbocycles have an analogous meaning. A subset of the fused bicyclic carbocycles are those bicyclic carbocycles in which one ring is a benzene ring and the other ring is saturated or unsaturated, with attachment via any carbon atom that results in a stable compound. Representative examples of this subset include the following:

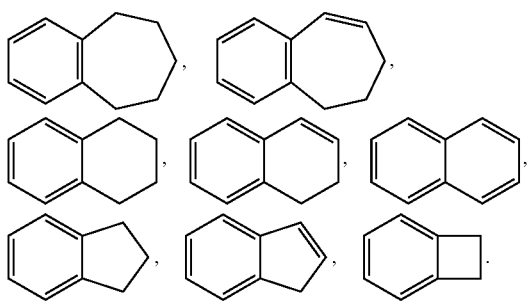

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl. Unless otherwise indicated, "aryl" may be unsubstituted or substituted with a substituent selected from the group consisting of halogen, $C_{1-6}$ alkyl, $C_{1-6}$ haloalkyl, O—$C_{1-6}$ alkyl, O—$C_{1-6}$ haloalkyl, $C_{0-6}$ alkylene-$NR^iR^j$, $C_{1-6}$ alkyl substituted with a 5- or 6-membered saturated heterocyclic ring containing from 1 to 4 heteroatoms independently selected from N, O and S, wherein the saturated ring is unsubstituted or substituted with 1 to 3 substituents each of which is independently selected from $C_{1-6}$ alkyl, oxo, or 5- to 6-membered heteroaromatic ring containing from 1 to 4 heteroatoms independently selected from N, O and S, wherein $R^i$ and $R^j$ are independently selected from the group consisting of hydrogen and $C_{1-6}$ alkyl. In a preferred aspect of this invention, aryl is phenyl or naphthyl. In a more preferred aspect, aryl is phenyl.

The term "heterocycle" (and variations thereof such as "heterocyclic" or "heterocyclyl") broadly refers to (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of, bridged with, or fused to the other ring or rings and each ring is saturated or unsaturated, and the monocyclic ring, bicyclic ring system, or tricyclic ring system contains one or more heteroatoms (e.g., from 1 to 6 heteroatoms, or from 1 to 4 heteroatoms, or from 1 to 3 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally be oxidized, and any one or more of the nitrogen heteroatoms is optionally quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

4, 5 or 6-membered saturated heterocyclic rings containing 1 or 2 heteroatoms are exemplified by morpholine, piperidine, piperazine and pyrrolidine.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring which consists of carbon atoms and one or more heteroatoms selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl

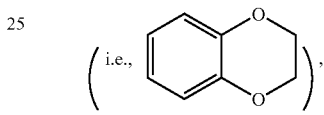

and benzo-1,3-dioxolyl

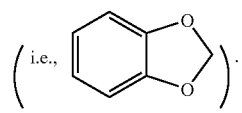

Representative examples of tricyclic heterocycles include phenothiazinyl, carbazolyl, beta-carbolinyl, tetrahydro-beta-carbolinyl, acridinyl, phenazinyl, and phenoxazinyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

When any variable (e.g., $R^a$ and $R^b$) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound.

The symbol " ~~ "in front of an open bond in the structural formula of a group marks the point of attachment of the group to the rest of the molecule.

The compounds of the present invention may have asymmetric centers and may occur, except when specifically noted, as mixtures of stereoisomers or as individual diastereomers, or enantiomers, with all isomeric forms being included in the present invention.

The N-substituted hydroxypyrimidinone compounds of the present invention may also occur as tautomers thereof, such as the following tautomer of a compound of Formula I:

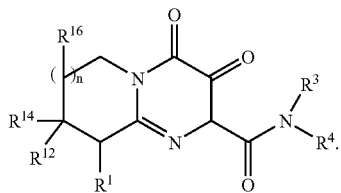

It is understood that the present invention includes all tautomers of the hydroxypyrimidinone compounds of Formula A or Formula I (or II or III), both singly and in mixtures.

The compounds of the present inventions are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

Compounds representative of the present invention have been tested for inhibition in an assay for the strand transfer activity of integrase. The assay is conducted in the manner described in WO 02/30930. The assay is also in accordance with Wolfe, A. L. et al., *J. Virol.* 1996, 70: 1424-1432, for recombinant integrase, except that: (i) the assay uses preassembled integrase strand transfer complexes; (ii) the strand transfer reaction is performed in the presence of inhibitor in 2.5 mM $MgCl_2$ using 0.5 to 5 nM of a 3' FITC labeled target DNA substrate, and (iii) strand transfer products are detected using an alkaline phosphatase conjugated anti-FITC antibody and a chemiluminescent alkaline phosphatase substrate. Representative compounds of the present invention exhibit inhibition of strand transfer activity in this assay. For example, the compounds set forth in Table 1 below were tested in the integrase assay and demonstrated $IC_{50}$'s of about 5 micromolar or less. Further description on conducting the assay using preassembled complexes is found in Hazuda et al., *J. Virol.* 1997, 71: 7005-7011; Hazuda et al., *Drug Design and Discovery* 1997, 15: 17-24; and Hazuda et al., *Science* 2000, 287: 646-650.

Certain compounds representative of the present invention have also been tested in an assay for inhibition of acute HIV infection of T-lymphoid cells, conducted in accordance with Vacca, J. P. et al., *Proc. Natl. Acad. Sci. USA* 1994, 91: 4096. These compounds—including the compounds set forth below in Table 1—demonstrated $IC_{95}$'s of about 20 micromolar or less.

The compounds of the present invention can also act as inhibitors of HIV ribonuclease H(RNase H). The human immunodeficiency virus type 1 (HIV-1) reverse transcriptase (RT) catalyzes the conversion of genomic RNA into double-stranded proviral DNA after cell entry, utilizing the RNA- and DNA-dependent polymerase and RNase H activities of the enzyme. HIV-1 RT is an asymmetric dimer consisting of p66 and p51 polypeptides. The catalytic activities of RT are conducted at discrete sites in the p66 subunit; i.e., the N terminus of p66 catalyzes the RNA- and DNA-dependent DNA polymerase activity, and the p15 domain at the C terminus catalyzes RNase H activity. RNase H is required to cleave the RNA strand of the RNA:DNA heteroduplex intermediates in reverse transcription. The compounds of the present invention can selectively bind to and inhibit the RNase H domain of HIV-1 RT. The RNase H inhibition activity of the compounds can be measured using suitable assays known in the art, such as the assay described in Shaw-Reid et al., *J. Biol. Chem.* 2003, 278 (5): 2777-2780. Accordingly, the present invention includes a method of inhibiting HIV RNase H in a subject in need of such inhibition which comprises administering to the subject an effective amount of a compound of the invention. The present invention further includes a compound of the present invention (i) for use in, (ii) for use as a medicament for, or (iii) for use in the preparation of a medicament for inhibiting HIV RNase H.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When the compounds of the invention carry an acidic moiety, suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

For the purpose of inhibiting HIV integrase or HIV RNase H, preventing or treating HIV infection or preventing, treating or delaying the onset of AIDS, the compounds of the present invention may be administered orally, parenterally (including subcutaneous injections, intravenous, intramuscular, intrasternal injection or infusion techniques), by inhalation spray, or rectally, in the form of a unit dosage of a pharmaceutical composition containing a therapeutically effective amount of the compound and conventional non-toxic pharmaceutically-acceptable carriers, adjuvants and vehicles.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HIV infection or AIDS), "administration" and its variants are each understood to include concurrent and sequential provision of the compound or prodrug and other agents.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation or prophylaxis of the symptoms of the disease or condition being treated or prevented. The term also includes herein the amount of active compound sufficient to inhibit HIV integrase and/or RNase H and thereby elicit the response being sought. When the active compound (i.e., active ingredient) is administered as the salt, references to the amount of active ingredient are to the free acid or free base form of the compound.

The pharmaceutical compositions may be in the form of orally-administrable suspensions or tablets or capsules, nasal sprays, sterile injectable preparations, for example, as sterile injectable aqueous or oleagenous suspensions or suppositories. These compositions can be prepared by methods and contain excipients which are well known in the art. Suitable methods and ingredients are described in *Remington's Pharmaceutical Sciences*, 18$^{th}$ edition, edited by A. R. Gennaro, Mack Publishing Co., 1990, which is herein incorporated by reference in its entirety.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more HIV/AIDS antivirals, immunomodulators, antiinfectives, or vaccines useful for treating HIV infection or AIDS, such as those disclosed in Table 1 of WO 01/38332 or in the Table in WO 02/30930, both documents being herein incorporated by reference in their entireties. It will be understood that the scope of combinations of the compounds of this invention with HIV/AIDS antivirals, immunomodulators, anti-infectives or vaccines is not limited to the list in the above-referenced Tables in WO 01/38332 and WO 02/30930, but includes in principle any combination with any pharmaceutical composition useful for the treatment of AIDS. The HIV/AIDS antivirals and other agents will typically be employed in these combinations in their conventional dosage ranges and regimens as reported in the art, including, for example, the dosages described in the *Physicians' Desk Reference*, 57$^{th}$ edition, Thomson PDR, 2003. The dosage ranges for a compound of the invention in these combinations are the same as those set forth above.

Abbreviations used in the instant specification, particularly the Schemes and Examples, include the following: AIDS=acquired immunodeficiency syndrome, ARC=AIDS related complex, Bn=benzyl, CBZ (or Cbz)=benzyloxycarbonyl, DBU=1,8-diazabicyclo[5.4.0]undec-7-ene, DMAD=dimethylacetylenedicarboxylate, DMF=N,N-dimethylformamide, DMSO=dimethylsulfoxide, EtOAc=ethyl acetate, FIA-MS=flow injection analysis mass spectrometry, h=hour(s), HIV=human immunodeficiency virus, HPLC=high performance liquid chromatography, IPA=isopropanol, LDA=lithium diisopropylamide, Me=methyl, MeOH=methanol, NMP=N-methylpyrrolidinone, NMR=nuclear magnetic resonance, Pd/C=palladium on carbon catalyst, RP-HPLC=reversed phase HPLC, TFA=trifluoroacetic acid, THF=tetrahydrofuran.

The compounds of the present invention can be readily prepared according to the following reaction schemes and examples, or modifications thereof, using readily available starting materials and reagents. In the reactions shown below, it is also possible to make use of variants which are themselves known to those of ordinary skill in this art, but are not mentioned in greater detail. Furthermore, other methods for preparing compounds of the invention (including compounds embraced by Formula A and Formula I but whose preparation is not literally described below) will be readily apparent to the person of ordinary skill in the art in light of the following reaction schemes and examples. Unless otherwise defined, the variables listed in Schemes 1, A, B, C, D and E have the following meanings:

$P^\wedge$ is hydrogen or a protective group, e.g., an ester such as, but not limited to, benzoate and pivalate, or an ether such as, but not limited to, a benzyl ether, that is normally removed under the conditions employed to convert the methyl ester to the amide or is removed in a different step. The protective group is typically used for synthetic and/or purification reasons.

$R^\wedge$ is hydrogen or $C_{1-6}$ alkyl

Y is hydrogen or $NR^{sa}R^{sb}$.

$R^{sa}$ is $C_{1-6}$ alkyl, $C(O)R^{sc}$, $C(O)C(O)NR^{sc}R^{sd}$, $SO_2R^{sc}$, $SO_2NR^{sc}R^{sd}$, $C(O)CH_2SO_2R^{sc}$, $C(O)CH_2NR^{sc}R^{sd}$, $SO_2CH_2SO_2R^{sc}$, or $CH(CH_3)R^{sc}$, or $R^{sa}$ and $R^{sb}$, together with the nitrogen atom to which they are attached, form a heterocyclic ring containing 1 or 2 heteroatoms.

$R^{sb}$ is hydrogen, $C_{1-6}$ alkyl, or $C(O)CF_3$, or $R^{sa}$ and $R^{sb}$, together with the nitrogen atom to which they are attached, form a heterocyclic ring containing 1 or 2 heteroatoms.

$R^{sc}$ is $C_{1-6}$ alkyl, aryl, a 5- or 6-membered heteroaryl ring which is unsubstituted or substituted with $C_{1-6}$ alkyl, $C(O)$ $CH_2SO_2C_{1-6}$ alkyl, or $(CH_2)_{1-6}$ aryl.

$R^{sd}$ is $C_{1-6}$ alkyl.

$R^{s5}$ is $R^{sc}$, $C(O)NR^{sc}R^{sd}$, $CH_2SO_2R^{sc}$, $CH_2NR^{sc}R^{sd}$, $NR^{sc}R^{sd}$, or $CH_2SO_2R^{sc}$.

$R^{s1}$ is hydrogen.

$R^{s2}$ is $CH_2R^{se}$, wherein $R^{se}$ is unsubstituted aryl or aryl substituted with halogen.

The compounds of the present invention can be prepared by coupling the appropriate amines with suitable substituted alkyl 3-hydroxy-4-oxo-6,7,8,9-tetrahydro-4H-pyrido[1,2-a]pyrimidine-2-carboxylate (or carboxylic acids or halides) or alkyl 3-hydroxy-4-oxo-4,6,7,8-tetrahydropyrrolo[1,2-a]pyrimidine-2-carboxylate (or carboxylic acids or halides) or alkyl 3-hydroxy-4-oxo-4,6,7,8,9,10-hexahydropyrimido[1,2-a]azepine-2-carboxylate (or carboxylic acids or halides) or alkyl 3-hydroxy-4-oxo-6,7,8,9,10,11-hexahydro-4H-pyrimido[1,2-a]azepine-2-carboxylate (or carboxylic acids or halides), as represented by Scheme 1.

Scheme 1

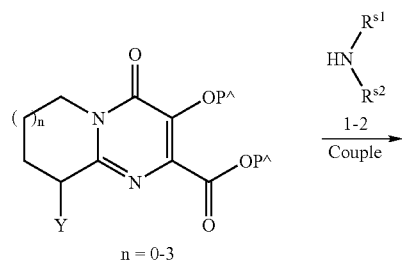

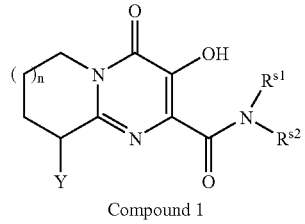

Compound 1

Methods for coupling carboxylic acid derivatives with amines to form carboxamides are well known in the art. Suitable methods are described, for example, in Jerry March, *Advanced Organic Chemistry*, 3rd edition, John Wiley & Sons, 1985, pp. 370-376. Amines of formula 1-2 can be prepared using the methods described in Richard Larock, *Comprehensive Organic Transformations*, VCH Publishers Inc, 1989, pp 385-438, or routine variations thereof.

Scheme A depicts a general synthesis of carboxamides A-5. The methyl ester A-4 can be reacted with an amine 1-2 in solvents like DMF, methanol, ethanol, toluene, NMP at the appropriate temperature (e.g., from 20 to 150° C.) to give the final compound A-5. Methyl ester A-4 can be synthesized by one of three synthetic routes. In the first route, amidine hydrochloride A-1a (sX=H; sY=H) can be reacted with dimethyl 2-(benzyloxy)-3-oxosuccinate in the presence of a base to afford the protected methyl ester intermediate A-2, which can be readily deprotected to afford the methyl ester A-4. In a second route, amidoxine A-1b (sX=OH; sY=H), obtained in three steps from tert-butyl benzyloxycarbamate, can be reacted with DMAD to afford the cyclic intermediate A-3a, which can be rearranged by heating in an appropriate solvent (e.g., xylene) to afford the methyl ester A-5. In a third route, amidoxyme A-1c (sX=H; sY=OH) can be reacted with DMAD in an appropriate solvent (e.g., acetonitrile) to afford the intermediate A3-b, which can be rearranged to the methyl ester A-4 by heating in an appropriate solvent (e.g., xylene). All three of these routes can be applied to amidines and amidoxymes containing ring substituents. Scheme A is exemplified in Examples 1, 9 and 14.

Scheme A

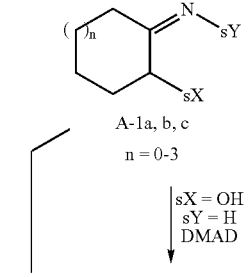

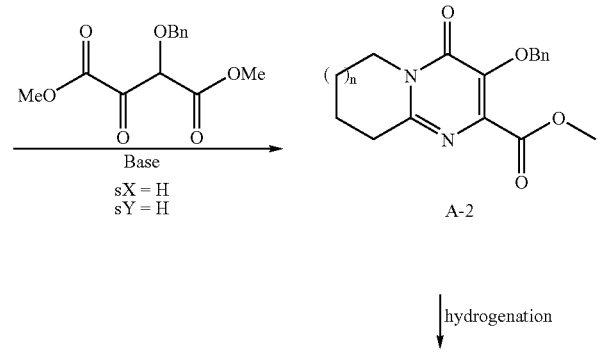

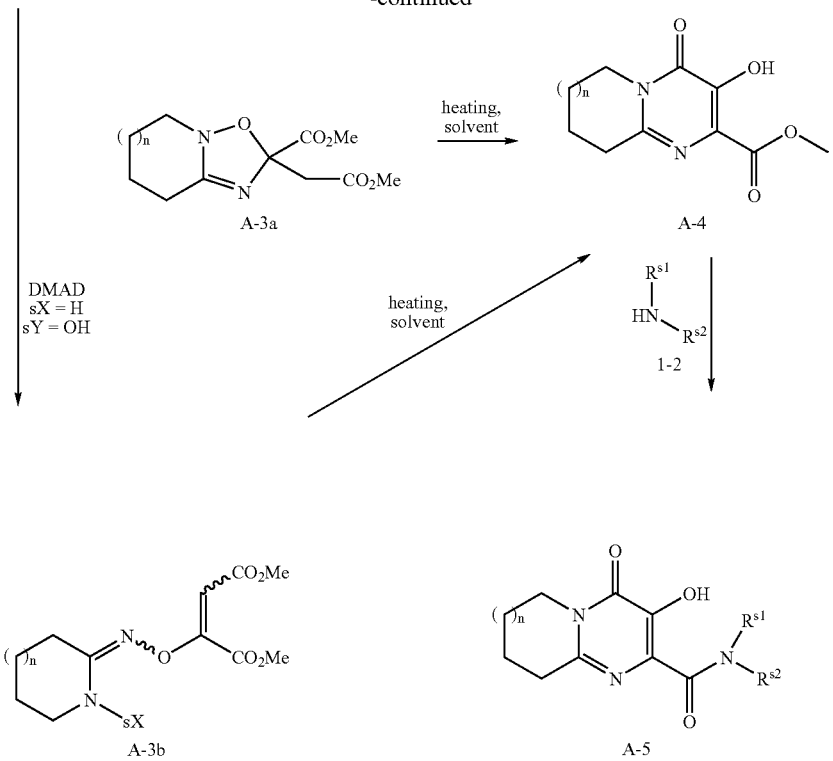

Scheme B shows a method for preparing compounds of the present invention that contain an amine, ether, thioether, sulfoxide or sulfone group at the 9-position of the 3-hydroxy-4-oxo-6,7,8,9-tetrahydro-4H-pyrido[1,2-a]pyrimidine-2-carboxamide core. The bromo derivative B-1 can be obtained from methyl ester A-4 by first protecting the hydroxy group on A-4 with a suitable protective group (e.g., conversion to a benzoate or pivalate or to benzyloxy) and then contacting the protected A-4 with a brominating agent (e.g., NBS). The bromo derivative B-1 can then be treated with a nucleophile ("Nu"; e.g. an amine, thiol or alcoholate) to afford with or without isolation the methyl ester intermediate B-2, that is reacted with the desired amine to give the final product B-3. If the nucleophile is a thiol or contains an oxidizable sulfur, an oxidation step to obtain the sulfoxide or sulfone can be included in the scheme. If the nucleophile contains an ester, the ester can be converted to an amide by routine chemistry after the synthesis of B-3. Scheme B is exemplified in Example 2.

Scheme B

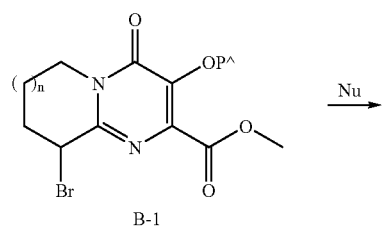

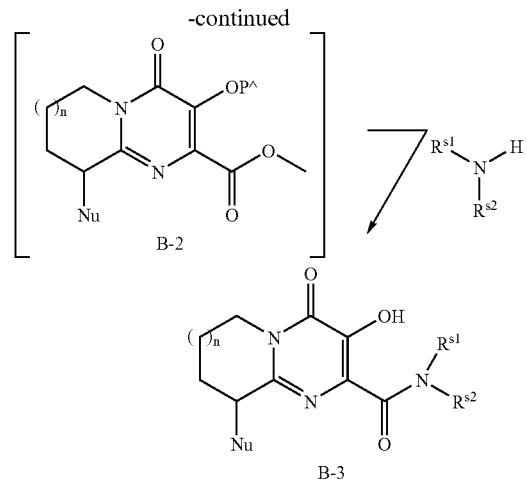

n = 0-3

Scheme C depicts a general synthesis of derivatives C-3 or C-4 containing an aliphatic ring substituent such as amide, sulfonamide, sulfonylurea, carbamate, or urea. The bromo derivative B-1 can be treated with benzylamine C-1 and then hydrogenated or reacted directly with amine C-1a to give intermediate C-2, which can then be treated with amine 1-2, with or without isolation, and then coupled with a carboxylic acid or reacted with a carbonyl chloride (or sulfonyl chloride or sulfamoyl chloride) or isocyanate to afford the final product C-3. If C-3 contains $R^{s4}=R^{s3}O(CO)CO$, it can be further reacted with a nucleophile such as an amine to afford the product C-4. Scheme C is exemplified in Examples 3, 4, 10 and 11. The last two steps can be reversed.

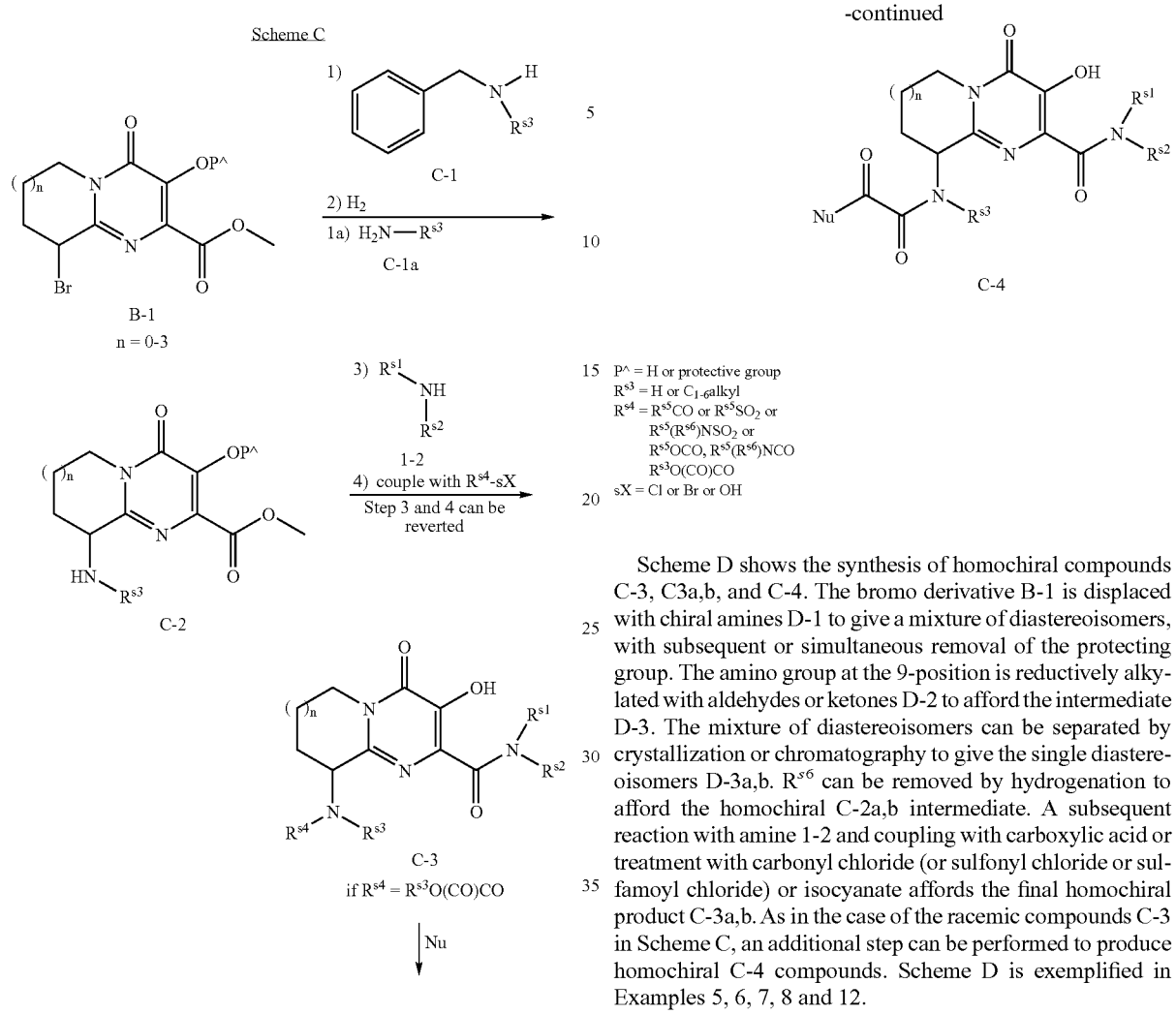

$P^{\wedge}$ = H or protective group
$R^{s3}$ = H or $C_{1\text{-}6}$alkyl
$R^{s4}$ = $R^{s5}CO$ or $R^{s5}SO_2$ or
$R^{s5}(R^{s6})NSO_2$ or
$R^{s5}OCO$, $R^{s5}(R^{s6})NCO$
$R^{s3}O(CO)CO$
sX = Cl or Br or OH Scheme D shows the synthesis of homochiral compounds C-3, C3a,b, and C-4. The bromo derivative B-1 is displaced with chiral amines D-1 to give a mixture of diastereoisomers, with subsequent or simultaneous removal of the protecting group. The amino group at the 9-position is reductively alkylated with aldehydes or ketones D-2 to afford the intermediate D-3. The mixture of diastereoisomers can be separated by crystallization or chromatography to give the single diastereoisomers D-3a,b. $R^{s6}$ can be removed by hydrogenation to afford the homochiral C-2a,b intermediate. A subsequent reaction with amine 1-2 and coupling with carboxylic acid or treatment with carbonyl chloride (or sulfonyl chloride or sulfamoyl chloride) or isocyanate affords the final homochiral product C-3a,b. As in the case of the racemic compounds C-3 in Scheme C, an additional step can be performed to produce homochiral C-4 compounds. Scheme D is exemplified in Examples 5, 6, 7, 8 and 12.

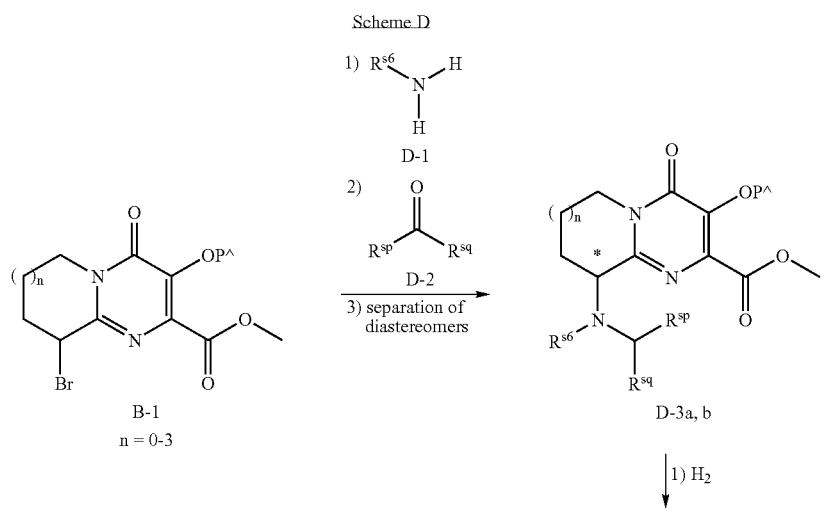

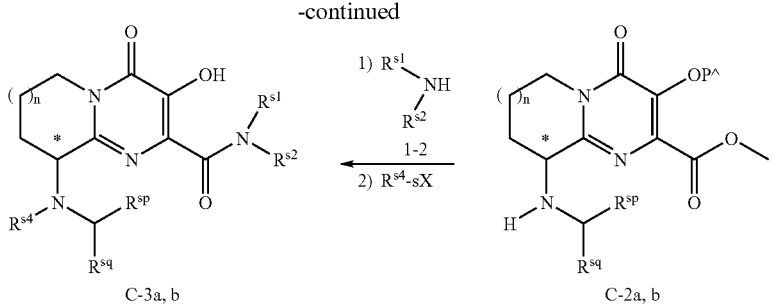

C-3a, b                                           C-2a, b $P^{\wedge}$ = H or protective group
$R^{s6}$ = chiral alkyl residue (e.g. (S)-a-methylbenzyl)
$R^{sp}$, $R^{sq}$ = H or $C_{1\text{-}6}$alkyl
$R^{s4}$ = $R^{s5}CO$ or $R^{s5}SO_2$ or $R^{s5}(R^{s6})NSO_2$ or $R^{s5}OCO$, $R^{s3}O(CO)CO$ $R^{s5}(R^{s6})NCO$
sX = Cl or Br or OH Scheme E shows a method for preparing compounds of the present invention that contain a nucleophilic substituent Nu (e.g., an amine, hydroxylamine, ether or thioether group) at the 8 position of the pyridopyrimidine core. The bromo derivative B-1 (see Scheme B), can be treated with a base in an aprotic solvent at high temperature (e.g., 50 to 120° C.) to afford the intermediate E-1, which can be reacted with the desired nucleophile (e.g. an amine, hydroxylamine, thiol or alcoholate) to give the addition product E-2. This in turn can be reacted with the desired amine to give the final product E-3. The substituent in the 8-position can be further elaborated by procedures known to those of ordinary skill in the art. For example, a hydroxylamine can be reduced to an amine, which can then be alkylated, acylated, sulfonylated etc. Scheme E is exemplified in Example 15.

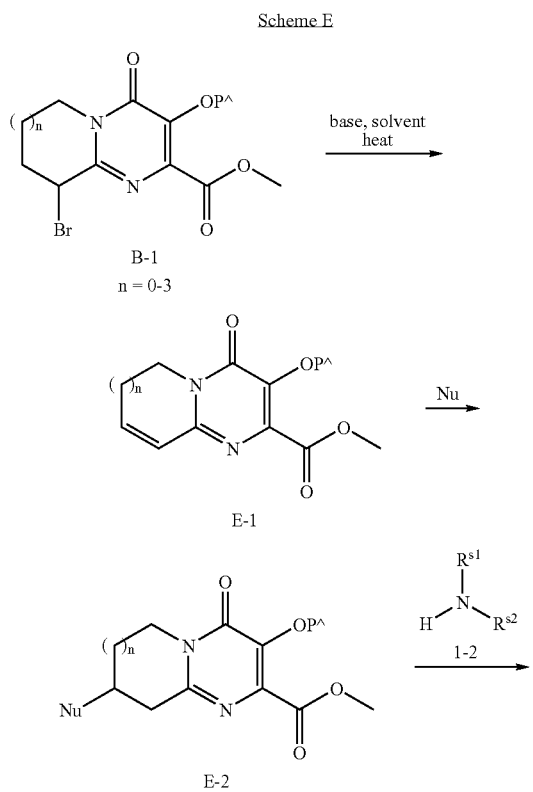

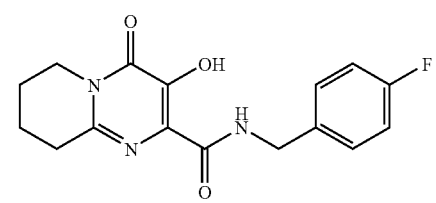

E-3

The following examples serve only to illustrate the invention and its practice. The examples are not to be construed as limitations on the scope or spirit of the invention.

Example 1

N-(4-Fluorobenzyl)-3-hydroxy-4-oxo-6,7,8,9-tetrahydro-4H-pyrido[1,2-a]pyrimidine-2-carboxamide Step 1a: Tert-butyl benzyloxy(4-cyanobutyl)carbamate (Bergeron, R. J., McManis, J. S., Tetrahedron 45 (16), 4939-4944 (1989)

To a solution of tert-butyl benzyloxycarbamate in anhydrous dimethylformamide were added 5 mol % of sodium iodide and portionwise 1.36 eq. of sodium hydride (60% dispersion in mineral oil). The mixture was stirred at room temperature for 15 min. before 1.05 eq. of 4-chlorovaleronitrile were added. The mixture was heated to 85° C. and stirred for 3.5 h. After cooling to room temperature the mixture was quenched with water and extracted with diethyl ether. The combined organic phases were concentrated and washed with half saturated aq. sodium thiosulfate, water and brine. The organic phase was dried over sodium sulfate, filtered and concentrated under reduced pressure. The oily residue was washed with petroleum ether and dried under high vacuum to yield Tert-butyl benzyloxy(4-cyanobutyl)carbamate as a light yellow oil.

1H-NMR (400 MHz, CDCl$_3$) δ: 7.38 (m, 5H), 4.84 (s, 2H), 3.45 (t, J=6.4 Hz, 2H), 2.34 (t, J=6.8 Hz, 2H), 1.70 (m, 4H), 1.52 (s, 9H). MS m/z: 271 (M+H)+.

Step 2a: 1-(Benzyloxy)piperidin-2-imine hydrochloride

Tert-butyl benzyloxy(4-cyanobutyl)carbamate was dissolved in a solution of 4 M HCl in 1,4-dioxane and the mixture was stirred for 18 h at room temperature. The solvent was removed under reduced pressure and the residue was treated with ethyl acetate and diethyl ether. A solid formed which was washed with diethyl ether, filtered and dried under high vacuum to give 1-(benzyloxy)piperidin-2-imine hydrochloride as a pale yellow solid.

1H-NMR (400 MHz, DMSO-d6) δ: 9.53 (s, 1H), 8.97 (s, 1H), 7.57-7.41 (m, 5H), 5.05 (s, 2H), 3.67 (t, J=6.0 Hz, 2H), 2.64 (t, J=6.4 Hz, 2H), 1.90-1.84 (m, 2H), 1.69-1.63 (m, 2H). MS m/z: 205 (M+H)$^+$.

Step 3a: 2-Iminopiperidin-1-ol hydrochloride

A solution of 1-(benzyloxy)piperidin-2-imine hydrochloride in methanol, containing palladium on charcoal (10%, w/w) was stirred under hydrogen at atmospheric pressure for 3 h. The catalyst was filtered off and the solution was concentrated to dryness under reduced pressure. The residue was triturated with diethyl ether, filtered and dried under high vacuum to afford 2-iminopiperidin-1-ol hydrochloride as a pale yellow solid.

1H-NMR (400 MHz, DMSO-d6) δ: 11.76 (s, 1H), 8.82 (s, 1H), 8.49 (s, 1H), 3.63 (t, J=6.0 Hz, 2H), 2.63 (t, J=6.0 Hz, 2H), 1.87 (m, 2H), 1.66 (m, 2H). $^{13}$C-NMR (150 MHz, DMSO-d6) δ: 159.06, 50.92, 25.76, 22.01, 17.22.

MS m/z: 115 (M+H)+.

Step 4a: Methyl 2-(2-methoxy-2-oxoethyl)-5,6,7,8-tetrahydro-2H-[1,2,4]oxadiazolo[2,3-a]pyridine-2-carboxylate To a solution of 2-iminopiperidin-1-ol hydrochloride in chloroform was added triethylamine. The mixture was stirred for 5 min. at room temperature, then cooled to 0° C. and 1.2 eq. of dimethyl acetylenedicarboxylate were added dropwise under stirring. The cooling bath was removed and the mixture was stirred at room temperature for one hour. The solvent was removed under reduced pressure and the solution was partitioned between ethyl acetate and half saturated aq. ammonium chloride. The aqueous phase was further extracted with ethyl acetate. The combined organic phases were dried over sodium sulfate and filtered through silica gel. The solvent was removed under vacuum to afford methyl 2-(2-methoxy-2-oxoethyl)-5,6,7,8-tetrahydro-2H-[1,2,4]oxadiazolo[2,3-a]pyridine-2-carboxylate as a light yellow oil.

$^1$H-NMR (400 MHz, CDCl$_3$) δ: 3.82 (s, 3H), 3.70 (s, 3H), 3.51 (m, 1H), 3.36 (m, 1H), 3.31 (d, J=16.6 Hz, 1H), 2.98 (d, J=16.6 Hz, 1H), 2.53 (m, 2H), 1.94 (m, 2H), 1.74 (m, 2H). $^{13}$C-NMR (100 MHz, CDCl$_3$) δ: 169.15, 168.88, 164.97, 103.27, 55.71, 52.97, 51.84, 42.26, 26.06, 23.49, 22.83.

MS m/z: 257 (M+H)$^+$.

Step 5a: Methyl 3-hydroxy-4-oxo-6,7,8,9-tetrahydro-4H-pyrido[1,2-a]pyrimidine-2-carboxylate A solution of methyl 2-(2-methoxy-2-oxoethyl)-5,6,7,8-tetrahydro-2H-[1,2,4]oxadiazolo[2,3-a]pyridine-2-carboxylate in anhydrous o-xylene was placed in a double necked round bottom flask. The flask was equipped was a thermometer and closed with a septum. The mixture was heated to 148-150° C. for 5 h. The heating bath was removed and the mixture was left standing at room temperature for 16 h. To the mixture containing a precipitate was added diethyl ether. After 5 min. the precipitate was filtered off, washed with diethyl ether and dried under vacuum. Product methyl 3-hydroxy-4-oxo-6,7,8,9-tetrahydro-4H-pyrido[1,2-a]pyrimidine-2-carboxylate was obtained as a pale brown solid.

1H-NMR (400 MHz, DMSO-d6) δ: 10.03 (s, 1H), 3.86 (t, J=6.0 Hz, 2H), 3.80 (s, 3H), 2.75 (t, J=6.8 Hz, 2H), 1.90-1.70 (m, 4H). $^{13}$C-NMR (150 MHz, DMSO-d6) δ: 165.81, 158.65, 148.60, 143.10, 127.07, 51.98, 42.87, 30.32, 20.91, 18.40.

MS m/z: 225 (M+H)+.

The following procedure is an alternative route for the synthesis of methyl 3-hydroxy-4-oxo-6,7,8,9-tetrahydro-4H-pyrido[1,2-a]pyrimidine-2-carboxylate

Step 1b: Dimethyl 2-(benzyloxy)-3-oxosuccinate

A solution of methyl(benzyloxy)acetate (1 eq) and dimethyl oxalate (1.2 eq) in dry THF was cooled to −78° C. and LDA (2M in THF-heptane, 1.2 eq) was added dropwise. After stirring for an hour the cold bath was removed, and stirring was continued for an additional hour. The reaction was quenched at 0° C. by pouring into cold 1N aq HCl, and the aqueous phase was extracted with EtOAc; the organic layer was washed with brine, dried and concentrated to give a crude that was used without further purification.

Step 2b: Methyl 3-(benzyloxy)-4-oxo-6,7,8,9-tetrahydro-4H-pyrido[1,2-a]pyrimidine-2-carboxylate Commercially available 2-iminopiperidine hydrochloride (1.5 eq) was added at room temperature to a solution of oxosuccinate prepared in Step 1 b (1 eq) in MeOH. After dropwise addition of neat DBU (4.5 eq), the reaction mixture was stirred for 2 days. Evaporation of the solvent gave a residue that was taken into EtOAc and washed with 1N HCl and brine; the organic layer was dried on Na$_2$SO$_4$ and the solvent removed. The crude was used without further purification.

An analytical sample of this product was purified by flash chromatography (Petroleum ether/EtOAc 1:2 to 1:5), and has the following spectroscopical data:

$^1$H-NMR (400 MHz, CDCl$_3$) δ: 7.49-7.30 (m, 5H), 5.25 (s, 2H), 4.00 (t, J=6.2 Hz, 2H), 3.86 (s, 3H), 2.94 (t, J=6.6 Hz, 2H), 2.01-1.95 (m, 2H), 1.92-1.87 (m, 2H).

$^{13}$C-NMR (75 MHz, CDCl$_3$) δ: 164.1, 159.3, 154.1, 141.1, 140.6, 136.0, 128.1, 127.8, 127.7, 73.8, 52.2, 42.7, 30.9, 21.0, 18.4.

MS m/z: 315 (M+H)$^+$.

Step 3b: Methyl 3-hydroxy-4-oxo-6,7,8,9-tetrahydro-4H-pyrido[1,2-a]pyrimidine-2-carboxylate Intermediate methyl 3-(benzyloxy)-4-oxo-6,7,8,9-tetrahydro-4H-pyrido[1,2a]pyrimidine-2-carboxylate prepared in Step 2b was dissolved in MeOH and catalytic 10% Pd/C was added at room temperature. The mixture was stirred under H$_2$ atmosphere for 3.5 hours. Filtration of the catalyst and evaporation of methanol gave a residue to which diethyl ether was added; filtration afforded methyl 3-hydroxy-4-oxo-6,7,8,9-tetrahydro-4H-pyrido[1,2-a]pyrimidine-2-carboxylate as a pale brown solid with the spectroscopical properties identical to the compound described in Step 5a.

Step 6: N-(4-Fluorobenzyl)-3-hydroxy-4-oxo-6,7,8,9-tetrahydro-4H-pyrido[1,2-a]pyrimidine-2-carboxamide A solution of methyl 3-hydroxy-4-oxo-6,7,8,9-tetrahydro-4H-pyrido[1,2-a]pyrimidine-2-carboxylate obtained in Step 3b or Step 5a and 4-fluoro-benzylamine (2 eq.) in methanol was stirred and heated to 65° C. for 22 h. The solvent was removed under reduced pressure and the title product was obtained by preparative RP-HPLC, using water (0.1% TFA) and acetonitrile (0.1% TFA) as eluents (column: C18). The pooled product fractions were lyophilized to afford the title compound as a fluffy white material.

$^1$H-NMR (400 MHz, DMSO-$d_6$) δ: 12.12 (s, 1H), 9.35 (m, 1H), 7.36 (m, 2H), 7.15 (m, 2H), 4.44 (m, 2H), 3.84 (t, J=6.4 Hz, 2H), 2.80 (t, J=6.8 Hz, 2H), 1.90-1.73 (m, 4H). MS m/z: 318 (M+H)$^+$.

Example 2

N-(4-Fluorobenzyl)-3-hydroxy-9-morpholin-4-yl-4-oxo-6,7,8,9-tetrahydro-4H-pyrido[1,2-a]pyrimidine-2-carboxamide hydrochloride

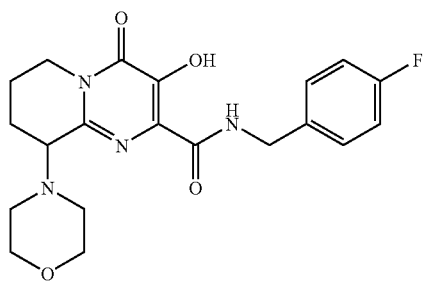

Step 1: Methyl 3-(benzoyloxy)-4-oxo-6,7,8,9-tetrahydro-4H-pyrido[1,2-a]pyrimidine-2-carboxylate To a solution of methyl 3-hydroxy-4-oxo-6,7,8,9-tetrahydro-4H-pyrido[1,2-a]pyrimidine-2-carboxylate (obtained following Example 1) in pyridine was added benzoic anhydride (1.55 eq.). The mixture was stirred at room temperature for 16 h. The solvent was removed under reduced pressure and the residue was partitioned between ethyl acetate and 0.5 M aq. HCl. The aqueous phase was extracted with ethyl acetate and the combined organic phases were washed with 0.5 M aq. HCl, water and brine. The organic phase was dried over sodium sulfate, filtered and concentrated to dryness under vacuum. Title compound was obtained after flash chromatography (eluent petroleum ether/ethyl acetate, 1:2) as a colorless solid.

$^1$H-NMR (400 MHz, DMSO-$d_6$) δ: 8.07 (m, 2H), 7.78 (m, 1H), 7.62 (m, 2H), 3.86 (t, J=6.0 Hz, 2H), 3.74 (s, 3H), 2.92 (t, J=6.4 Hz, 2H), 1.93-1.81 (m, 4H). MS m/z: 329 (M+H)$^+$.

Step 2: Methyl 3-(benzoyloxy)-9-bromo-4-oxo-6,7,8,9-tetrahydro-4H-pyrido[1,2-a]pyrimidine-2-carboxylate A mixture of methyl 3-(benzoyloxy)-4-oxo-6,7,8,9-tetrahydro-4H-pyrido[1,2-a]pyrimidine-2-carboxylate,
N-bromo-succinimide (1.2 eq.) and dibenzoylperoxide (70%, 0.13 eq.) in carbon tetrachloride was stirred under reflux for one hour. The mixture was cooled to room temperature, the succinimide was filtered off and the solvent was removed under reduced pressure. Methyl 3-(benzoyloxy)-9-bromo-4-oxo-6,7,8,9-tetrahydro-4H-pyrido[1,2-a]pyrimidine-2-carboxylate was obtained after flash chromatography (eluent petroleum ether/ethyl acetate, 1:1) as a pale yellow oil.

$^1$H-NMR (400 MHz, DMSO-$d_6$) δ: 8.08 (m, 2H), 7.79 (m, 1H), 7.63 (m, 2H), 5.58 (m, 1H), 4.24 (m, 1H), 3.77 (s, 3H), 3.72 (m, 1H), 2.43-2.35 (m, 1H), 2.30-2.05 (m, 3H). MS m/z: 409/407 (M+H)$^+$.

Step 3: N-(4-Fluorobenzyl)-3-hydroxy-9-morpholin-4-yl-4-oxo-6,7,8,9-tetrahydro-4H-pyrido[1,2-a]pyrimidine-2-carboxamide To a solution of methyl 3-(benzoyloxy)-9-bromo-4-oxo-6,7,8,9-tetrahydro-4H-pyrido[1,2-a]pyrimidine-2-carboxylate in DMF was added morpholine (3 eq.) and the mixture was stirred at room temperature for 1 h. The solvent was removed under reduced pressure and the residue was triturated with diethyl ether. The crude material was dissolved in methanol, 4-fluoro-benzylamine (3 eq.) was added and the mixture was stirred for 1.5 h at 65° C. The solvent was removed under reduced pressure and the product was purified by preparative RP-HPLC, using water (0.1% TFA) and acetonitrile (0.1% TFA) as eluents (column: C18). The pooled product fractions were lyophilized and redissolved in 1N HCl. The solvent was removed under reduced pressure and the residue was lyophilized from water/acetonitrile to afford the hydrochloride salt of N-(4-fluorobenzyl)-3-hydroxy-9-morpholin-4-yl-4-oxo-6,7,8,9-tetrahydro-4H-pyrido[1,2-a]pyrimidine-2-carboxamide as a slightly pink fluffy material.

$^1$H-NMR (400 MHz, DMSO-$d_6$) δ: 12.34 (s, 1H), 10.99 (s, 1H), 10.47 (s, 1H), 7.44 (m, 2H), 7.16 (m, 2H), 4.85 (m, 1H), 4.60-4.40 (m, 3H), 4.10-3.85 (m, 4H), 3.60-3.05 (m, 5H obscured by water signal), 2.35-2.15 (m, 2H), 2.03-1.80 (m, 2H). MS m/z: 403 (M+H)$^+$.

Example 3

(+/−)-9-[[(Dimethylamino)sulfonyl](methyl)amino]-N-(4-fluorobenzyl)-3-hydroxy-4-oxo-6,7,8,9-tetrahydro-4H-pyrido[1,2-a]pyrimidine-2-carboxamide C-3

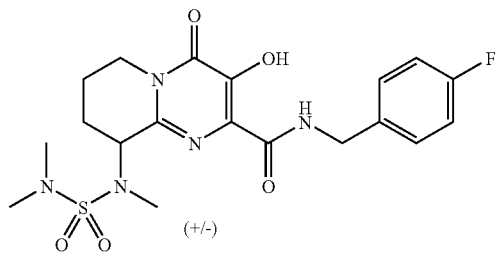

Step 1: Methyl 9-[benzyl(methyl)amino]-3-hydroxy-4-oxo-6,7,8,9-tetrahydro-4H-pyrido[1,2-a]pyrimidine-2-carboxylate hydrochloride To a stirred solution of the bromo derivative methyl 3-(benzoyloxy)-9-bromo-4-oxo-6,7,8,9-tetrahydro-4H-pyrido[1,2- a]pyrimidine-2-carboxylate (obtained in Example 2, Step 2) in anhydrous dimethylformamide was added N-benzyl-N-methylamine (3 eq.). The mixture was stirred for 1.5 h at room temperature before diethyl ether and 2 M HCl in diethyl ether were added. The mixture was stirred for 5 min., the formed precipitate was filtered off and washed with diethyl ether. The precipitate was dissolved in anhydrous methanol and the solution was concentrated to dryness under reduced pressure. The title crude product obtained as a pale yellow oil, which contained an excess of N-benzyl-N-methylamine hydrochloride, was used without further purification.

MS m/z: 344 (M+H)$^+$.

Step 2: Methyl 3-hydroxy-9-(methylamino)-4-oxo-6,7,8,9-tetrahydro-4H-pyrido[1,2-a]pyrimidine-2-carboxylate A solution of crude obtained in Step 1 in methanol, containing palladium on charcoal (10% w/w) was stirred under hydrogen at atmospheric pressure for 3 h. The catalyst was filtered off and the solution was concentrated to dryness under reduced pressure. The residue was triturated with diethyl ether, filtered and dried under high vacuum to afford the crude product as a yellow solid, which was used in the next step without further purification.

MS m/z: 254 (M+H)+.

Step 3: N-(4-Fluorobenzyl)-3-hydroxy-9-(methylamino)-4-oxo-6,7,8,9-tetrahydro-4H-pyrido[1,2-a]pyrimidine-2-carboxamide To a solution of the crude obtained in Step 2 in dry methanol were added an excess of triethylamine. The solvent was removed under reduced pressure and then under high vacuum. The oily residue was dissolved in anhydrous methanol and 4-fluoro-benzylamine was added (3.1 eq. th.). The mixture was stirred and heated to 60° C. overnight. After cooling to room temperature the solvent was removed under reduced pressure. The residue was triturated with diethyl ether and left under high vacuum for 15 min. The title crude product was obtained as a yellow solid, which contained an excess of 4-fluoro-benzylamine (ca. 3.5 eq.) and was used without further purification.

MS m/z: 347 (M+H)$^+$.

Step 4: (+/−)-9-[[(Dimethylamino)sulfonyl](methyl)amino]-N-(4-fluorobenzyl)-3-hydroxy-4-oxo-6,7,8,9-tetrahydro-4H-pyrido[1,2-a]pyrimidine-2-carboxamide To a solution of crude compound obtained in Step 3 in a 2:1 mixture of tetrahydrofuran and 2 M aq. sodium hydroxide was added N,N-dimethylsulfamoyl chloride (4.6 eq.). The mixture was stirred at room temperature for 16 h. The mixture was concentrated under reduced pressure and the product was isolated by preparative RP-HPLC, using water (0.1% TFA) and acetonitrile (0.1% TFA) as eluents (column: C18). The pooled product fractions were lyophilized to afford the title compound as a fluffy, slightly pink material.

$^1$H-NMR (300 MHz, CDCl$_3$) δ: 11.95 (s, 1H), 9.13 (m, 1H), 7.38 (m, 2H), 7.04 (m, 2H), 4.98 (m, 1H), 4.56 (m, 2H), 4.36 (m, 1H), 3.62 (m, 1H), 2.84 (s, 6H), 2.57 (s, 3H), 2.38-1.85 (m, 4H). $^{13}$C-NMR (100 MHz, CDCl$_3$) δ: 167.53, 162.55, 160.11, 157.74, 145.76, 144.11, 132.70, 128.89, 128.81, 124.82, 114.60, 114.39, 58.06, 42.93, 41.53, 37.00, 29.03, 23.89, 20.09.

MS m/z: 454 (M+H)$^+$.

Example 4

(+/−)-N$^1$-(2-{[(4-Fluorobenzyl)amino]carbonyl}-3-hydroxy-4-oxo-6,7,8,9-tetrahydro-4H-pyrido[1,2-a]pyrimidin-9-yl)-N$^1$,N$^2$,N$^2$-trimethylethanediamide

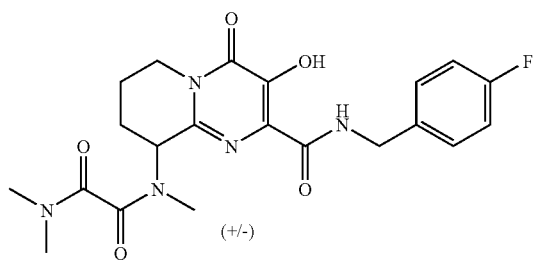

Step 1: (+/−)-N$^1$-(2-{[(4-Fluorobenzyl)amino]carbonyl}-3-hydroxy-4-oxo-6,7,8,9-tetrahydro-4H-pyrido[1,2-a]pyrimidin-9-yl)-N$^1$,N$^2$,N$^2$-trimethylethanediamide To a stirred solution of crude N-(4-fluorobenzyl)-3-hydroxy-9-(methylamino)-4-oxo-6,7,8,9-tetrahydro-4H-pyrido[1,2-a]pyrimidine-2-carboxamide (synthesized as described in Example 3, Step 3) in dichloromethane were added 6 eq. of triethylamine and 6 eq. of methyl chlorooxoacetate. The mixture was stirred at room temperature for 2 h, the solvent was removed under reduced pressure and the residue was dissolved in a solution of dimethylamine (2 M) in tetrahydrofuran. The mixture was stirred at 57° C. overnight. After cooling to room temperature, the solvent was removed under reduced pressure and the product was isolated by preparative RP-HPLC, using water (0.1% TFA) and acetonitrile (0.1% TFA) as eluents (column: C18). The pooled product fractions were lyophilized to afford the title compound as a fluffy, slightly pink material. The product was a mixture of rotamers by NMR.

$^1$H-NMR (400 MHz, DMSO-d6) δ: 12.05 (s, 0.2H), 11.89 (s, 0.8H), 9.21 (m, 0.8H), 8.74 (m, 0.2H), 7.40-7.28 (m, 2H), 7.20-7.10 (m, 2H), 5.17 (m, 0.8H), 4.63-4.35 (m, 2.2H), 4.13-4.00 (m, 1H), 3.65-3.53 (m, in part overlaid by water signal), 2.95-2.75 (m, 9H), 2.15-1.80 (m, 4H). $^{13}$C-NMR (100 MHz, DMSO-d6) δ: 167.87, 167.73, 165.92, 165.46, 164.51, 164.30, 162.42, 160.01, 157.50, 157.41, 146.27, 146.18, 145.76, 145.49, 134.44, 129.43, 129.35, 129.08, 129.00, 125.17, 125.05, 115.07, 114.85, 57.47, 53.60, 43.14, 41.37, 36.49, 35.95, 32.92, 32.64, 32.36, 28.19, 23.88, 22.12, 19.67, 19.35.

MS m/z: 446 (M+H)$^+$.

Example 5

(+)-N[1]-(2-{[(4-Fluorobenzyl)amino]carbonyl}-3-hydroxy-4-oxo-6,7,8,9-tetrahydro-4H-pyrido[1,2-a]pyrimidin-9-yl)-N[1],N[2],N[2]-trimethylethanediamide

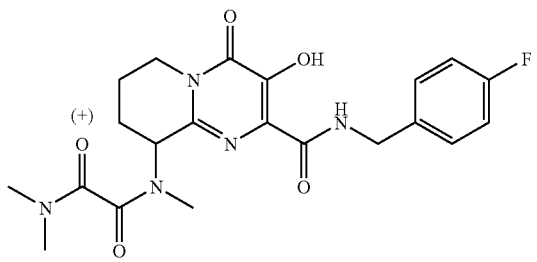

Step 1: (+)3-Hydroxy-2-(methoxycarbonyl)-N-methyl-4-oxo-N-[(1S)-1-phenylethyl]-6,7,8,9-tetrahydro-4H-pyrido[1,2-a]pyrimidin-9-ammonium trifluoroacetate To a 7:3 mixture (v/v) of methanol and water at −30° C., containing (1S)-1-phenylethylamine (4.5 eq.) was added bromo derivative methyl 3-(benzoyloxy)-9-bromo-4-oxo-6,7,8,9-tetrahydro-4H-pyrido[1,2-a]pyrimidine-2-carboxylate (synthesized as reported in Example 2, Step 2) (1.0 eq.). The mixture was stirred vigorously for 1.5 h at −30° C. The cooling bath was removed and stirring was continued for 1 h at room temperature. The pH was adjusted to ca. 5 with acetic acid before 37% aqueous formaldehyde (11.5 eq.) and sodium cyanoborohydride (3.25 eq.) were added. After stirring at room temperature for 20 min. the volume was reduced to ca. ¼ under reduced pressure. A formed white precipitate was filtered off and the filtrate was acidified to pH 2-3 with trifluoroacetic acid. The solution was applied on cation-exchange resin cartridges (Varian MEGA BOND ELUTE SCX), the cartridges washed with methanol and the crude product was eluted with 2 M ammonia in methanol. The pooled eluents were concentrated to dryness under reduced pressure and the oily residue was dissolved in methanol and neutralized with trifluoroacetic acid. After removal of the solvent an oily residue was obtained. The resulting diastereoisomers in 1:3 ratio were separated by preparative RP-HPLC-purification (column: C18) eluents water (0.1% TFA), acetonitrile (0.1% TFA). The major diastereoisomer was eluted as second peak and after lyophilization the title compound was obtained as a slightly pink solid.

$^1$H-NMR (500 MHz, pyridine-$d_5$) δ: 7.53 (m, 2H), 7.39 (m, 2H), 7.29 (m, 1H), 4.45 (m, 1H), 4.38 (m, 1H), 4.14 (m, 1H), 3.91 (s, 3H), 3.80 (m, 1H), 2.13 (s, 3H), 1.95-1.82 (m, 3H), 1.70-1.60 (m, 1H), 1.49 (d, J=6.4 Hz, 3H).

MS m/z: 358 (M+H)$^+$.

Step 2: (−)-3-Hydroxy-2-(methoxycarbonyl)-N-methyl-4-oxo-6,7,8,9-tetrahydro-4H-pyrido[1,2-a]pyrimidin-9-ammonium trifluoroacetate A solution of (+)3-hydroxy-2-(methoxycarbonyl)-N-methyl-4-oxo-N-[(1S)-1-phenylethyl]-6,7,8,9-tetrahydro-4H-pyrido[1,2-a]pyrimidin-9-ammonium trifluoroacetate in methanol, containing palladium on charcoal (10%, w/w) was stirred under hydrogen at atmospheric pressure for 1.5 h. The catalyst was filtered off and the solution was concentrated to dryness under reduced pressure to afford the title compound as a slightly pink oil.

$^1$H-NMR (400 MHz, CD$_3$OD) δ: 4.41 (m, 1H), 4.14 (m, 1H), 3.99 (s, 3H), 3.91 (m, 1H), 2.86 (s, 3H), 2.50 (m, 1H), 2.26 (m, 1H), 2.08 (m, 1H), 1.86 (m, 1H).

MS m/z: 254 (M+H)$^+$.

Step 3: (+)-N[1]-(2-{[(4-Fluorobenzyl)amino]carbonyl}-3-hydroxy-4-oxo-6,7,8,9-tetrahydro-4H-pyrido[1,2-a]pyrimidin-9-yl)-N[1],N[2],N[2]-trimethylethanediamide A solution of (−)-3-Hydroxy-2-(methoxycarbonyl)-N-methyl-4-oxo-6,7,8,9-tetrahydro-4H-pyrido[1,2-a]pyrimidin-9-ammonium trifluoroacetate, p-fluoro-benzylamine (2.2 eq.) and triethylamine (1.3 eq.) in methanol was stirred and heated to 65° C. for 3 h. The solvent was removed under vacuum and the residue was dissolved in anhydrous dichloromethane. Methyl chlorooxoacetate (5 eq.) and triethylamine (5 eq.) were added and the mixture was stirred at room temperature for 50 min. The solvent was removed under reduced pressure and the residue was dissolved in a 2 M solution of dimethylamine in tetrahydrofuran. The mixture was stirred at 57° C. overnight. After cooling to room temperature the solvent was removed under reduced pressure and the product was isolated by preparative RP-HPLC, using water (0.1% TFA) and acetonitrile (0.1% TFA) as eluents (column: C18). The pooled product fractions were lyophilized to afford the title product as a fluffy white material (ee 94.4%).

The compound was dissolved in ethylacetate/heptane (3:2.5 (v/v) mixture) and left standing at room temperature for four days. The supernatant from the formed precipitate was taken off, concentrated under reduced pressure and the residue was lyophilized from water/acetonitrile to afford enantiopure title product e.e. 100% (e.e. determined by Chiral HPLC Chiralpak AS, mobile phase 0.2% TFA n-Hex/IPA) with spectroscopical properties identical to the compound described in Example 4, Step 1.

$[α]^{20}_D$=+36.5±2.5° (C=0.63 in ethanol).

Example 6

(−)-N[1]-(2-{[(4-Fluorobenzyl)amino]carbonyl}-3-hydroxy-4-oxo-6,7,8,9-tetrahydro-4H-pyrido[1,2-a]pyrimidin-9-yl)-N[1],N[2],N[2]-trimethylethanediamide

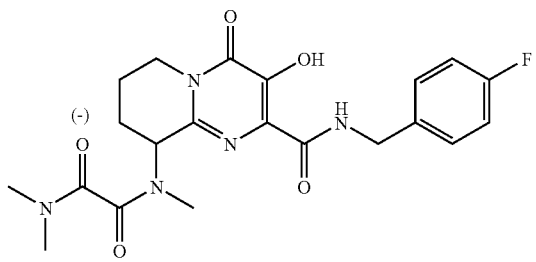

Step 1: (−)-3-Hydroxy-2-(methoxycarbonyl)-N-methyl-4-oxo-N-[(1R)-1-phenylethyl]-6,7,8,9-tetrahydro-4H-pyrido[1,2-a]pyrimidin-9-ammonium trifluoroacetate Title compound was obtained using (1R)-1-phenylethylamine and following the procedure describe in Example 5, Step 1.

$^1$H-NMR (400 MHz, pyridine-d$_5$) δ: 7.55 (m, 2H), 7.40 (m, 2H), 7.29 (m, 1H), 4.47 (m, 1H), 4.39 (m, 1H), 4.15 (m, 1H), 3.92 (s, 3H), 3.80 (m, 1H), 2.14 (s, 3H), 1.95-1.82 (m, 3H), 1.72-1.60 (m, 1H), 1.50 (d, J=6.4 Hz, 3H). MS mm/z: 358 (M+H)$^+$. [α]$^{20}_D$=−15.1° (C=0.55 in methanol).

Step 2: (+)-3-Hydroxy-2-(methoxycarbonyl)-N-methyl-4-oxo-6,7,8,9-tetrahydro-4H-pyrido[1,2-a]pyrimidin-9-ammonium trifluoroacetate Title compound was synthesized following the procedure described in Example 5, Step 2, using as starting material the compound synthesized in the previous Step 1. It showed identical spectroscopical properties, except for the optical rotation.

[α]$^{20}_D$=+18.7° (C=0.41 in methanol).

Step 3: (−)-N$^1$-(2-{[(4-Fluorobenzyl)amino]carbonyl}-3-hydroxy-4-oxo-6,7,8,9-tetrahydro-4H-pyrido[1,2-a]pyrimidin-9-yl)-N$^1$,N$^2$,N$^2$-trimethylethanediamide The compound was synthesized following the same procedure described in Example 5, Step 3 using the compound prepared in the previous Step 2. The title compound (e.e. 93%) was dissolved in ethanol and the formed precipitate was filtered off. The obtained solution was concentrated to dryness under vacuum and the residue was redissolved in ethanol. The solution was left standing at room temperature for one day. The supernatant from the formed precipitate was taken off, concentrated under reduced pressure and the residue was lyophilized from water/acetonitrile to afford 15b with an enantiomeric excess of 99.6% (e.e. determined by Chiral HPLC Chiralpak AS, mobile phase 0.2% TFA n-Hex/IPA) with spectroscopical properties identical to the compound described in Example 4, Step 1.

[α]$^{20}_D$=−36.5±2.5°, (C=0.50 in ethanol).

Example 7

(−)-9-[[(Dimethylamino)sulfonyl](methyl)amino]-N-(4-fluorobenzyl)-3-hydroxy-4-oxo-6,7,8,9-tetrahydro-4H-pyrido[1,2-a]pyrimidine-2-carboxamide

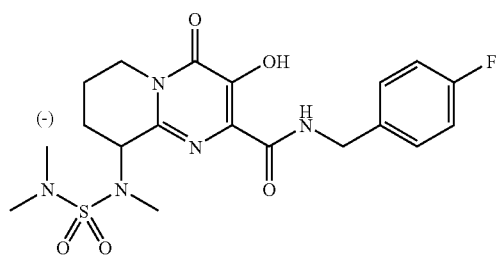

Step 1: (−)-9-[[(Dimethylamino)sulfonyl](methyl)amino]-N-(4-fluorobenzyl)-3-hydroxy-4-oxo-6,7,8,9-tetrahydro-4H-pyrido[1,2-a]pyrimidine-2-carboxamide To a solution of the amine synthesized in Example 5, Step 2 in methanol were added 4-fluoro-benzylamine (3 eq.) and triethylamine (2 eq.). The mixture was heated to 65° C. and stirred overnight. The solvent was removed under reduced pressure and the residue dissolved in dichloromethane. N,N-dimethylsulfamoyl chloride (3 eq.) and triethylamine (3 eq.) were added and the mixture was stirred for 4 h. The mixture was partitioned between ethylacetate and 0.1 M HCl. The aqueous phase was extracted with ethylacetate and the combined organic phases were dried over sodium sulfate, filtered and concentrated to dryness under reduced pressure. The product was purified by preparative RP-HPLC, using water (0.1% TFA) and acetonitrile (0.1% TFA) as eluents (column: C18). The pooled product fractions were lyophilized to afford the title product as a fluffy white material (ee 90.7%). The compound was dissolved in ethanol and left standing at room temperature for three days. The supernatant was taken off and concentrated to dryness under reduced pressure. The residue was redissolved in ethanol and the solution was left standing at room temperature for one day. The supernatant was taken off, concentrated under reduced pressure and the residue lyophilized from water/acetonitrile to afford the title product with an enantiomeric excess of 99.4% (e.e. determined by Chiral HPLC Chiralpak AD, mobile phase 0.2% TFA n-Hex/IPA) with spectroscopical properties identical to the compound synthesized in Example 3, Step 4 except for the optical rotation.

[α]$^{20}_D$=−33±1°, (C=0.56 in ethanol).

Example 8

(+)-9-[[(Dimethylamino)sulfonyl](methyl)amino]-N-(4-fluorobenzyl)-3-hydroxy-4-oxo-6,7,8,9-tetrahydro-4H-pyrido[1,2-a]pyrimidine-2-carboxamide

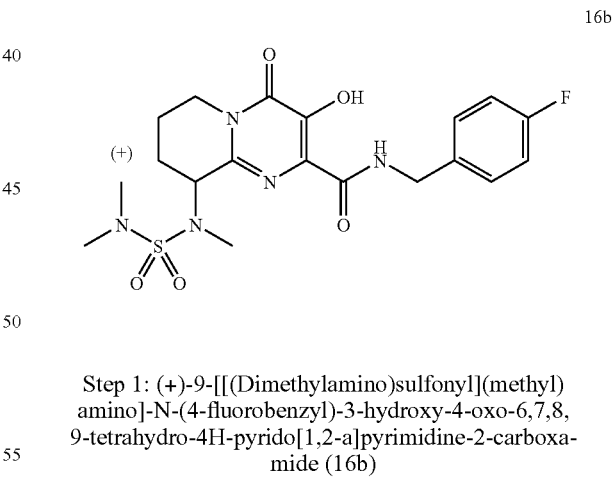

Step 1: (+)-9-[[(Dimethylamino)sulfonyl](methyl)amino]-N-(4-fluorobenzyl)-3-hydroxy-4-oxo-6,7,8,9-tetrahydro-4H-pyrido[1,2-a]pyrimidine-2-carboxamide (16b)

The title compound was synthesized using as starting material the amine prepared in Example 6, Step 2 and following the procedure describe in Example 7, Step 1. The compound was obtained directly with the enantiomeric excess reported below and with spectroscopical properties identical to the compound synthesized in Example 3, Step 4 except for the optical rotation. Enantiomeric excess was determined by Chiral HPLC Chiralpak AD, mobile phase 0.2% TFA n-Hex/IPA.

[α]$^{20}_D$=+33±1°, (C=0.69 in ethanol, ee 96.6%).

Example 9

N-(4-Fluorobenzyl)-3-hydroxy-4-oxo-4,6,7,8-tetrahydropyrrolo[1,2-a]pyrimidine-2-carboxamide

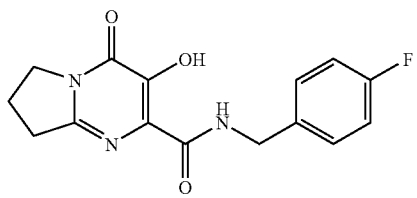

Step 1: tert-butyl benzyloxy(3-cyanopropyl)carbamate (Bergeron, R. J., McManis, J. S., Tetrahedron 45 (16), 4939-4944 (1989))

The title compound was prepared according to the literature as described in EXAMPLE 1—Step 1a, from 3-chloropropyonitrile.

$^1$H-NMR (CDCl$_3$, 400 MHz, 300K) δ: 7.39-7-30 (m, 5H), 4.82 (s, 2H), 3.50 (t, J=6.5 Hz, 2H), 2.31 (t, J=7.2 Hz, 2H), 1.90-1.82 (m, 2H), 1.50 (s, 9H).

$^{13}$C NMR (CDCl$_3$, 75 MHz, 300 K) δ 156.3, 135.3, 129.5, 128.7, 128.5, 119.1, 82.0, 77.0, 48.1, 28.3, 23.5, 14.9.

Step 2: 1-(benzyloxy)pyrrolidin-2-imine hydrochloride

The title compound was prepared from tert-butyl benzyloxy(3-cyanopropyl)carbamate as described in EXAMPLE 1—Step 2a.

$^1$H-NMR (DMSO-d$_6$, 400 MHz, 300K) δ: 9.76 (s, 1H), 9.23 (s, 1H), 7.59-7.53 (m, 2H), 7.45-7.40 (m, 3H), 5.07 (s, 2H), 3.77 (t, J=7.1 Hz, 2H), 2.78 (t, J=7.7 Hz, 2H), 2.06-1.97 (m, 2H).

$^{13}$C NMR (DMSO-d6, 75 MHz, 300K) δ 163.8, 133.7, 129.9, 129.3, 128.5, 75.9, 49.9, 26.8, 16.2.

MS: m/z (%): 191 ((M+H)$^+$, 100).

Step 3: 2-iminopyrrolidin-1-ol hydrochloride

The title compound was obtained from 1-(benzyloxy)pyrrolidin-2-imine hydrochloride as described for EXAMPLE 1—Step 3a.

$^1$H-NMR (DMSO-d$_6$, 300 MHz, 300K) δ: 11.89 (s, 1H), 9.14 (s, 1H), 8.64 (s, 1H), 3.77 (t, J=7.3 Hz, 2H), 2.79 (t, J=7.9 Hz, 2H), 2.11-1.98 (m, 2H).

$^{13}$C NMR (DMSO-d6, 75 MHz, 300 K) δ 161.3, 52.9, 26.8, 16.1.

MS: m/z (%): 101 ((M+H)$^+$, 100), 83 (—H$_2$O, 60).

Step 4: Methyl 3-hydroxy-4-oxo-4,6,7,8-tetrahydropyrrolo[1,2-a]pyrimidine-2-carboxylate To a solution of 2-iminopyrrolidin-1-ol hydrochloride in chloroform, triethylamine (1.5 eq) was added. The mixture was stirred for 5 min. at room temperature, then cooled to −30° C. before the addition, dropwise under stirring, of dimethylacetylenedicarboxylate (1.1 eq) in chloroform. After 1 h the solvent was removed under reduced pressure. To the resulting crude, 2 mL of anhydrous o-xylene was added and the mixture was heated under vigorous stirring at 150° C. (oil bath temperature) for 2 h, then the solvent was evaporated under reduced pressure. The residue was treated with MeOH and filtered, the filtrate was evaporated. The analytical sample was obtained by purification by preparative HPLC (Symmetry Column C18, 5 μm, 19×300 mm, gradient of CH$_3$CN/H$_2$O+0.01% TFA).

$^1$H-NMR (DMSO-d$_6$, 400 MHz, 300K) δ: 10.19 (s, 1H), 3.99 (t, J=7.3 Hz, 2H), 3.80 (s, 3H), 2.92 (t, J=7.9 Hz, 2H), 2.20-2.10 (m, 2H).

$^{13}$C NMR (DMSO-d6, 75 MHz, 300K) δ 166.4, 157.1, 153.6, 144.6, 128.3, 52.1, 46.8, 30.9, 19.5.

MS: m/z (%): 211 ((M+H)$^+$, 100), 201 (100).

Step 5: Methyl 3-(benzoyloxy)-4-oxo-6,7,8,9-tetrahydropyrrolo[1,2-a]pyrimidine-2-carboxylate (A) and 4-oxo-4,6,7,8-tetrahydropyrrolo[1,2-a]pyrimidin-3-yl benzoate (B)

To a solution of crude methyl 3-hydroxy-4-oxo-4,6,7,8-tetrahydropyrrolo[1,2-a]pyrimidine-2-carboxylate in pyridine benzoic anhydride (1.2 eq) was added and the mixture was stirred at room temperature overnight. The solvent was removed under reduced pressure and the residue was partitioned between ethyl acetate and NaHCO$_3$ saturated solution. The organic phase is then washed with 1N HCl, brine, dried over Na$_2$SO$_4$, filtered and concentrated to dryness under vacuum. After flash chromatography of the oily residue on silica gel (eluent petroleum ether/EtOAc 1:3, then EtOAc) a solid was obtained, that by $^1$H NMR and mass proved to be a 2:1 mixture of product A and product B. Crystallization from EtOAc enriched the mixture to 6:1 A:B. Analytical samples of the two were obtained by prep.HPLC of the mixture (Symmetry Column C18, 5 μm, 19×300 mm, gradient of CH$_3$CN/H$_2$O+0.01% TFA) and subsequent crystallization from EtOAc.

A: $^1$H-NMR (DMSO-d$_6$, 400 MHz, 300K) δ: 8.70 (d, J=7.2 Hz, 2H), 8.29 (t, J=7.4 Hz, 1H), 8.18-8.10 (m, 2H), 4.64 (t, J=7.4 Hz, 2H), 4.31 (s, 3H), 3.64 (t, J=8.1 Hz, 2H), 2.87-2.78 (m, 2H).

$^{13}$C NMR (DMSO-d6, 75 MHz, 300K) δ 163.1, 163.1, 162.8, 156.0, 142.4, 136.0, 134.4, 129.8, 129.1, 127.8, 52.7, 47.6, 31.9, 19.2.

MS: m/z (%): 315 ((M+H)+, 100), 201 (25).

m.p. 170.3-171.3° C. (EtOAc).

B: $^1$H-NMR (DMSO-d$_6$, 400 MHz, 300K) δ: 8.69 (d, J=7.4 Hz, 2H), 8.42 (s, 1H), 8.27 (t, J=7.4 Hz, 1H), 8.16-8.09 (m, 2H), 4.63 (t, J=7.4 Hz, 2H), 3.61 (t, J=8.1 Hz, 2H), 2.86-2.76 (m, 2H).

$^{13}$C NMR (DMSO-d$_6$, 75 MHz, 300K) δ 163.5, 163.3, 155.5, 144.5, 136.3, 134.2, 129.8, 129.0, 128.0, 47.2, 31.8, 19.4.

Step 6: N-(4-fluorobenzyl)-3-hydroxy-4-oxo-4,6,7,8-tetrahydropyrrolo[1,2-a]pyrimidine-2-carboxamide To a solution of crude mixture of Methyl 3-(benzoyloxy)-4-oxo-6,7,8,9-tetrahydropyrrolo[1,2-a]pyrimidine-2-carboxylate and 4-oxo-4,6,7,8-tetrahydropyrrolo[1,2-a]pyrimidin-3-yl benzoate (ratio 6:1) in dry methanol, 3 eq. of 4-fluoro-benzylamine were added. The mixture was irradiated in a microwave apparatus (140° C., 500 sec). After cooling the solvent was removed under reduced pressure. The product was isolated by preparative RP-HPLC (Symmetry Column C18, 5 μm, 19×300 mm, gradient of CH$_3$CN/H$_2$O+ 0.01% TFA). The pooled product fractions were lyophilized to afford the title compound.

$^1$H-NMR (DMSO-d$_6$, 400 MHz, 300K) δ: 12.74 (bs, 1H), 8.96 (bs, 1H), 7.94-7.89 (m, 2H), 7.66-7.60 (m, 2H), 5.06 (d, J=6.6 Hz, 2H), 4.56 (t, J=7.2 Hz, 2H), 3.47 (t, J=7.9 Hz, 2H), 2.77 (m, partially hidden under H$_2$O).

$^{13}$C NMR (DMSO-d6, 75 MHz, 300 K) δ 168.6, 161.2 (d, J=242 Hz), 156.3, 153.7, 147.0, 134.8 (d, J=3 Hz), 129.5 (d, J=8 Hz), 126.6, 115.0 (d, J=21 Hz), 46.8, 41.4, 31.1, 19.3.

MS: m/z (%): 304 ((M+H)+, 100), 201 (70).

Example 10

8-[[(Dimethylamino)sulfonyl](methyl)amino]-N-(4-fluorobenzyl)-3-hydroxy-4-oxo-4,6,7,8-tetrahydro-pyrrolo[1,2-a]pyrimidine-2-carboxamide

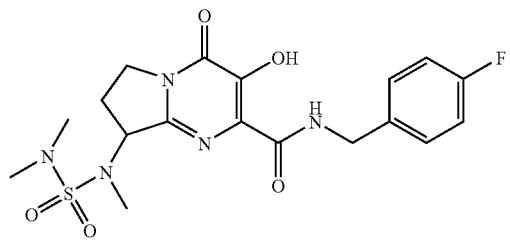

Crude methyl 3-(benzoyloxy)-4-oxo-4,6,7,8-tetrahydro-pyrrolo[1,2-a]pyrimidine-2-carboxylate, obtained as in EXAMPLE 9—Step 5, was reacted as described in EXAMPLE 2-Step 2. After purification by flash chromatography (eluent petroleum ether/ethyl acetate, 65:35) the resulting bromide (MS m/z: 393/395 (M+H)$^+$) was obtained. The bromide was dissolved in anhydrous dimethylformamide and N-benzyl-N-methylamine (3 eq.) was added. The mixture was stirred for 2 h at room temperature and then concentrated to dryness under reduced pressure, to afford crude methyl-benzylamine derivative (MS m/z: 330 (M+H)$^+$). After dissolution in methanol, containing palladium on charcoal (10% w/w), the compound was stirred under hydrogen at atmospheric pressure for 1.5 h. The catalyst was filtered and the solution was concentrated to dryness under reduced pressure to give crude methylamine derivative (MS m/z: 240 (M+H)+), which was dissolved in dry methanol. Triethylamine (2 eq) and 4-fluoro-benzylamine (3 eq) were added. The mixture was stirred and heated to 65° C. overnight. After cooling to room temperature the solvent was removed under reduced pressure. Crude p-fluorobenzylamide (MS m/z: 333 (M+H)$^+$) was dissolved in dry dichloromethane and N,N-dimethylsulfamoyl chloride (3.5 eq.) was added. The mixture was stirred at room temperature for 16 h. The reaction was diluted with DCM and washed with HCl 1N and brine. The organic phase was dried on Na$_2$SO$_4$ and concentrated. The product was isolated by preparative RP-HPLC (Symmetry Column C18, 5 μm, 19×300 mm, gradient of CH$_3$CN/H$_2$O+0.01% TFA). The pooled product fractions were lyophilized to afford the compound as a fluffy, slightly pink material.

$^1$H-NMR (DMSOd$_6$, 400 MHz, 300K) δ: 12.42 (bs, 1H), 8.78 (t, J=6.3 Hz, 1H), 7.42-7.35 (m, 2H), 7.23-7.15 (m, 2H), 5.27 (t, J=9.1 Hz, 1H), 4.51 (ddd, J$_1$=6.3 Hz, J$_2$=14.8 Hz J$_3$=26.8 Hz, 2H), 4.13-4.05 (m, 1H), 3.88-3.72 (m, 1H, partially hidden under water), 2.78 (s, 6H), 2.73 (s, 3H), 2.48-2.38 (m, 1H), 2.35-2.23 (m, 1H).

MS m/z: 440 (M+H)$^+$.

Example 11

(+/−)-N-(2-{[(4-fluorobenzyl)amino]carbonyl}-3-hydroxy-4-oxo-4,6,7,8,9,10-hexahydropyrimido[1,2-a]azepin-10-yl)-N, N',N'-trimethylethanediamide

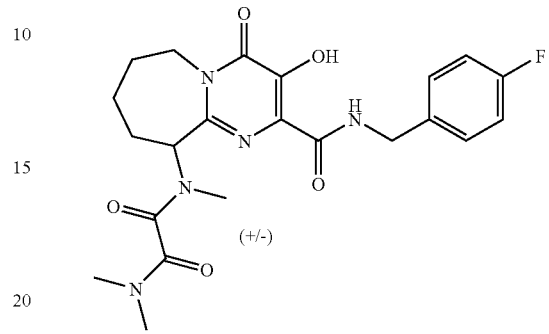

The title compound was prepared according to the synthetic sequence described in EXAMPLE 4, with the following variations:

Step 1: 1-(Benzyloxy)azepan-2-imine

Tert-butyl-(benzyloxy)-(5-cyanopentyl)-carbamate (synthesized following the procedure described in EXAMPLE 1—Step 1a starting from 6-bromohexanenitrile) was dissolved in a saturated solution of HCl in EtOH and the mixture was stirred for 45 minutes. Nitrogen was bubbled into the solution to remove HCl in excess. The solvent was removed under reduced pressure and the residue, dissolved in 1,4-dioxane, was treated with triethylamine to adjust pH at 10. Ethanol was removed and the title compound containing an excess of triethylammonium chloride and ethyl 6-[(benzyloxy)amino]hexanoate was used without further purification. The analytical sample was purified by preparative RP-HPLC, using water (0.1% TFA) and acetonitrile (0.1% TFA) as eluents (column C$_{18}$). The pooled product fractions were lyophilized.

$^1$H-NMR (400 MHz, DMSO-d$_6$, 300K) δ: 9.39 (s, 1H), 8.81 (s, 1H), 7.61-7.52 (m, 2H), 7.48-7.38 (m, 3H), 5.03 (s, 2H), 4.02-3.93 (m, 2H), 2.70-2.59 (m, 2H), 1.69-1.54 (m, 6H).

MS m/z: 219 (M+H)$^+$.

Step 2: (+/−)-N-(2-{[(4-Fluorobenzyl)amino]carbonyl}-3-hydroxy-4-oxo-4-6,7,8,9,10-hexahydropyrimido[1,2-a]azepin-10-yl)-N,N',N'-trimethylethanediamide To a stirred solution of crude N-(4-fluorobenzyl)-3-hydroxy-10-(methylamino)-4-oxo-4,6,7,8,9,10-hexahydropyrimido[1,2-a]azepine-2-carboxamide (synthesized starting from 1-(benzyloxy)azepan-2-imine according to the procedure used in the analogous 6-membered series (EXAMPLE 3—Step 3) in dichloromethane were added 3 eq. of triethylamine, 2 eq of potassium (dimethylamino)(oxo)acetate, 2.2 eq. of 1-(3-dimethylaminopropyl)-3-ethylcarbodiimide hydrochloride and 2.2 eq. of 1-hydroxybenzotriazole. The mixture was stirred at room temperature overnight. The solvent was removed under reduced pressure and the residue was partitioned between ethyl acetate and 1 M aq. HCl. The aqueous phase was extracted with ethyl acetate and the combined organic phases were dried over sodium sulfate, filtered and concentrated to dryness under vacuum. The title product was isolated by preparative RP-HPLC, using water (0.1% TFA) and acetonitrile (0.1% TFA) as eluents (column: C18). The pooled product fractions were lyophilized to afford the title compound as a fluffy, white material. The product is a mixture of rotamers by $^1$H NMR.

$^1$H-NMR (400 MHz, DMSO-$d_6$, 300K) δ: 12.29 (bs, 0.1H), 11.95 (bs, 0.9H), 9.30 (bs, 0.9H), 8.45 (bt, 0.1H), 7.38 (dd, J=8.33, 5.5 Hz, 1.8H), 7.33 (dd, J=8.33, 5.5 Hz, 0.2H), 7.15 (t, J=9.0 Hz, 2H), 5.45-5.25 (m, 0.9H), 4.94 (dd, J=14, 5.7 Hz, 1.0H), 4.84-4.79 (m, 0.1H), 4.57-4.43 (m, 2H), 3.54 (dd, J=14, 11 Hz, 0.9H), 3.28-3.18 (m, 0.1H), 3.05 (s, 0.3H), 2.92 (s, 2.7H), 2.90 (s, 5.4H), 2.81 (s, 0.3H), 2.76 (s, 0.3H), 2.19-1.78 (m, 5H), 1.41-1.27 (m, 1H).

MS m/z: 460 (M+H)$^+$.

Example 12

(−)-N-(2-{[(4-fluorobenzyl)amino]carbonyl}-3-hydroxy-4-oxo-4,6,7,8,9,10-hexahydropyrimido[1,2-a]azepin-10-yl)-N,N',N'-trimethylethanediamide Step 1: Dimethyl (2E)-2-[(azepan-2-ylideneamino)oxy]but-2-enedioate and dimethyl (2Z)-2-[(azepan-2-ylideneamino)oxy]but-2-enedioate To a suspension of azepan-2-one oxime in acetonitrile 1.1 eq. of dimethyl acetylenedicarboxylate were added dropwise under stirring. The mixture was stirred at room temperature for 1 hour. The solvent was removed under reduced pressure to afford a mixture 8/1 of dimethyl (2E)-2-[(azepan-2-ylideneamino)oxy]but-2-enedioate and dimethyl (2Z)-2-[(azepan-2-ylideneamino)oxy]but-2-enedioate as a yellow oil. To better characterize the title compounds a small amount of the crude was purified by preparative RP-HPLC, using water (0.1% TFA) and acetonitrile (0.1% TFA) as eluents (column $C_{1-8}$). The pooled product fractions were lyophilized.

Isomer E: $^1$H-NMR (400 MHz, DMSO-d6, 300K) δ: 7.08 (bs, 1H), 5.63 (s, 1H), 3.77 (s, 3H), 3.59 (s, 3H), 3.19-3.11 (m, 2H), 2.29-2.21 (m, 2H), 1.66-1.42 (m, 6H).

$^{13}$C-NMR (125 MHz, DMSO-$d_6$, 300 K) δ: 166.20, 162.81, 161.90, 161.61, 92.38, 52.42, 50.92, 42.28, 29.84, 29.32, 28.81, 25.40.

MS m/z: 271 (M+H)$^+$.

Isomer Z: $^1$H-NMR (400 MHz, DMSO-d6, 300K): 6.66 (bs, 1H), 5.63 (s, 1H), 3.74 (s, 3H), 3.61 (s, 3H), 3.24-3.16 (m, 2H), 2.20-2.12 (m, 2H), 1.65-1.44 (m, 6H).

$^{13}$C-NMR (125 MHz, DMSO-$d_6$, 300K)$_6$: 165.01, 163.01, 161.45, 154.11, 101.09, 52.32, 51.05, 42.24, 29.93, 29.31, 28.45, 25.14.

MS m/z: 271 (M+H)$^+$.

Step 2: Methyl 3-hydroxy-4-oxo-4,6,7,8,9,10-hexahydropyrimido[1,2-a]azepine-2-carboxylate A mixture of dimethyl (2E)-2-[(azepan-2-ylideneamino)oxy]but-2-enedioate and dimethyl (2Z)-2-[(azepan-2-ylideneamino)oxy]but-2-enedioate in ratio 8/1 was dissolved in o-xylene and refluxed. After 16 h the solvent was removed under reduced pressure and the residue, dissolved in ethyl acetate, was extracted with a saturated solution of NaHCO$_3$ in water. The pH of the aqueous phase was adjusted to about 3 adding 6M HCl aq. and the solution was extracted with dichloromethane. The organic phase was dried over sodium sulphate and concentrated.

$^1$H-NMR (400 MHz, DMSO-$d_6$, 300 K) δ: 10.12 (s, 1H), 4.29-4.16 (m, 2H), 3.80 (s, 3H), 2.95-2.78 (m, 2H), 1.79-1.41 (m, 6H).

$^{13}$C-NMR (100 MHz, DMSO-$d_6$, 300K) δ: 165.79, 158.54, 153.41, 143.55, 126.61, 52.04, 43.02, 35.75, 28.76, 26.94, 24.58.

MS m/z: 239 (M+H)$^+$.

Step 3: Methyl 3-(benzoyloxy)-4-oxo-4,6,7,8,9,10-hexahydropyrimido[1,2-a]azepine-2-carboxylate To a solution of methyl 3-hydroxy-4-oxo-4,6,7,8,9,10-hexahydropyrimido[1,2-a]azepine-2-carboxylate in pyridine, benzoic anhydride (1.1 eq.) and a catalytic amount of dimethylaminopyridine were added. The mixture was stirred at room temperature for 3 h. The solvent was removed under reduced pressure and the residue partitioned between dichloromethane and 1 M aq. HCl. The aqueous phase was extracted with dichloromethane and the combined organic phases were washed with 1 M aq. HCl and brine. The organic phase was dried over sodium sulfate, filtered and concentrated to dryness under vacuum. Title compound was obtained after flash chromatography (eluents petroleum ether/ethyl acetate, 6:4) as a brown solid.

$^1$H-NMR (400 MHz, DMSO-$d_6$, 300 K) δ: 8.07 (dd, J=8.6, 1.3 Hz, 2H), 7.78 (t, J=7.5 Hz, 1H), 7.62 (t, J=7.9 Hz, 2H), 4.31-4.29 (m, 2H), 3.74 (s, 3H), 3.06-3.04 (m, 2H), 1.82-1.65 (m, 6H).

$^{13}$C-NMR (75 MHz, DMSO-$d_6$, 300K) δ: 162.78, 162.65, 162.43, 157.01, 140.29, 135.23, 134.18, 129.63, 128.86, 127.59, 52.46, 43.13, 36.07, 28.47, 26.12, 23.68.

MS m/z: 343 (M+H)$^+$.

Step 4: Methyl 3-(benzoyloxy)-10-bromo-4-oxo-4,6,7,8,9,10-hexahydropyrimido[1,2-a]azepine-2-carboxylate A mixture of methyl 3-(benzoyloxy)-4-oxo-4,6,7,8,9,10-hexahydropyrimido[1,2-a]azepine-2-carboxylate, N-bromosuccinimide (2 eq.) and α,α'-azoisobutyronitrile (0.45 eq.) in carbon tetrachloride was stirred under reflux for 14 hour. The mixture was cooled to room temperature, the succinimide was filtered off and the solvent was removed under reduced pressure. Methyl 3-(benzoyloxy)-10-bromo-4-oxo-4,6,7,8,9,10-hexahydropyrimido[1,2-a]azepine-2-carboxylate was obtained after flash chromatography (eluents petroleum ether/ethyl acetate, 8:2) as a pale yellow solid.

$^1$H-NMR (400 MHz, DMSO-$d_6$, 300 K) δ: 8.07 (dd, J=8.3, 0.9 Hz, 2H), 7.79 (t, J=7.5 Hz, 1H), 7.63 (t, J=7.9 Hz, 2H), 5.63 (dd, J=5.9, 2.2 Hz, 1H), 4.98 (dd, J=14.3, 6.1 Hz, 1H), 3.97 (dd, J=14.3, 11.0 Hz, 1H), 3.76 (s, 3H), 2.31-2.13 (m, 2H), 2.10-1.79 (m, 3H), 1-1.61-1.48 (m, 1H).

$^{13}$C-NMR (75 MHz, DMSO-$d_6$, 300 K) δ: 162.65, 162.14, 157.22, 157.10, 139.45, 136.59, 134.37, 129.72, 128.94, 127.36, 53.56, 52.67, 42.37, 31.52, 25.78, 24.40.

MS m/z: 423/421 (M+H)$^+$.

Step 5: Methyl 3-hydroxy-4-oxo-10-{[(1R)-1-phenylethyl]amino}-4,6,7,8,9,10-hexahydropyrimido[1,2-a]azepine-2-carboxylate Methyl 3-(benzoyloxy)-10-bromo-4-oxo-4,6,7,8,9,10-hexahydropyrimido[1,2-a]azepine-2-carboxylate (1.0 eq.) was added to a solution of (1R)-1-phenylethylamine (2.2 eq.)

and triethylamine (1 eq) dissolved in N,N-dimethylformamide. The mixture was stirred vigorously for 2 hours at room temperature and then at 50° C. for 30 minutes. The solvent was removed under reduced pressure and the title crude product (a mixture 1:1 of diastereoisomers) for use without further purification. In an alternative procedure (Step 5A), solid methyl 3-(benzoyloxy)-10-bromo-4-oxo-4,6,7,8,9,10-hexahydropyrimido[1,2-a]azepine-2-carboxylate (1.0 eq.) was added to a solution of (1R)-1-phenylethylamine (4.5 eq.) dissolved in a 7:3 methanol/water mixture at −30° C. The reaction was carried out over night, then the temperature was raised to room temperature and the solvent concentrated to obtain a white solid that was filtered off and discarded. The title compound (as a mixture 7:3 of diastereoisomers) was extracted in dichloromethane from the mother liquid for use in the next step without further purification.

MS m/z: 358 (M+H)$^+$.

Step 6: N-(4-fluorobenzyl)-3-hydroxy-4-oxo-10-{[(1R)-1-phenylethyl]amino}-4,6,7,8,9,10-hexahydropyrimido[1,2-a]azepine-2-carboxamide p-Fluorobenzylamine (3 eq.) was added to the methyl 3-hydroxy-4-oxo-10-{[(1R)-1-phenylethyl]amino}-4,6,7,8,9,10-hexahydropyrimido[1,2-a]azepine-2-carboxylate (prepared as described in Step 5 or Step 5A) dissolved in methanol. The mixture was stirred at 70° C. overnight, then cooled to room temperature for use directly in Step 7. In an alternative procedure (Step 6A), the solvent was removed and the crude product crystallized from acetonitrile several times to obtain a single diastereoisomer of the title compound as the 4-fluorobenzylammonium salt with d.e.>95%

Step 7: (+) N-(4-fluorobenzyl)-3-hydroxy-10-{methyl[(1R)-1-phenylethyl]amino}-4-oxo-4,6,7,8,9,10-hexahydropyrimido[1,2-a]azepine-2-carboxamide N-(4-Fluorobenzyl)-3-hydroxy-4-oxo-10-{[(1R)-1-phenylethyl]amino}-4,6,7,8,9,10-hexahydropyrimido[1,2-a]azepine-2-carboxamide obtained in Step 6 was dissolved in methanol and the pH was adjusted to circa 5 with acetic acid before 37% aqueous formaldehyde (6 eq.) and sodium cyanoborohydride (6.25 eq.) were added. The mixture was stirred at room temperature overnight. The solvent was removed under reduced pressure and the residue, dissolved in the minimum amount of methanol, was acidified to pH 2-3 with trifluoroacetic acid. The solution was applied on cation-exchange resin cartridges (Varian MEGA BOND ELUTE SCX), the cartridges washed with methanol and the crude product was eluted with 2 M ammonia in methanol. The pooled eluents were concentrated to dryness under reduced pressure to get an oily residue. The product, a mixture of diastereoisomers, was separated by preparative RP-HPLC-purification (column: C18) eluants water (0.1% TFA), acetonitrile (0.1% TFA). The title diastereoisomer was eluted as the first peak, and after lyophilization the title compound was obtained as a white solid (TFA salt).

In an alternative procedure (Step 7A), the product of Step 6A was reacted in the same manner as the product of Step 6 to obtain a single diastereomer without separation by HPLC.

$^1$H-NMR (300 MHz, DMSO-d$_6$-TFA, 300 K) δ: 9.42 (t, J=6.2 Hz, 1H), 9.20 (bs, 1H), 7.60 (bd, J=7.3 Hz, 2H), 7.51-7.29 (m, 5H), 7.21 (t, J=8.9 Hz, 2H), 4.98-4.75 (m, 3H), 4.69 (dd, J=15.5, 6.9 Hz, 1H), 4.47 (dd, J=15.5, 5.5 Hz, 1H), 3.66 (t, J=12.8 Hz, 1H), 2.94-2.81 (m, 3H), 1.97-1.81 (bm, 2H), 1.79-1.33 (m, 7H).

MS m/z: 465 (M+H)$^+$.

$[\alpha]^{20}_D$=+62±2 (C=0.1 in chloroform).

Step 8: (−)$_2$-{[(4-fluorobenzyl)amino]carbonyl}-3-hydroxy-N-methyl-4-oxo-4,6,7,8,9,10-hexahydropyrimido[1,2-a]azepin-10-ammonium trifluoroacetate A solution of the TFA salt of the product of Step 7 (or 7A) in methanol, containing palladium on charcoal (10%, w/w) was stirred under hydrogen at atmospheric pressure for 4 h. The catalyst was filtered off and the solution was concentrated to dryness under reduced pressure to afford the title compound.

$^1$H-NMR (300 MHz, DMSO-d$_6$-TFA, 300 K) δ: 9.88 (bs, 1H), 9.56 (bs, 1H), 9.14 (bs, 1H), 7.41 (dd, J=8.6, 5.7 Hz, 2H), 7.17 (t, J=8.8 Hz, 2H), 4.92 (dd, J=14.6, 4.6 Hz, 1H), 4.72 (bm, 1H), 4.58-4.44 (m, 2H), 3.51 (dd, J=13.9, 11.7 Hz, 1H), 2.66 (t, J=4.9 Hz, 3H), 2.29 (d, J=13.3 Hz, 1H), 2.02-1.57 (m, 4H), 1.45-1.27 (m, 1H).

MS m/z: 361 (M+H)$^+$.

$[\alpha]^{20}_D$=−4±2 (C=0.4 in methanol).

Step 9: (−)N-(-{[(4-Fluorobenzyl)amino]carbonyl}-3-hydroxy-4-oxo-4,6,7,8,9,10-hexahydropyrimido[1,2-a]azepin-10-yl)-N,N',N'-trimethylethanediamide Methyl chlorooxoacetate (2-6 eq.) and N-ethyldiisopropylamine (4 eq.) were added to a solution of the ammonium trifluoroacetate compound of Step 8 in chloroform. The mixture was stirred at room temperature for 1 hour. The solvent was removed under reduced pressure and the residue dissolved in a 2 M solution of dimethylamine in methanol was stirred at room temperature for 6 hours. The solvent was removed under reduced pressure and the residue dissolved in dichloromethane was washed with 1 M HCl in water. The organic phase was dried over anhydrous Na$_2$SO$_4$ and the solvent removed under reduced pressure. The title product was isolated by preparative RP-HPLC, using water (0.1% TFA) and acetonitrile (0.1% TFA) as eluents (column: C18). The pooled product fractions were lyophilized to afford the title product with an enantiomeric excess of 99.5% (e.e. determined by Chiral HPLC Chiralpak AD, mobile phase 0.2% TFA n-Hex/0.2% TFA ethanol with 3% methanol). An amorphous potassium salt of the title compound was obtained by treating the compound dissolved in acetonitrile with aqueous KOH and then freeze drying.

$^1$H-NMR spectra was identical to the compound described in Example 11.

$^{13}$C-NMR (100 MHz, DMSO-d$_6$, 300 K) δ: 168.01, 165.80, 165.03, 161.30 (d, J$_{C-F}$=243 Hz), 157.68, 149.67, 145.94, 134.59, 129.56 (d, J$_{C-F}$=8.5 Hz), 124.72, 115.10 (d, J$_{C-F}$=21 Hz), 55.88, 42.42, 41.56, 36.24, 32.79, 32.34, 28.83, 27.10, 26.15.

MS m/z: 460 (M+H)$^+$.

$[\alpha]^{20}_D$=−72±2 (C=0.1 in chloroform).

Example 13

Racemic N-(2-{[(4-fluorobenzyl)amino]carbonyl}-3-hydroxy-4-oxo-4,6,7,8,9,10-hexahydropyrimido[1,2-a]azepin-10-yl)-N',N'-trimethylethanediamide

Step 1: Preparation of ω-Hydroxy N-Methyl Aminonitrile 3

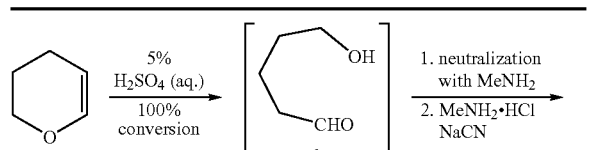

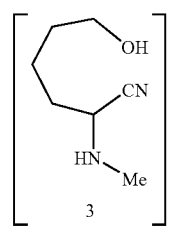

| Materials | MW | Equiv. | Moles | Wt. (g) | Vol. (mL) | Density |
|---|---|---|---|---|---|---|
| DHP | 84.12 | 1 | 0.2500 | 21.10 | 22.93 | 0.92 |
| 5% H$_2$SO$_4$ | 98.08 | 0.122 | 0.0305 | | 60 mL | |
| 40% MeNH$_2$ | 31.06 | 0.244 | 0.0610 | 4.74 | 5.3 | 0.902 |
| MeNH$_2$•HCl | 67.51 | 5 | 1.250 | 84.4 | | |
| NaCN | 49.01 | 1 | 0.2500 | 12.25 | | |
| IPAc | | | | | 900 | |

To a 5% H$_2$SO$_4$ aqueous solution was added 3,4-dihydro-2H-pyran (DHP; 21.1 g) at 20-35° C. The resulting solution was aged at 20-35° C. for 1 h. The reaction mixture was cooled to 0-5° C., and neutralized to pH=6-7 by 40% aqueous methylamine. Methylamine hydrochloride and sodium cyanide were added respectively to the reaction mixture. The resulting solution was aged at room temperature for 36 h. The reaction mixture was extracted by IPAc (6×150 mL). The combined organic layers were concentrated to a total volume about 150 mL (assay yield about 91%) and was used in the next step. $^1$H NMR (CDCl$_3$, 400 MHz) δ: 3.81 (m, 1H), 3.45 (m, 2H), 2.47 (s, 3H), 1.90-1.40 (m, 6H).

Step 2: Preparation of ω-Hydroxy N-Methyl N-Boc-Aminonitrile 4

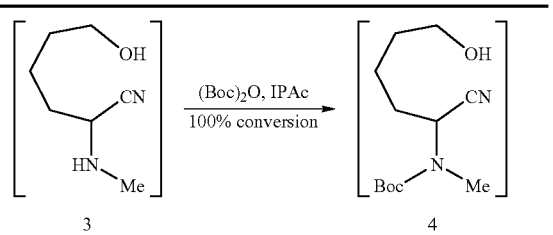

| Materials | MW | Equiv. | Moles | Wt. (g) | Vol. (mL) |
|---|---|---|---|---|---|
| Aminonitrile 3 | 142.20 | 1 | 0.2106 | 29.95 | |
| (Boc)$_2$O | 218.25 | 1.05 | 0.2211 | 48.3 | |

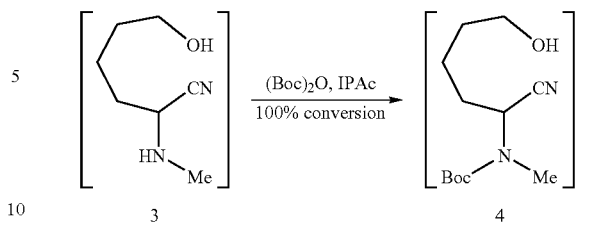

| Materials | MW | Equiv. | Moles | Wt. (g) | Vol. (mL) |
|---|---|---|---|---|---|
| 5% NH$_2$OH/ 10% NH$_4$Cl | | | | | 35 |
| IPAc | | | | | 80 |

To a solution of ω-hydroxy N-methyl aminonitrile 3 (0.2106 moles) in IPAc (from Step 1) was added (Boc)$_2$O (48.3 g) at room temperature. The resulting solution was aged at 30-35° C. for 2 h (100% conversion by $^1$H NMR). The reaction mixture was cooled to 0-5° C. and 5% NH$_2$OH/10% NH$_4$Cl (35 mL) was added. The resulting mixture was aged at 10-20° C. for 3 h. After a phase cut, the aqueous layer was extracted with IPAc (80 mL), the combined organic layers were washed with brine (50 mL), and then concentrated and solvent-switched to IPA (total volume 230 mL), which was used for next step. $^1$H NMR (CDCl$_3$, 400 MHz) δ: 5.18 (m, 1H), 3.64 (q, J=5.7 Hz, 2H), 2.88 (s, 3H), 1.88-1.75 (m, 3H). 1.65-1.61 (m, 2H), 1.49-1.46 (m, 1H), 1.18 (s, 9H).

Step 3: Preparation of Hydroxyamidine 5

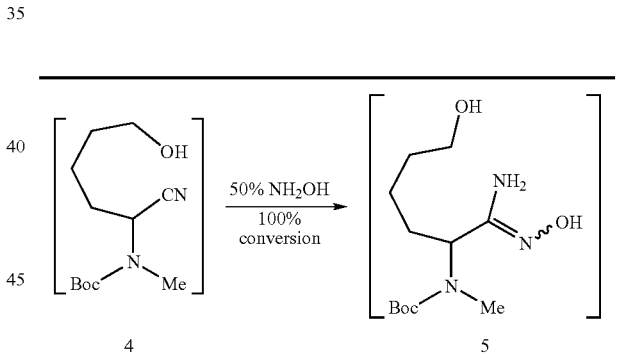

| Materials | MW | Equiv. | Moles | Wt. (g) | Vol. (mL) | Density |
|---|---|---|---|---|---|---|
| N-Boc-aminonitrile 4 | 242.31 | 1 | 0.2106 | 51.03 | | |
| 50% NH$_2$OH | 33.03 | 1.25 | 0.2633 | 17.40 | 16.20 | 1.078 |
| IPA | | | | | 180 | |
| MeOH | | | | | 600 | |

To a solution of N-Boc-aminonitrile 4 (0.2106 moles) in IPA (total volume 230 mL) was added 50% hydroxylamine (16.2 mL) at ambient temperature. The resulting solution was aged at 60° C. for 3 h. The reaction mixture was then concentrated and solvent-switched to methanol solution (total volume 230 mL), which was used in the next step. $^1$H NMR (CDCl$_3$, 400 MHz) δ: 7.53 (br s, 1H), 4.84 (br s, 2H), 4.64 (t, J=7.1 Hz, 1H), 3.71-3.62 (m, 2H), 2.72 (s, 3H), 2.00 (br s, 1H), 1.92-1.82 (m, 1H), 1.76 (1.55 (m, 3H), 1.49 (s, 9H), 1.42-1.23 (m, 2H).

HPLC conditions: Column: Zorbax, Rx C8 250×4.6 mm; Temperature: 30° C.; Detection at 210 nm; Mobile Phase: 0.1% aq H$_3$PO$_4$ (A)/MeCN (B); Gradient: 90:10 (A)/(B) to 10:90 over 15 min, 10:90 hold for 5 min, 10:90 to 90:10 (A)/(B) over 10 seconds; Flow Rate: 1 mL/min. Retention time: amidoxime—6.152 minutes and 6.256 minutes (two isomers)

Step 4: Preparation of O-Alkene Amidoxime 6

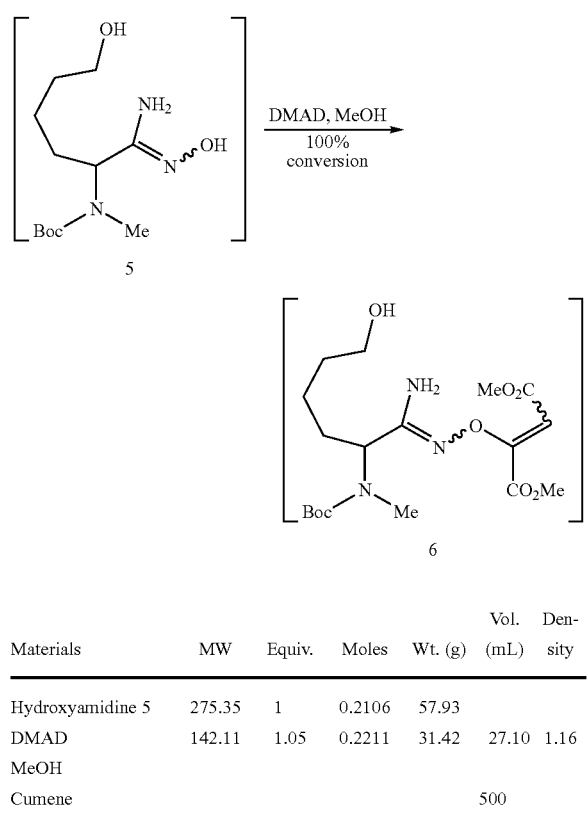

| Materials | MW | Equiv. | Moles | Wt. (g) | Vol. (mL) | Density |
|---|---|---|---|---|---|---|
| Hydroxyamidine 5 | 275.35 | 1 | 0.2106 | 57.93 | | |
| DMAD | 142.11 | 1.05 | 0.2211 | 31.42 | 27.10 | 1.16 |
| MeOH | | | | | | |
| Cumene | | | | | 500 | |

To a solution of hydroxyamidine 5 (about 0.2106 mole) in methanol (total volume 230 mL) was added dimethyl acetylenedicarboxylate (27.10 mL) at room temperature. The resulting solution was aged at room temperature for 16 h. The reaction mixture was concentrated and solvent-switched to cumene at 40-60° C. (total volume 430 mL). The solution was used in the next step. $^1$H NMR (CDCl$_3$, 400 MHz) δ: 5.82 (s, 0.28H), 5.73 (s, 0.72H), 5.44 (br s, 1.77H), 5.25 (br s, 0.56H), 4.61 (m, 1H), 3.89 (s, 0.84H), 3.84 (s, 2.16H), 3.72 (s, 2.16H), 3.68 (s, 0.84H), 3.65-3.58 (m, 2H), 2.73 (s, 0.84H), 2.71 (s, 2.16H), 1.90-1.52 (m, 4H), 1.47 (s, 9H), 1.43-1.30 (m, 2H).

HPLC conditions: Column: Zorbax, Rx C8 250×4.6 mm; Temperature: 30° C.; Detection at 210 nm; Mobile Phase: 0.1% aq H$_3$PO$_4$ (A)/MeCN (B); Gradient: 90:10 (A)/(B) to 10:90 over 15 min, 10:90 hold for 5 min, 10:90 to 90:10 (A)/(B) over 10 seconds; Flow Rate: 1 mL/min. Retention time: amidoxime 6—12.051 minutes, 12.315 minutes, ratio ca 3.6:1.

Step 5: Preparation of Pyrimidine 7

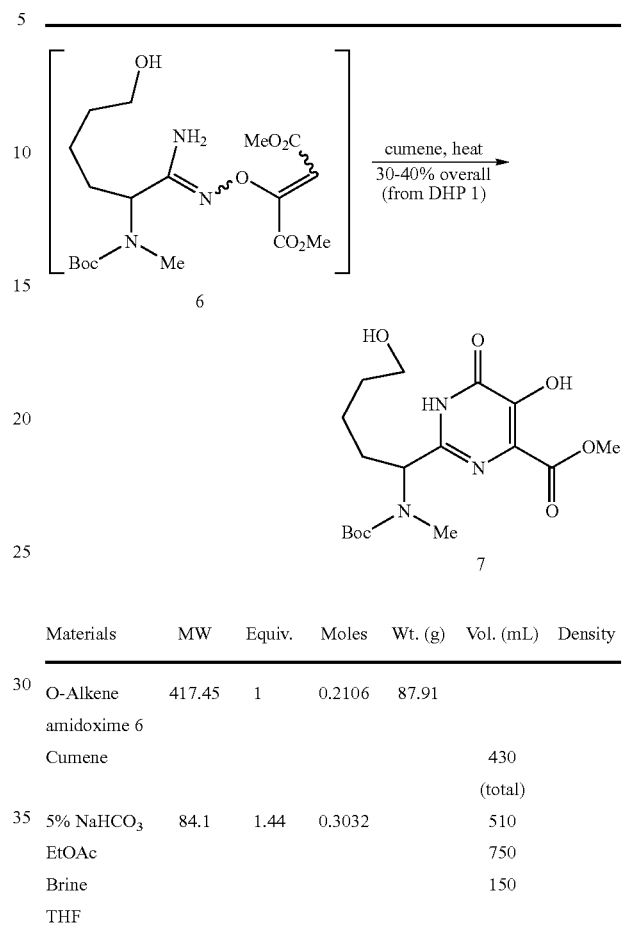

| Materials | MW | Equiv. | Moles | Wt. (g) | Vol. (mL) | Density |
|---|---|---|---|---|---|---|
| O-Alkene amidoxime 6 | 417.45 | 1 | 0.2106 | 87.91 | | |
| Cumene | | | | | 430 (total) | |
| 5% NaHCO$_3$ | 84.1 | 1.44 | 0.3032 | | 510 | |
| EtOAc | | | | | 750 | |
| Brine | | | | | 150 | |
| THF | | | | | | |

A solution of O-alkene amidoxime 6 (about 0.2106 moles) in cumene (total volume 430 mL) was heated at 120° C. (inside temperature) for 12 h. The reaction mixture was then cooled to about 60° C., concentrated to a total volume 250 mL, then diluted with EtOAc (250 mL), and cooled to 25-35° C. 5% Sodium bicarbonate (330 mL, about 1 equiv.) was then slowly added, and the resulting solution was aged at 25-35° C. for 0.5 h. After a phase cut, the organic layer was extracted with 5% sodium bicarbonate (180 mL) again. The combined aqueous extracts were acidified by 5 N HCl to pH=2-3, and extracted by EtOAc (3×250 mL). The combined organic layers were washed with brine (150 mL). The organic solution was concentrated and solvent-switched to THF (about 30-40% yield overall, KF about 100-150 ppm). $^1$H NMR (CDCl$_3$, 400 MHz) δ: 10.66 (br s, 2H), 4.77 (m, 1H), 4.01 (s, 3H), 3.72-3.67 (m, 2H), 2.77 (s, 3H), 2.20-1.55 (m, 5H), 1.48 (s, 9H), 1.43-1.35 (m, 1H).

HPLC conditions: Column: Zorbax, Rx C8 250×4.6 mm; Temperature: 30° C.; Detection at 210 nm; Mobile Phase: 0.1% aq H$_3$PO$_4$ (A)/MeCN (B); Gradient: 90:10 (A)/(B) to 10:90 over 15 min, 10:90 hold for 5 min, 10:90 to 90:10 (A)/(B) over 10 seconds; Flow Rate: 1 mL/min. Retention time: pyrimidine 7—9.905 minutes

Step 6: Preparation of Bismesyl-Pyrimidine 8

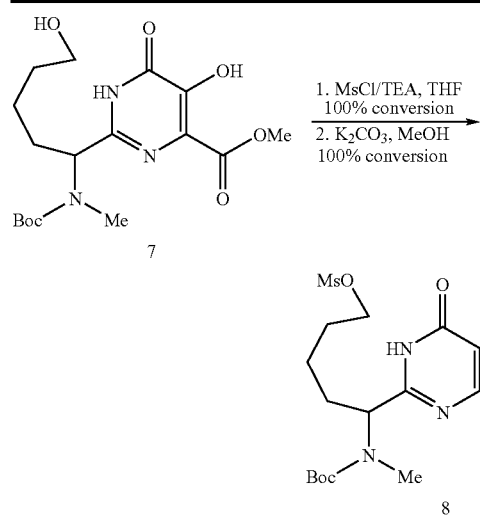

| Materials | MW | Equiv. | Moles | Wt. (g) | Vol. (mL) | Density |
|---|---|---|---|---|---|---|
| Pyrimidine 7 | 385.41 | 1 | 0.09029 | 43.5 (80%) | | |
| TEA | 101.19 | 3 | 0.2709 | 27.4 | 37.8 | 0.726 |
| MsCl | 114.55 | 3 | 0.2709 | 31.0 | 21.0 | 1.480 |
| THF | | | | | 575 | |
| $K_2CO_3$ | 138.21 | 1 | 0.09029 | 12.5 | | |
| MeOH | | | | | 200 | |
| EtOAc | | | | | 400 | |

To a solution of pyrimidine 7 (43.5 g, about 80% pure, 0.09029 moles) in THF (275 m L) was slowly added TEA (37.8 mL) and MsCl (21.0 mL) at the same time at 0-5° C. over 1 h. The resulting solution was aged at the same temperature for 4 h. The solid was filtered off, washed with THF (3×100 mL). The combined filtrations were concentrated and solvent-switched to methanol (total volume 200 mL). To the trimesyl-pyrimidine in methanol solution was added potassium carbonate (12.5 g, 0.09029 moles) at 10-20° C. The resulting solution was aged at the same temperature for 6-10 h (monitored by HPLC). The reaction mixture was neutralized to pH=6-7 by 5 N HCl, and concentrated to a total volume about 100 mL. 16% brine (100 mL) was added, and the resulting solution was extracted by EtOAc (3×100 mL). The combined organic layers were washed with brine (50 mL), concentrated and solvent-switched to DMF. The by-product ($MeSO_3Me$), which was generated in 1 equiv from the selectively hydrolysis of the trimesyl-pyrimidine, was removed by azeotrope with DMF at 60-65° C. (monitored by $^1$H NMR until <10 mole %). The concentration of bismesyl-pyrimidine 8 in DMF was about 0.3 M (total volume 300 mL). $^1$H NMR ($CDCl_3$, 400 MHz) δ: 11.00 (br s, 1H), 4.78 (d, J=7.8 Hz, 1H), 4.24-4.15 (m, 2H), 3.95 (s, 3H), 3.50 (s, 3H), 2.99 (s, 3H), 2.81 (s, 3H), 2.12-2.11 (m, 1H), 1.90-1.76 (m, 2H), 1.46 (s, 9H), 1.43-1.35 (m, 2H).

HPLC conditions: Column: Zorbax, Rx C8 250×4.6 mm; Temperature: 30° C.; Detection at 210 nm; Mobile Phase: 0.1% aq $H_3PO_4$ (A)/MeCN (B); Gradient: 90:10 (A)/(B) to 10:90 over 15 min, 10:90 hold for 5 min, 10:90 to 90:10 (A)/(B) over 10 seconds; Flow Rate: 1 mL/min. Retention time: trimesyl-pyrimidine—14.140 minutes; bismesyl-pyrimidine—12.760 minutes.

Step 7: Preparation of Seven-Membered Ring-Pyrimidine Mesylate 9

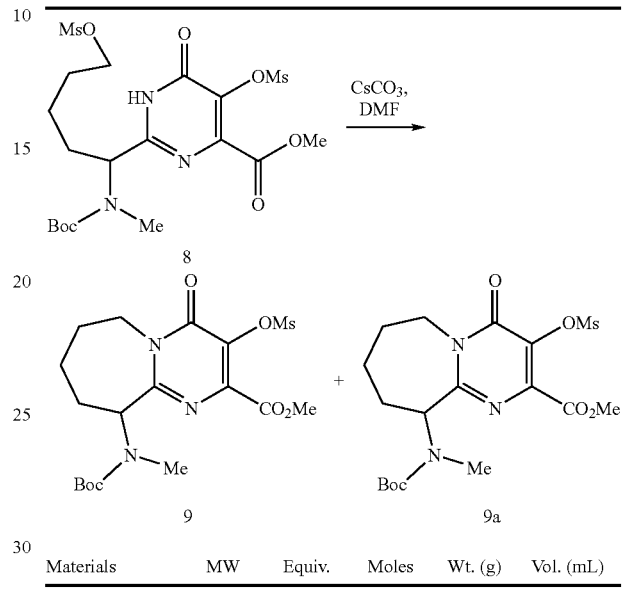

| Materials | MW | Equiv. | Moles | Wt. (g) | Vol. (mL) |
|---|---|---|---|---|---|
| Bismesyl-pyrimidine 8 | 541.59 | 1 | 0.09029 | 48.90 | |
| $Cs_2CO_3$ | 325.82 | 1.2 | 0.1083 | 35.30 | |
| DMF | | | | | |

To a solution of bismesyl-pyrimidine 8 (0.09029 moles) in DMF (total volume 300 mL) was added cesium carbonate (35.30 g) at room temperature. The resulting slurry was aged at 55° C. for 2-3 h (76% conversion by HPLC). After being neutralized to pH=7, the reaction mixture was diluted with 250 mL of water, extracted with IPAc (2×250 mL). The combined organic layers were washed with brine (2×200 mL). The organic layer was concentrated to give crude product. Half of the crude product was purified by passing a short column (silica gel, hexane: EtOAc 2:1) to afford desired product 9 (6.00 g, 98A % pure), and 9a (2.3 g, 40A % pure). The overall yield from DHP to cyclized product is about 13% after correction.

$^1$H NMR ($CDCl_3$, 400 MHz) For compound 9: δ:5.34 (m, 1H), 5.22 (m, 1H), 3.93 (s, 3H), 3.51 (s, 3H), 3.47 (m, 1H), 2.97 (s, 3H), 2.20-2.05 (m, 3H), 1.90-1.65 (m, 2H), 1.44 (s, 9H), 1.24 (m, 1H). For compound 9a: 11.86 (br s, 1H), 7.90-7.55 (br s, 1H), 7.31 (dd, J=8.5, 5.4 Hz, 2H), 7.06 (t, J=8.5 Hz, 2H), 5.40-4.90 (m, 2H), 4.53-4.40 (m, 2H), 3.45-3.23 (m, 1H), 2.23-2.05 (m, 3H), 1.86-1.76 (m, 1H), 1.74-1.64 (m, 1H), 1.47-1.37 (m, 1H), 1.30 (s, 9H). HPLC conditions: Column: Zorbax, Rx C8 250×4.6 mm; Temperature: 30° C.; Detection at 210 nm; Mobile Phase: 0.1% aq $H_3PO_4$ (A)/MeCN (B); Gradient: 90:10 (A)/(B) to 10:90 over 15 min, 10:90 hold for 5 min, 10:90 to 90:10 (A)/(B) over 10 seconds; Flow Rate: 1 mL/min. Retention time: the seven-membered ring-pyrimidine mesylate 9: 13.969 minutes; the seven-membered ring-pyrimidine 9a: 13.141 minutes.

Alternative procedure using LiH was also employed: To a solution of bismesyl-pyrimidine 8 (65 mg) in dioxane (1 mL) was added LiH powder at room temperature. The resulting mixture was aged at 65° C. for 4 h. The reaction mixture was then cooled to room temperature and 1 N HCl was added to quenched the excess LiH. The solution was extracted with EtOAc (2×5 mL). The combined organic layer was washed with brine, and then concentrated. The residue was purified by flash chromatography (silica gel, hexane:EtOAc=2:1) to afford seven-membered ring-pyrimidine mesylate 9 (45.6 mg, 85%). $^1$H NMR (CDCl$_3$, 400 MHz) δ: 5.34 (m, 1H), 5.22 (m, 1H), 3.93 (s, 3H), 3.51 (s, 3H), 3.47 (m, 1H), 2.97 (s, 3H), 2.20-2.05 (m, 3H), 1.90-1.65 (m, 2H), 1.44 (s, 9H), 1.24 (m, 1H).

Step 8: Preparation of Seven-Membered Ring-Pyrimidine Amide 10

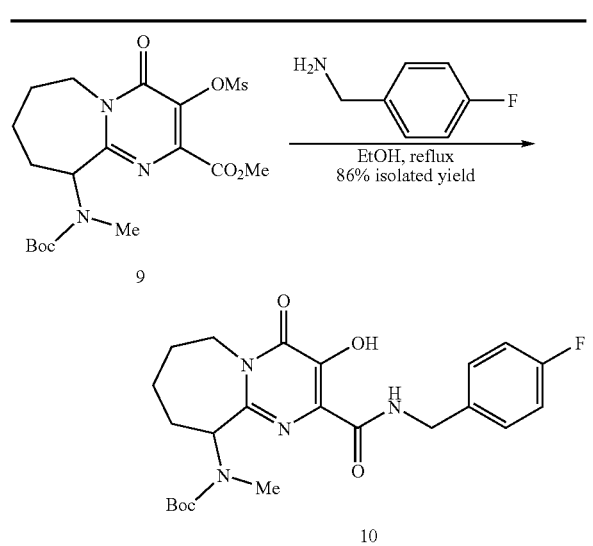

| Materials | MW | Equiv. | Moles | Wt. (g) | Vol. (mL) | Density |
|---|---|---|---|---|---|---|
| Seven-membered ring pyrimidine 9 | 445.49 | 1 | 0.01347 | 6.000 | | |
| 4-fluoro-benzylamine | 125.15 | 3 | 0.04041 | 5.060 | 5.22 | 1.09 |
| EtOH | | | | | 80 | |

To a solution of seven-membered ring-pyrimidine mesylate 9 (6 g) in EtOH (80 mL) was added 4-fluorobenzylamine (5.060 g). The resulting solution was reflux for 8 h. (100% conversion by HPLC). The reaction mixture was concentrated to about 20 mL total volume, and 80 mL of EtOAc was added. To the resulting solution was added 20% brine (15 mL), 4 N HCl (15 mL), and water 10 mL). After a phase cut, the aqueous layer was back-extracted with EtOAc (25 mL). The combined organic layers were washed with 4 N HCl: 20% brine (1:1, 3×15 mL), brine (15 mL). The organic solution was concentrated to a total volume about 30 mL. Hexane (70 mL) was slowly added to the solution over 1 h. The resulting slurry was aged at 0-5° C. for 1 h. The crystalline solid was filtered off, washed with hexane:EtOAc (4:1, 50 mL), dried under vacuum with nitrogen sweep to afford seven-membered ring-pyrimidine amide 10 (5.30 g, 86%, HPLC>97A %). $^1$H NMR (CDCl$_3$, 400 MHz) δ: 11.85 (br s, 1H), 7.84 (br s, 0.5H), 7.68 (br s, 0.5H), 7.31 (m, 2H), 7.04 (m, 2H), 5.40-4.90 (m, 2H), 4.53 (m, 2H), 3.38 (m, 1H), 2.87 (s, 3H), 2.20-2.15 (m, 3H), 1.90-1.40 (m, 3H), 1.37 (s, 9H).

HPLC conditions: Column: Zorbax, Rx C8 250×4.6 mm; Temperature: 30° C.; Detection at 210 nm; Mobile Phase: 0.1% aq H$_3$PO$_4$ (A)/MeCN (B); Gradient: 90:10 (A)/(B) to 10:90 over 15 min, 10:90 hold for 5 min, 10:90 to 90:10 (A)/(B) over 10 seconds; Flow Rate: 1 mL/min. Retention time: the seven-membered ring-pyrimidine 10—15.467 minutes.

Step 9: Preparation of Seven-Membered Ring-Pyrimidine Amide Hydrochloride Salt 11

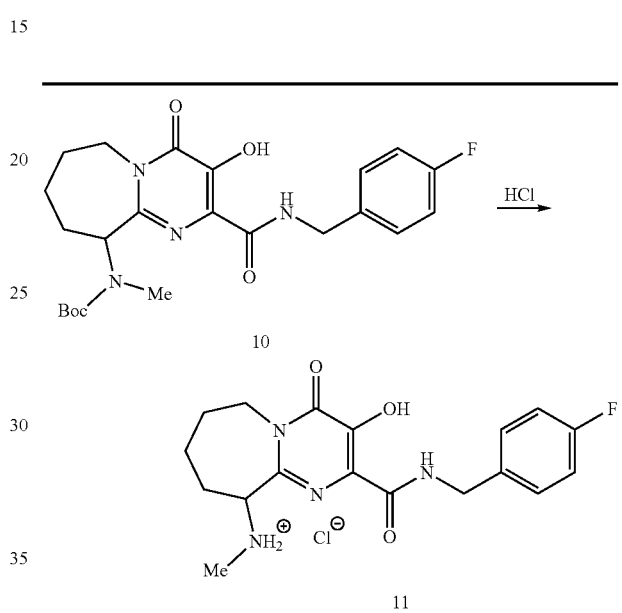

| Materials | MW | Equiv. | Moles | g | mL | Density |
|---|---|---|---|---|---|---|
| Seven-membered pyrimidine amide 10 | 460.50 | 1 | 0.001846 | 0.8500 | | |
| HCl (gas) | 36.46 | 8 | 0.01478 | 0.5389 | | |
| EtOAc | | | | | 3.5 | |

To a solution of ethyl acetate (3.5 mL) was bubbled HCl gas (0.5389 g), at −30 to −20° C. N-Boc-seven-membered ring pyrimidine amide 10 (crystalline solid) was charged to the HCl-EtOAc solution at −30 to −20° C. The resulting solution was slowly warmed to room temperature over 2.5 h, and aged at room temperature for 0.5 h (100% conversion by HPLC). The reaction mixture was diluted by EtOAc (7 mL). The resulting slurry was aged at 0-5° C. for 1 h. The crystalline solid was filtered off, washed with EtOAc, hexane, dried under vacuum with nitrogen sweep to afford desired product 11 (98% isolated yield, >97A % pure). $^1$H NMR (CDCl$_3$, 400 MHz) δ: 12.35 (s, 1H), 9.96 (t, J=6.3 Hz, 1H), 9.51 (br s, 1H), 9.19 (br s, 1H), 7.42 (dd, J=8.5, 5.6 hz, 2H), 7.19 (t, J=8.5 Hz, 2H), 4.92 (dd, J=14.5, 5.1 Hz, 1H), 4.71 (m, 1H), 4.57-4.45. (m, 2H), 3.52 (t, J=14.5 Hz), 2.65 (t, J=5.0 HZ, 3H), 2.30 (br d, J=12.6 Hz, 1H), 1.99-1.92 (m, 1H), 1.90-1.75 (m, 2H), 1.68-1.60 (m, 1H), 1.41-1.33 (m, 1H).

HPLC conditions: Column: Zorbax, Rx C8 250×4.6 mm; Temperature: 30° C.; Detection at 210 nm; Mobile Phase: 0.1% aq H$_3$PO$_4$ (A)/MeCN (B); Gradient: 90:10 (A)/(B) to 10:90 over 15 min, 10:90 hold for 5 min, 10:90 to 90:10

(A)/(B) over 10 seconds; Flow Rate: 1 mL/min. Retention time: the seven-membered ring-pyrimidine hydrochloride salt 11—8.118 minutes.

Step 10: Preparation of Racemic N-(2-{[(4-fluorobenzyl)amino]carbonyl}-3-hydroxy-4-oxo-4,6,7,8,9,10-hexahydropyrimido[1,2-a]azepin-10-yl)-N,N',N'-trimethylethanediamide 14

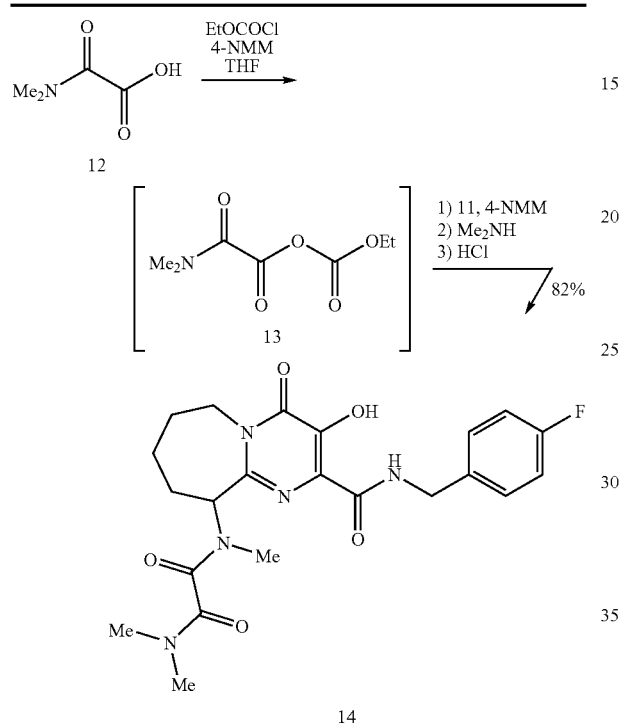

| Materials | MW | Equiv. | mmoles | Wt. (g) | Vol. (mL) | Density |
|---|---|---|---|---|---|---|
| Acid 12 (96% pure) | 117.10 | 5 | 1.000 | 0.122 | | |
| Ethyl chloroformate | 125.15 | 4.8 | 0.960 | 0.104 | 0.092 | 1.135 |
| 4-NMM THF | 101.15 | 4.8 | 0.960 | 0.0971 | 0.1063 | 0.9200 |
| pyrimidine hydrochloride salt 11 | 396.84 | 1 | 0.200 | 0.0794 | | |
| 40% dimethylamine 2 N HCl | 45.07 | 6.25 | 1.250 | 0.141 | 0.158 | 0.8900 |

To a solution of acid 12 (122 mg) in THF (3 mL) was added ethyl chloroformate (92 μl) at 0-5° C. Then, 4-NMM (106 μl) was slowly added to the reaction mixture at 0-5° C. The reaction mixture was aged at the same temperature for 2 h. The pyrimidine hydrochloride salt 11 (79.4 mg) was added as a solid to the mixed-anhydride solution at 0-5° C., and aged at the same temperature for 5 h, and then at 5-10° C. for another 2 h (100% conversion by HPLC). Dimethylamine aqueous (40%, 158 μl) was added to the reaction mixture, and the mixture aged at 10-15° C. for 1 h, wherein the reaction was monitored by HLPC to assure complete conversion. The reaction mixture was acidified by 2 N HCl to adjust to pH=3-4 at 5-15° C. EtOAc (6 mL) and brine (2 mL) were added, respectively. After phase cut, the organic layer was washed with 1 N HCl (2 mL), brine (2×2 mL). The organic layer was concentrated to a total volume of 1 mL. Hexane (5 mL) was slowly added over 0.5 h. The resulting slurry was aged at 0-5° C. for 1 h. The crystalline solid was filtered off, washed with hexane/EtOAc (5:1), MTBE, dried under vacuum with nitrogen sweep to give the title compound 14 (75.6 mg, 82%). $^1$H NMR (CDCl$_3$, 400 MHz) δ: 12.13 (s, 1H), 9.41 (br s, 1H), 7.38 (dd, J=8.5, 5.4 Hz, 2H), 7.00 (t, J=8.5 Hz, 2H), 5.40 (br s, 1H), 5.29 (dd, J=14.5, 6.0 Hz, 1H), 4.60 (dd, J=14.5, 6.6 Hz, 1H), 4.52 (dd, J=14.5, 6.3 Hz, 1H), 3.35 (dd, J=14.5, 11.6 Hz, 1H), 3.04 (s, 3H), 3.01 (s, 3H), 2.98 (s, 3H), 2.23-2.12 (m, 3H), 1.95-1.81 (m, 2H), 1.58-1.49 (m, 1H).

HPLC conditions: Column: Zorbax, Rx C8 250×4.6 mm; Temperature: 30° C.; Detection at 210 nm; Mobile Phase: 0.1% aq H$_3$PO$_4$ (A)/MeCN (B); Gradient: 90:10 (A)/(B) to 10:90 over 15 min, 10:90 hold for 5 min, 10:90 to 90:10 (A)/(B) over 10 seconds; Flow Rate: 1 mL/min. Retention time: the title compound 14—12.191 minutes.

Example 14

(−)-(7S)-7-Amino-N-(4-fluorobenzyl)-3-hydroxy-4-oxo-6,7,8,9-tetrahydro-4H-pyrido[1,2-a]pyrimidine-2-carboxamide

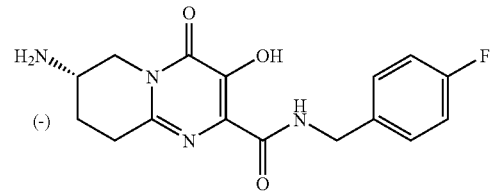

Step 1: Benzyl [(3S)-6-oxopiperidin-3-yl]carbamate

The compound was prepared according to the literature: Kokotos, G., Markidis, T., Costantinou-Kokotou, V., Synthesis 1223-1226 (1996).

Step 2: Methyl (7S)-7-{[(benzyloxy)carbonyl]amino}-3-hydroxy-4-oxo-6,7,8,9-tetrahydro-4H-pyrido[1,2-a]pyrimidine-2-carboxylate Benzyl [(3S)-6-oxopiperidin-3-yl]carbamate prepared in Step 1 was converted to the corresponding oxyme following the procedure reported in *Tetrahedron Letters,* 41 (2000), 299-301. This intermediate was reacted with DMAD and cyclized to the desired product as described in Example 12, Step 1 and Step 2

$^1$H-NMR (DMSO-d$_6$+TFA, 400 MHz, 300K) δ: 7.66 (bs, 1H), 7.40-7.27 (m, 5H), 5.04 (bs, 2H), 4.10-3.97 (m, 2H), 3.87-3.78 (m, 4H), 2.96-2.78 (m, 2H), 2.10-2.00 (m, 1H), 1.83-1.71 (m, 1H). MS: m/z (%): 374 ((M+H)$^+$, 100).

Step 3

The product from Step 2 was dissolved in MeOH (6 mmol), p-fluorobenzylamine (2.0 eq) was added and the mixture was stirred at reflux for 6 hours. The solvent was removed under reduced pressure and the residue was diluted with ethyl acetate. The organic phase was washed with 1N HCl, brine, dried over Na$_2$SO$_4$, filtered and concentrated to dryness under vacuum. To the resulting crude MeOH was added (20 ml/mmol) and the mixture was hydrogenated at atm pressure on 10% (w/w) Pd/C over night. After filtration of the catalyst, solvent was evaporated to give a crude that was purified by preparative RP-HPLC (Symmetry Column C18, 5 μm, 19×100 mm, gradient of CH$_3$CN/H$_2$O+0.01% TFA).

Characterized as TFA salt:

$^1$H-NMR (DMSO-d$_6$, 400 MHz, 300K) δ: 12.3 (bs, 1H), 8.10 (bs, 3H), 7.40-7.33 (m, 2H), 7.22-7.12 (m, 2H), 4.52-4.40 (m, 2H), 4.16-4.07 (m, 2H), 3.87-3.80 (m, 1H), 2.90-2.80 (m, 2H), 2.30-2.22 (m, 1H), 1.78-1.66 (m, 1H).

MS: m/z (%): 333 ((M+H)$^+$, 100).

$[\alpha]^{20}_D$=-6 (C=0.1 in methanol).

Example 15

(+/-)-8-[acetyl(methyl)amino]-N-(4-fluorobenzyl)-3-hydroxy-4-oxo-6,7,8,9-tetrahydro-4H-pyrido[1,2-a]pyrimidine-2-carboxamide

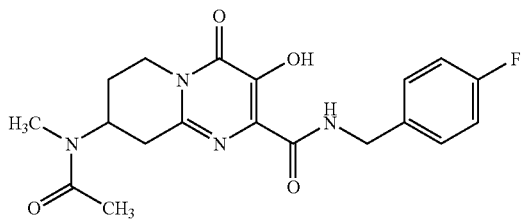

Step 1: Methyl 3-(benzoyloxy)-4-oxo-6,7-dihydro-4H-pyrido[1,2-a]pyrimidine-2-carboxylate To a solution of methyl 3-(benzoyloxy)-9-bromo-4-oxo-6,7,8,9-tetrahydro-4H-pyrido[1,2-a]pyrimidine-2-carboxylate (obtained following Example 2, Step 1) in anhydrous DMF was added triethylamine (2 eq.). The mixture was stirred and heated to 100° C. for 3 h. After cooling to room temperature the mixture was partitioned between 0.1 M HCl and EtOAc. The aq. phase was again extracted with EtOAc and the combined org. phases were dried over sodium sulfate, filtered, concentrated to dryness under vacuum. The crude product so obtained was used in the subsequent step without further purification. An analytical sample of the title compound was obtained by crystallization from methanol. A pale yellow solid was obtained.

$^1$H-NMR (300 MHz, DMSO-d$_6$) δ: 8.08 (m, 2H), 7.79 (m, 1H), 7.63 (m, 2H), 6.87 (m, 1H), 6.43 (d, J=9.7 Hz, 1H), 4.11 (t, J=7.5 Hz, 2H), 3.75 (s, 3H), 2.59 (m, 2H). MS: m/z: 327 (M+H)$^+$

Step 2: N-(4-fluorobenzyl)-3-hydroxy-8-[methoxy(methyl)amino]-4-oxo-6,7,8,9-tetrahydro-4H-pyrido[1,2-a]pyrimidine-2-carboxamide To a solution of methyl 3-(benzoyloxy)-4-oxo-6,7-dihydro-4H-pyrido[1,2-a]pyrimidine-2-carboxylate in anhydrous DMF were added O, N-dimethylhydroxylamine hydrochloride (2.5 eq.) and DIPEA (2.2 eq.). The mixture was stirred and warmed to 65° C. for 6 h. The mixture was cooled to room temperature and the solvent was removed under high vacuum. The residue was dissolved in methanol and p-fluoro-benzylamine (2.2 eq.) and triethylamine (2 eq.) were added. The mixture was stirred at 65° C. for 16 h. After cooling to room temperature the mixture was partitioned between aq. ammonium chloride and dichloromethane. The aq. phase was again extracted with dichloromethane. The combined organic phases were then extracted with 0.1 M NaOH. The aq. phase was then acidified to pH 5 ca. with 1 M aq. HCl and extracted with dichloromethane. The organic phase was dried over sodium sulfate, filtered and concentrated to dryness. The crude product so obtained was used in the subsequent step without further purification.

MS m/z: 377 (M+H)$^+$.

Step 3: N-(4-fluorobenzyl)-3-hydroxy-8-(methylamino)-4-oxo-6,7,8,9-tetrahydro-4H-pyrido[1,2-a]pyrimidine-2-carboxamide To a solution of crude N-(4-fluorobenzyl)-3-hydroxy-8-[methoxy(methyl)amino]-4-oxo-6,7,8,9-tetrahydro-4H-pyrido[1,2-a]pyrimidine-2-carboxamide in acetic acid/water (2:1) was added zinc dust (300% in weight). The mixture was stirred at room temperature and after 1.5 h further zinc dust (300% in weight) was added. After 24 h zinc was filtered off and the filtrate was concentrated to dryness. The residue was dissolved in methanol and applied on a SCX resin cartridge. The cartridge was washed with water and methanol and then eluted with ammonia in methanol (2N). The eluent was concentrated to dryness. The crude product so obtained was used in the subsequent step without further purification.

MS m/z: 347 (M+H)$^+$.

Step 4: 8-[acetyl(methyl)amino]-N-(4-fluorobenzyl)-3-hydroxy-4-oxo-6,7,8,9-tetrahydro-4H-pyrido[1,2-a]pyrimidine-2-carboxamide A solution of crude N-(4-fluorobenzyl)-3-hydroxy-8-(methylamino)-4-oxo-6,7,8,9-tetrahydro-4H-pyrido[1,2-a]pyrimidine-2-carboxamide, 1-hydroxybenzotriazole (2 eq.), 1-(3-dimethylaminopropyl)-3-ethyl-carbodiimide hydrochloride (2 eq.), DIPEA (1 eq.) and acetic acid (2 eq) in dichloromethane was stirred for 16 h at room temperature. The solvent was removed under vacuum and the product was isolated by prep. RP-HPLC, using water (0.1% TFA) and acetonitrile (0.1% TFA) as eluents (column: C18). After lyophilization the product was obtained as a fluffy white material.

$^1$H-NMR (300 MHz, DMSO-d$_6$/TFA) δ: 9.33 (m, 1H), 7.36 (m, 2H), 7.14 (m, 2H), 4.76 (m, 0.6H), 4.55-4.10 (m, 3.4H), 3.85-3.62 (m, 1H), 3.13-2.63 (m, 5H), 2.15-1.85 (m, 5H). MS m/z: 389 (M+H)$^+$.

Table 1 below lists compounds of the present invention which have been prepared. The table provides the structure and name of each compound, the mass of its molecular ion plus 1 (M$^+$) or molecular ion minus 1 (M$^-$) as determined via FIA-MS, and the synthetic scheme employed to prepare the compound.

| Structure | Name | M+ | Scheme |
|---|---|---|---|
| 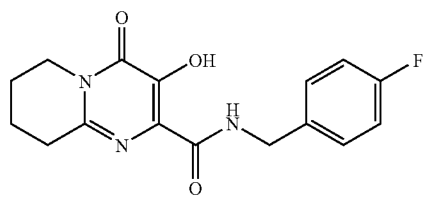 | N-(4-fluorobenzyl)-3-hydroxy-4-oxo-6,7,8,9-tetrahydro-4H-pyrido[1,2-a]pyrimidine-2-carboxamide | 318 | A (Ex. 1) |
| 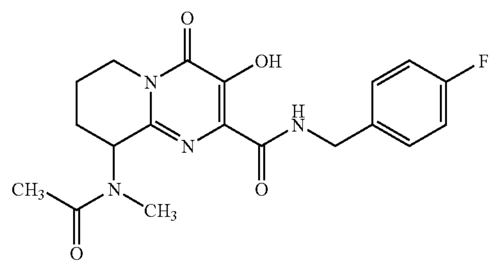 | 9-[acetyl(methyl)amino]-N-(4-fluorobenzyl)-3-hydroxy-4-oxo-6,7,8,9-tetrahydro-4H-pyrido[1,2-a]pyrimidine-2-carboxamide | 389 | C |
| 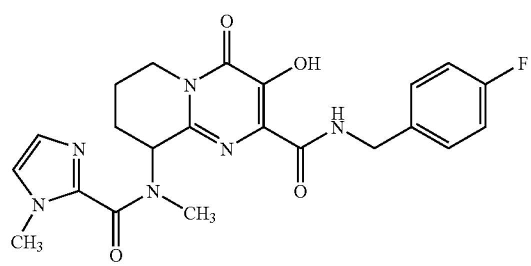 | N-(4-fluorobenzyl)-3-hydroxy-9-{methyl[(1-methyl-1H-imidazol-2-yl)carbonyl]amino}-4-oxo-6,7,8,9-tetrahydro-4H-pyrido[1,2-a]pyrimidine-2-carboxamide | 455 | C |
| 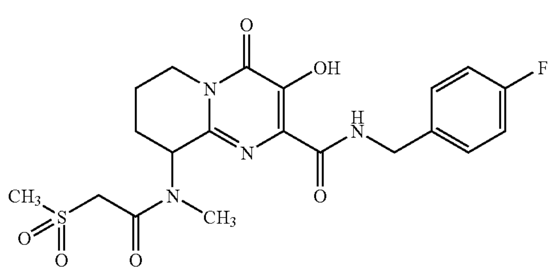 | N-(4-fluorobenzyl)-3-hydroxy-9-{methyl[(methylsulfonyl)acetyl]amino}-4-oxo-6,7,8,9-tetrahydro-4H-pyrido[1,2-a]pyrimidine-2-carboxamide | 467 | C |
| 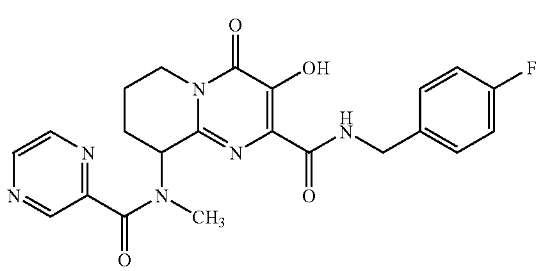 | N-(4-fluorobenzyl)-3-hydroxy-9-[methyl(pyrazin-2-ylcarbonyl)amino]-4-oxo-6,7,8,9-tetrahydro-4H-pyrido[1,2-a]pyrimidine-2-carboxamide | 453 | C |
| 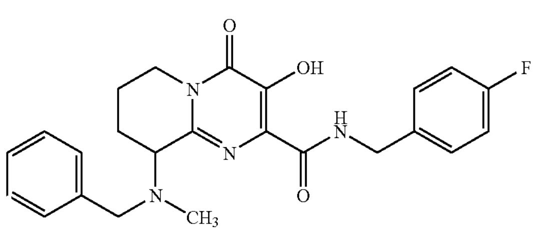 | 9-[benzyl(methyl)amino]-N-(4-fluorobenzyl)-3-hydroxy-4-oxo-6,7,8,9-tetrahydro-4H-pyrido[1,2-a]pyrimidine-2-carboxamide | 437 | B |

-continued

| Structure | Name | M+ | Scheme |
|---|---|---|---|
| 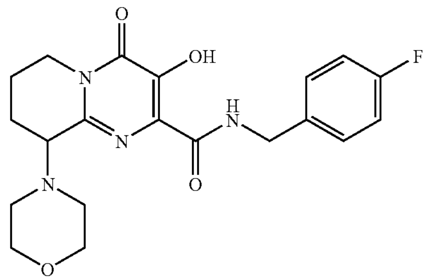 | N-(4-fluorobenzyl)-3-hydroxy-9-morpholin-4-yl-4-oxo-6,7,8,9-tetrahydro-4H-pyrido[1,2-a]pyrimidine-2-carboxamide | 403 | B (Ex. 2) |
| 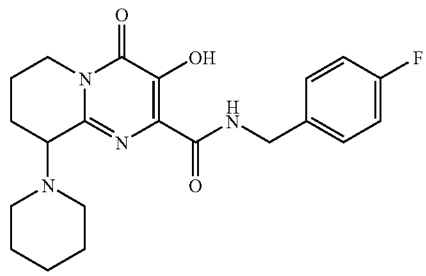 | N-(4-fluorobenzyl)-3-hydroxy-4-oxo-9-piperidin-1-yl-6,7,8,9-tetrahydro-4H-pyrido[1,2-a]pyrimidine-2-carboxamide | 401 | B |
| 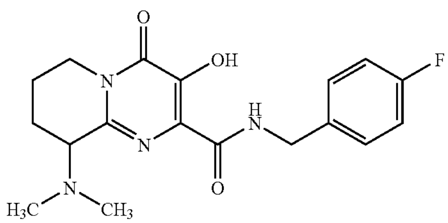 | 9-(dimethylamino)-N-(4-fluorobenzyl)-3-hydroxy-4-oxo-6,7,8,9-tetrahydro-4H-pyrido[1,2-a]pyrimidine-2-carboxamide | 361 | B |
| 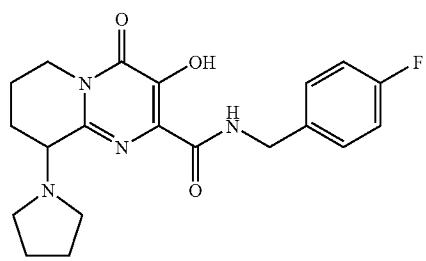 | N-(4-fluorobenzyl)-3-hydroxy-4-oxo-9-pyrrolidin-1-yl-6,7,8,9-tetrahydro-4H-pyrido[1,2-a]pyrimidine-2-carboxamide | 387 | B |
| 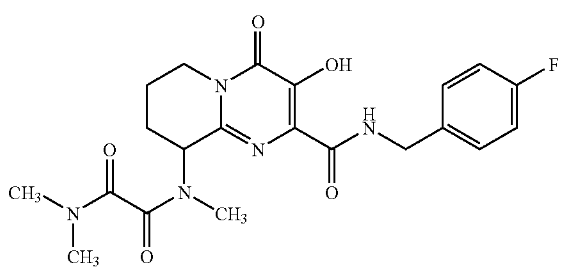 | N1-(2-{[(4-fluorobenzyl)amino]-carbonyl}-3-hydroxy-4-oxo-6,7,8,9-tetrahydro-4H-pyrido[1,2-a]pyrimidin-9-yl)-N1,N2,N2-trimethylethanediamide | 446 | C (Ex. 4) |
| 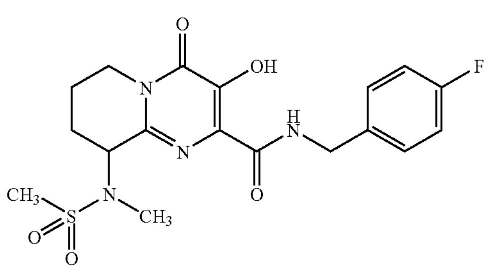 | N-(4-fluorobenzyl)-3-hydroxy-9-[methyl(methylsulfonyl)amino]-4-oxo-6,7,8,9-tetrahydro-4H-pyrido[1,2-a]pyrimidine-2-carboxamide | 425 | C |

-continued

| Structure | Name | M+ | Scheme |
|---|---|---|---|
| 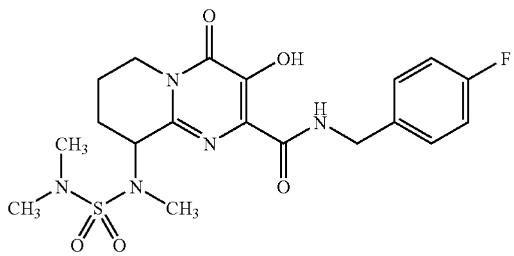 | 9-[[(dimethylamino)sulfonyl]-(methyl)amino]-N-(4-fluorobenzyl)-3-hydroxy-4-oxo-6,7,8,9-tetrahydro-4H-pyrido[1,2-a]pyrimidine-2-carboxamide | 454 | C (Ex. 3) |
| 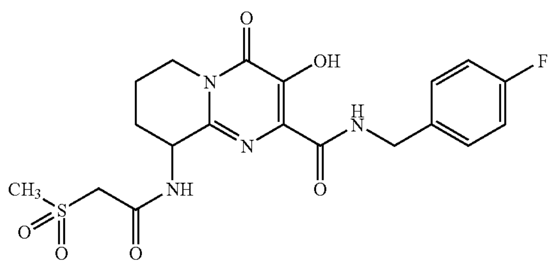 | N-(4-fluorobenzyl)-3-hydroxy-9-{[(methylsulfonyl)acetyl]amino}-4-oxo-6,7,8,9-tetrahydro-4H-pyrido[1,2-a]pyrimidine-2-carboxamide | 453 | C |
| 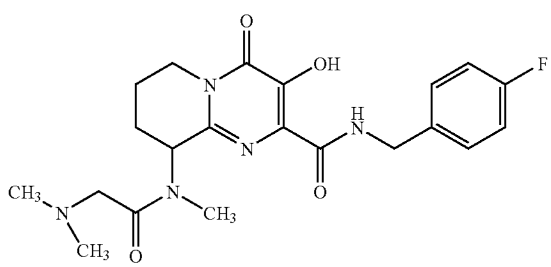 | 9-[(N,N-dimethylglycyl)(methyl)-amino]-N-(4-fluorobenzyl)-3-hydroxy-4-oxo-6,7,8,9-tetrahydro-4H-pyrido[1,2-a]pyrimidine-2-carboxamide | 432 | C |
| 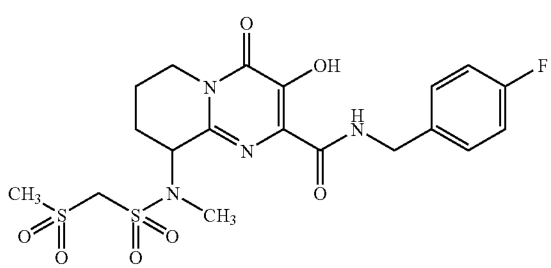 | N-(4-fluorobenzyl)-3-hydroxy-9-(methyl{[(methylsulfonyl)methyl]sulfonyl}amino)-4-oxo-6,7,8,9-tetrahydro-4H-pyrido[1,2-a]pyrimidine-2-carboxamide | 502 | C |
| 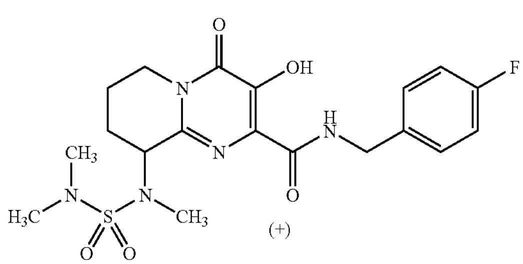 | (+)-9-[[(dimethylamino)sulfonyl]-(methyl)amino]-N-(4-fluorobenzyl)-3-hydroxy-4-oxo-6,7,8,9-tetrahydro-4H-pyrido[1,2-a]pyrimidine-2-carboxamide | 454 | D (Ex. 8) |
| 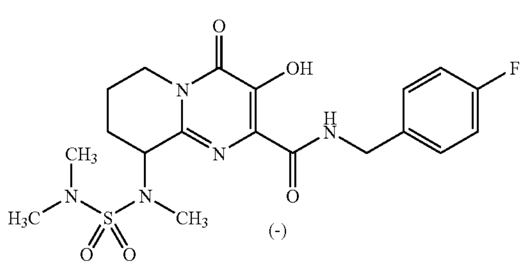 | (−)-9-[[(dimethylamino)sulfonyl]-(methyl)amino]-N-(4-fluorobenzyl)-3-hydroxy-4-oxo-6,7,8,9-tetrahydro-4H-pyrido[1,2-a]pyrimidine-2-carboxamide | 454 | D (Ex. 7) |

-continued

| Structure | Name | M+ | Scheme |
|---|---|---|---|
| 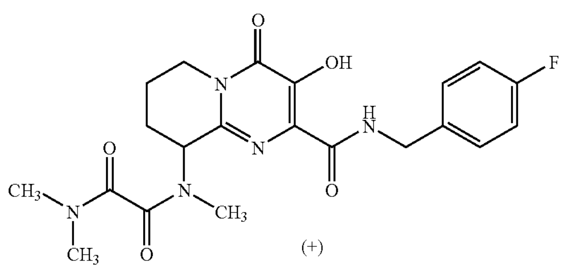 | (+)N1-(2-{[(4-fluorobenzyl)amino]-carbonyl}-3-hydroxy-4-oxo-6,7,8,9-tetrahydro-4H-pyrido[1,2-a]pyrimidin-9-yl)-N1,N2,N2-trimethylethanediamide | 446 | D (Ex. 5) |
| | (−)N1-(2-{[(4-fluorobenzyl)amino]-carbonyl}-3-hydroxy-4-oxo-6,7,8,9-tetrahydro-4H-pyrido[1,2-a]pyrimidin-9-yl)-N1,N2,N2-trimethylethanediamide | 446 | D (Ex. 6) |
| 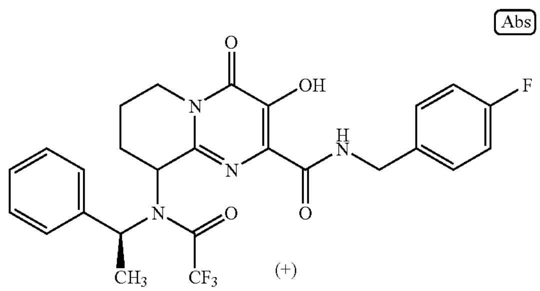 | (+)-N-(4-fluorobenzyl)-3-hydroxy-4-oxo-9-[[(1S)-1-phenylethyl](trifluoroacetyl)-amino]-6,7,8,9-tetrahydro-4H-pyrido[1,2-a]pyrimidine-2-carboxamide | 533 | C |
| 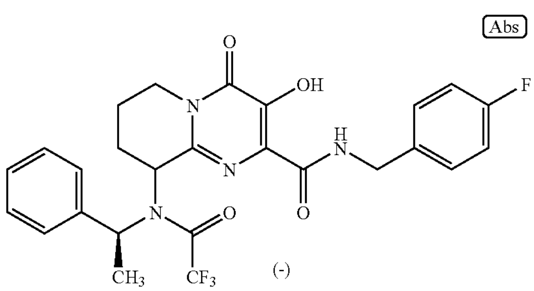 | (−)-N-(4-fluorobenzyl)-3-hydroxy-4-oxo-9-[[(1S)-1-phenylethyl](trifluoroacetyl)-amino]-6,7,8,9-tetrahydro-4H-pyrido[1,2-a]pyrimidine-2-carboxamide | 533 | C |
| 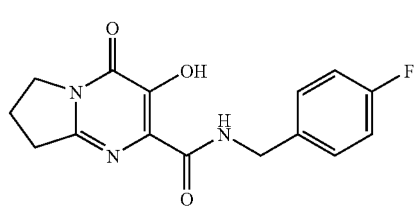 | N-(4-fluorobenzyl)-3-hydroxy-4-oxo-4,6,7,8-tetrahydropyrrolo[1,2-a]pyrimidine-2-carboxamide | 304 | A (Ex. 9) |
| 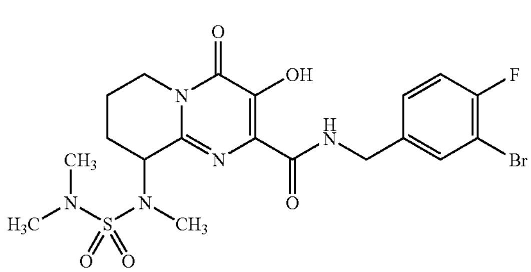 | N-(3-bromo-4-fluorobenzyl)-9-[[(dimethylamino)sulfonyl](methyl)amino]-3-hydroxy-4-oxo-6,7,8,9-tetrahydro-4H-pyrido[1,2-a]pyrimidine-2-carboxamide | 534 | C |

-continued

| Structure | Name | M+ | Scheme |
|---|---|---|---|
| 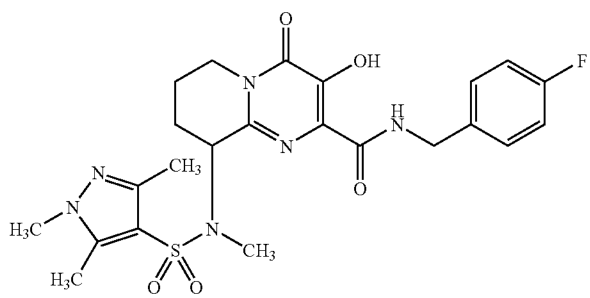 | N-(4-fluorobenzyl)-3-hydroxy-9-{methyl[(1,3,5-trimethyl-1H-pyrazol-4-yl)sulfonyl]amino}-4-oxo-6,7,8,9-tetrahydro-4H-pyrido[1,2-a]pyrimidine-2-carboxamide | 519 | C |
| 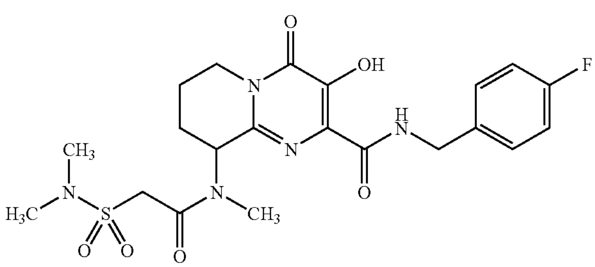 | 9-[{[(dimethylamino)sulfonyl]-acetyl}(methyl)amino]-N-(4-fluorobenzyl)-3-hydroxy-4-oxo-6,7,8,9-tetrahydro-4H-pyrido[1,2-a]pyrimidine-2-carboxamide | 496 | C |
| 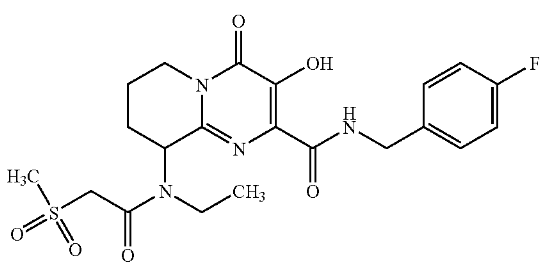 | 9-{ethyl[(methylsulfonyl)acetyl]-amino}-N-(4-fluorobenzyl)-3-hydroxy-4-oxo-6,7,8,9-tetrahydro-4H-pyrido[1,2-a]pyrimidine-2-carboxamide | 481 | C |
| 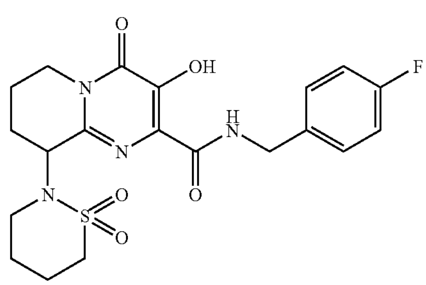 | 9-(1,1-dioxido-1,2-thiazinan-2-yl)-N-(4-fluorobenzyl)-3-hydroxy-4-oxo-6,7,8,9-tetrahydro-4H-pyrido[1,2-a]pyrimidine-2-carboxamide | 451 | C |
| 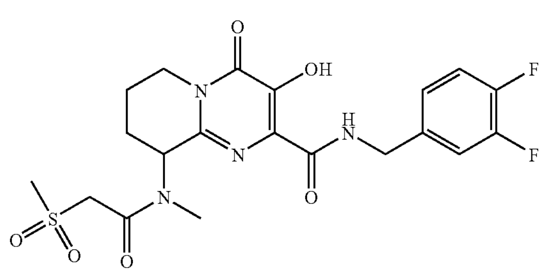 | N-(3,4-difluorobenzyl)-3-hydroxy-9-{methyl[(methylsulfonyl)acetyl]amino}-4-oxo-6,7,8,9-tetrahydro-4H-pyrido[1,2-a]pyrimidine-2-carboxamide | 485 | C |

-continued

| Structure | Name | M+ | Scheme |
|---|---|---|---|
| 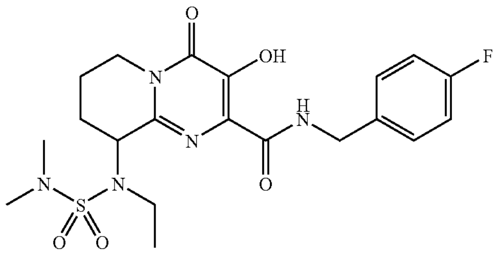 | 9-[[(dimethylamino)sulfonyl]-(ethyl)amino]-N-(4-fluorobenzyl)-3-hydroxy-4-oxo-6,7,8,9-tetrahydro-4H-pyrido[1,2-a]pyrimidine-2-carboxamide | 468 | C |
| (+) | (+)-N-(4-fluorobenzyl)-3-hydroxy-9-{methyl[(methylsulfonyl)acetyl]amino}-4-oxo-6,7,8,9-tetrahydro-4H-pyrido[1,2-a]pyrimidine-2-carboxamide | 467 | D |
| (−) | (−)-N-(4-fluorobenzyl)-3-hydroxy-9-{methyl[(methylsulfonyl)acetyl]amino}-4-oxo-6,7,8,9-tetrahydro-4H-pyrido[1,2-a]pyrimidine-2-carboxamide | 467 | D |
| 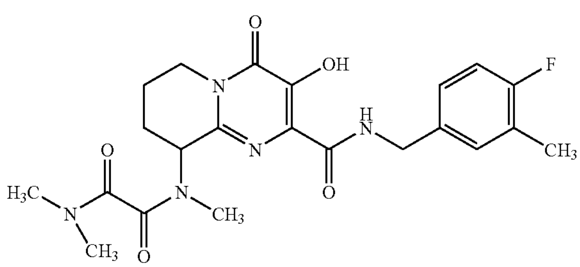 | N-(2-{[(4-fluoro-3-methylbenzyl)-amino]carbonyl}-3-hydroxy-4-oxo-6,7,8,9-tetrahydro-4H-pyrido[1,2-a]pyrimidin-9-yl)-N,N',N'-trimethylethanediamide | 460 | C |
| 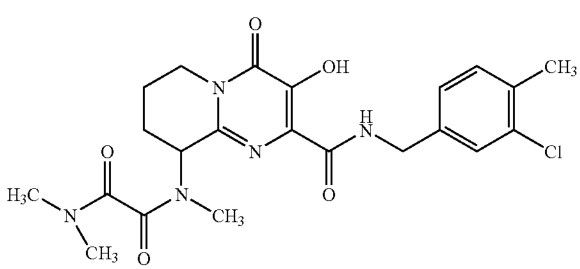 | N-(2-{[(3-chloro-4-methylbenzyl)-amino]carbonyl}-3-hydroxy-4-oxo-6,7,8,9-tetrahydro-4H-pyrido[1,2-a]pyrimidin-9-yl)-N,N',N'-trimethylethanediamide | 476 | C |
| | N-(2-{[(3-chlorobenzyl)amino]-carbonyl}-3-hydroxy-4-oxo-6,7,8,9-tetrahydro-4H-pyrido[1,2-a]pyrimidin-9-yl)-N,N',N'-trimethylethanediamide | 462 | C |

| Structure | Name | M+ | Scheme |
|---|---|---|---|
| 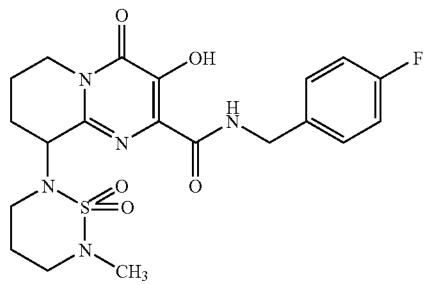 | N-(4-fluorobenzyl)-3-hydroxy-9-(6-methyl-1,1-dioxido-1,2,6-thiadiazinan-2-yl)-4-oxo-6,7,8,9-tetrahydro-4H-pyrido[1,2-a]pyrimidine-2-carboxamide | 466 | B |
| 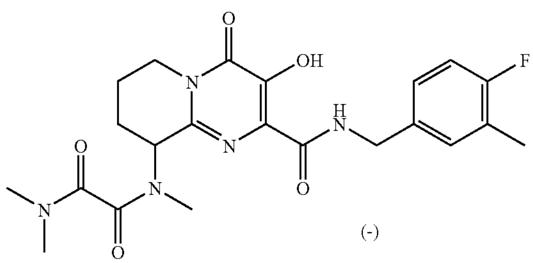 | (−)-N-(2-{[(4-fluoro-3-methylbenzyl)-amino]carbonyl}-3-hydroxy-4-oxo-6,7,8,9-tetrahydro-4H-pyrido[1,2-a]pyrimidin-9-yl)-N,N',N'-trimethylethanediamide | 460 | D |
| 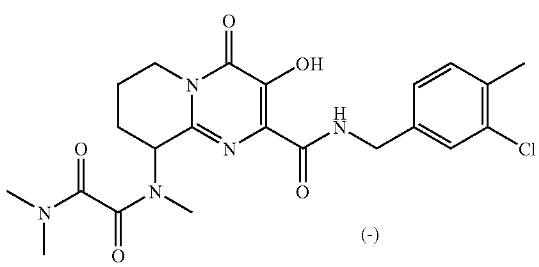 | (−)-N-(2-{[(3-chloro-4-methylbenzyl)-amino]carbonyl}-3-hydroxy-4-oxo-6,7,8,9-tetrahydro-4H-pyrido[1,2-a]pyrimidin-9-yl)-N,N',N'-trimethylethanediamide | 476 | D |
| 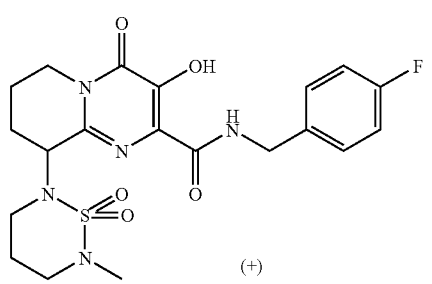 | (+)-N-(4-fluorobenzyl)-3-hydroxy-9-(6-methyl-1,1-dioxido-1,2,6-thiadiazinan-2-yl)-4-oxo-6,7,8,9-tetrahydro-4H-pyrido[1,2-a]pyrimidine-2-carboxamide | 466 | D |
| 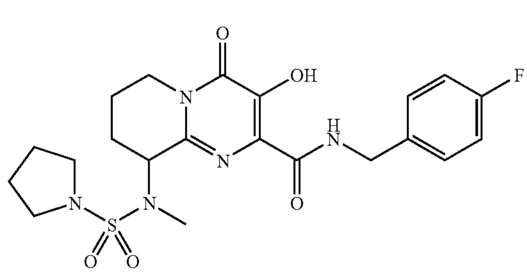 | N-(4-fluorobenzyl)-3-hydroxy-9-[methyl(pyrrolidin-1-ylsulfonyl)amino]-4-oxo-6,7,8,9-tetrahydro-4H-pyrido[1,2-a]pyrimidine-2-carboxamide | 480 | C |

-continued

| Structure | Name | M+ | Scheme |
|---|---|---|---|
| 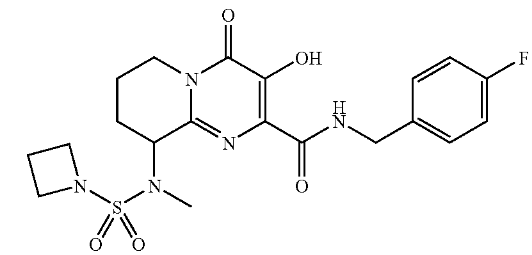 | 9-[(azetidin-1-ylsulfonyl)(methyl)-amino]-N-(4-fluorobenzyl)-3-hydroxy-4-oxo-6,7,8,9-tetrahydro-4H-pyrido[1,2-a]pyrimidine-2-carboxamide | 466 | C |
| 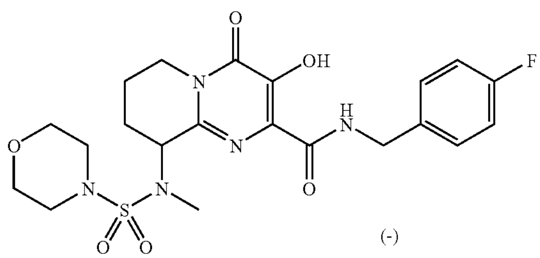 | (−)-N-(4-fluorobenzyl)-3-hydroxy-9-[methyl(morpholin-4-ylsulfonyl)-amino]-4-oxo-6,7,8,9-tetrahydro-4H-pyrido[1,2-a]pyrimidine-2-carboxamide | 496 | D |
| 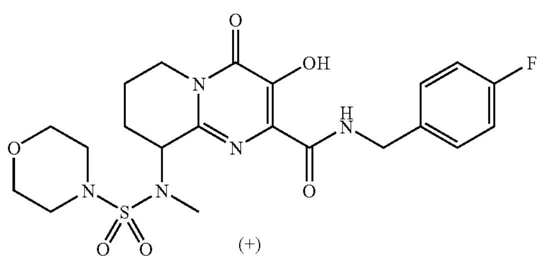 | (+)-N-(4-fluorobenyl)-3-hydroxy-9-[methyl(morpholin-4-ylsulfonyl)-amino]-4-oxo-6,7,8,9-tetrahydro-4H-pyrido[1,2-a]pyrimidine-2-carboxamide | 496 | D |
| 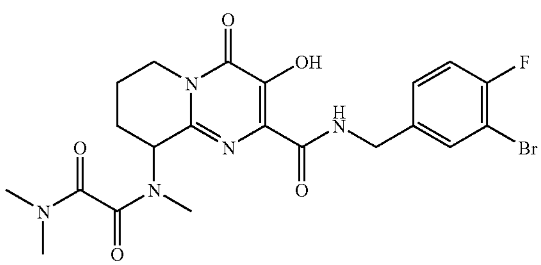 | N-(2-{[(3-bromo-4-fluorobenzyl)-amino]carbonyl}-3-hydroxy-4-oxo-6,7,8,9-tetrahydro-4H-pyrido[1,2-alpyrimidin-9-yl)-N,N',N'-trimethylethanediamide | 524/526 | C |
| 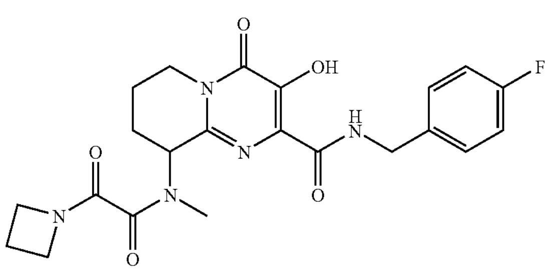 | 9-[[azetidin-1-yl(oxo)acetyl]-(methyl)amino]-N-(4-fluorobenzyl)-3-hydroxy-4-oxo-6,7,8,9-tetrahydro-4H-pyrido[1,2-a]pyrimidine-2-carboxamide | 458 | C |
| 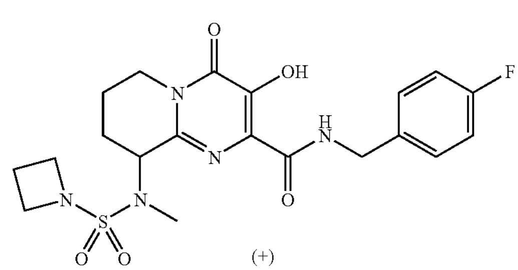 | (+)-9-[(azetidin-1-ylsulfonyl)(methyl)-amino]-N-(4-fluorobenzyl)-3-hydroxy-4-oxo-6,7,8,9-tetrahydro-4H-pyrido[1,2-a]pyrimidme-2-carboxamide | 466 | D |

| Structure | Name | M+ | Scheme |
|---|---|---|---|
| (−) | (−)-N-(2-{[(3-chloro-4-fluorobenzyl)amino]carbonyl}-3-hydroxy-4-oxo-6,7,8,9-tetrahydro-4H-pyrido[1,2-a]pyrimidin-9-yl)-N,N′,N′-trimethylethanediamide | 480 | D |
| (+) | (+)-N-(4-fluoro-3-methylbenzyl)-3-hydroxy-9-[methyl(morpholin-4-ylsulfonyl)amino]-4-oxo-6,7,8,9-tetrahydro-4H-pyrido[1,2-a]pyrimidine-2-carboxamide | 510 | D |
| (−) | (−)-9-[{[(dimethylamino)sulfonyl]acetyl}(methyl)amino]-N-(4-fluoro-3-methylbenzyl)-3-hydroxy-4-oxo-6,7,8,9-tetrahydro-4H-pyrido[1,2-a]pyrimidine-2-carboxamide | 510 | D |
| (−) | (−)-N-(4-fluorobenzyl)-3-hydroxy-9-{methyl[(4-methylpiperazin-1-yl)sulfonyl]amino}-4-oxo-6,7,8,9-tetrahydro-4H-pyrido[1,2-a]pyrimidine-2-carboxamide | 509 | D |
| (+) | (+)-N-(4-fluorobenzyl)-3-hydroxy-9-{methyl[(4-methylpiperazin-1-yl)sulfonyl]amino}-4-oxo-6,7,8,9-tetrahydro-4H-pyrido[1,2-a]pyrimidine-2-carboxamide | 509 | D |
| 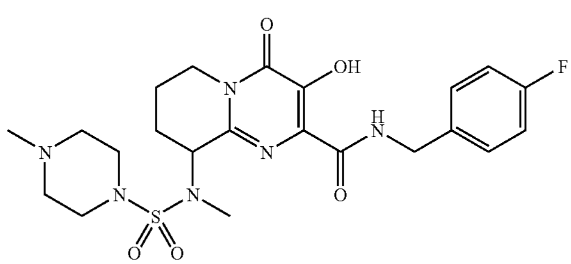 | N-(4-fluorobenzyl)-3-hydroxy-9-{methyl[(4-methylpiperazin-1-yl)sulfonyl]amino}-4-oxo-6,7,8,9-tetrahydro-4H-pyrido[1,2-a]pyrimidine-2-carboxamide | 509 | D |

-continued

| Structure | Name | M+ | Scheme |
|---|---|---|---|
| 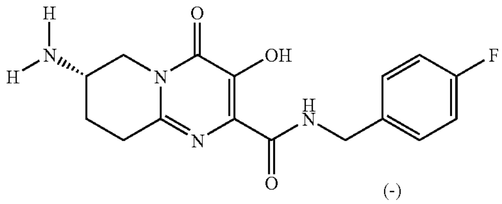 | (−)-(7S)-7-amino-N-(4-fluorobenzyl)-3-hydroxy-4-oxo-6,7,8,9-tetrahydro-4H-pyrido[1,2-a]pyrimidine-2-carboxamide | 333 | A (Ex. 13) |
| 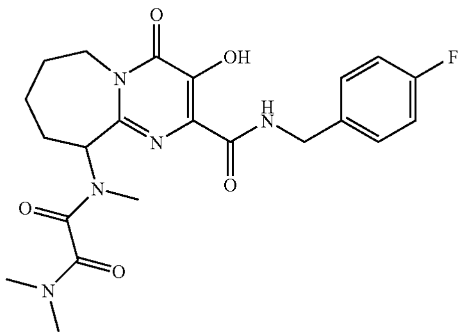 | N-(2-{[(4-fluorobenzyl)amino]-carbonyl}-3-hydroxy-4-oxo-4,6,7,8,9,10-hexahydropyrimido[1,2-a]azepin-10-yl)-N,N',N'-trimethylethanediamide | 460 | C (Ex. 11) |
| 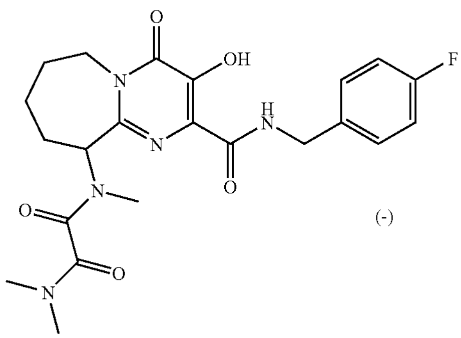 | (−)N-(2-{[(4-fluorobenzyl)amino]-carbonyl}-3-hydroxy-4-oxo-4,6,7,8,9,10-hexahydropyrimido[1,2-a]azepin-10-yl)-N,N',N'-trimethylethanediamide | 460 | D (Ex. 12) |
| 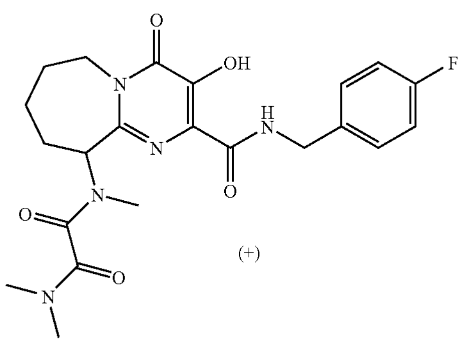 | (+)N-(2-{[(4-fluorobenzyl)amino]-carbonyl}-3-hydroxy-4-oxo-4,6,7,8,9,10-hexahydropyrimido[1,2-a]azepin-10-yl)-N,N',N'-trimethylethanediamide | 460 | D |
| 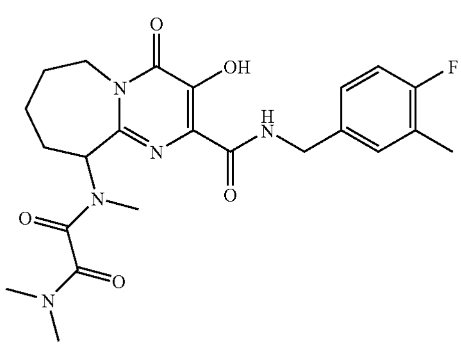 | N-(2-{[(4-fluoro-3-methylbenzyl)-amino]carbonyl}-3-hydroxy-4-oxo-4,6,7,8,9,10-hexahydropyrimido[1,2-a]azepin-10-yl)-N,N',N'-trimethylethanediamide | 474 | C |

-continued

| Structure | Name | M+ | Scheme |
|---|---|---|---|
| 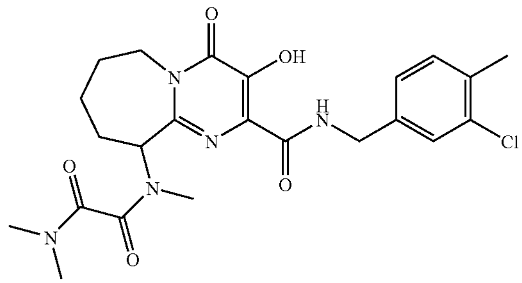 | N-(2-{[(3-chloro-4-methylbenzyl)-amino]carbonyl}-3-hydroxy-4-oxo-4,6,7,8,9,10-hexahydropyrimido[1,2-a]azepin-10-yl)-N,N',N'-trimethylethanediamide | 490 | C |
| | (+)-N-(2-{[(4-fluoro-3-methylbenzyl)-amino]carbonyl}-3-hydroxy-4-oxo-4,6,7,8,9,10-hexahydropyrimido[1,2-a]azepin-10-yl)-N,N',N'-trimethylethanediamide | 474 | D |
| 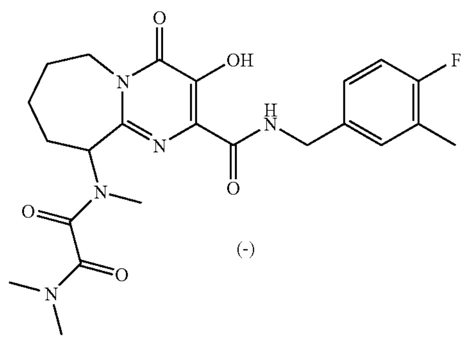 | (−)-N-(2-{[(4-fluoro-3-methylbenzyl)-amino]carbonyl}-3-hydroxy-4-oxo-4,6,7,8,9,10-hexahydropyrimido[1,2-a]azepin-10-yl)-N,N',N'-trimethylethanediamide | 474 | D |
| 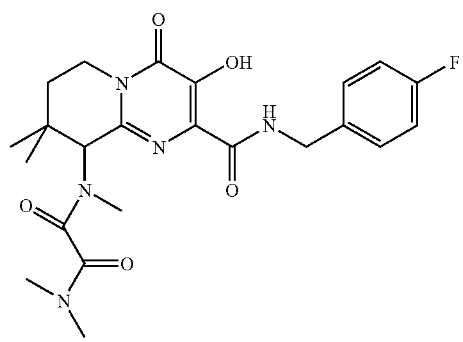 | N-(2-{[(4-fluorobenzyl)amino]-carbonyl}-3-hydroxy-8,8-dimethyl-4-oxo-6,7,8,9-tetrahydro-4H-pyrido[1,2-a]pyrimidin-9-yl)-N,N',N'-trimethylethanediamide | 474 | C |
| 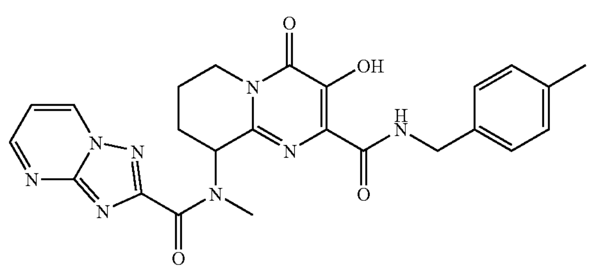 | N-(4-fluorobenzyl)-3-hydroxy-9-[methyl([1,2,4]triazolo[1,5-a]pyrimidin-2-ylcarbonyl)amino]-4-oxo-6,7,8,9-tetrahydro-4H-pyrido[1,2-a]pyrimidine-2-carboxamide | 493 | C |

-continued

| Structure | Name | M+ | Scheme |
|---|---|---|---|
| 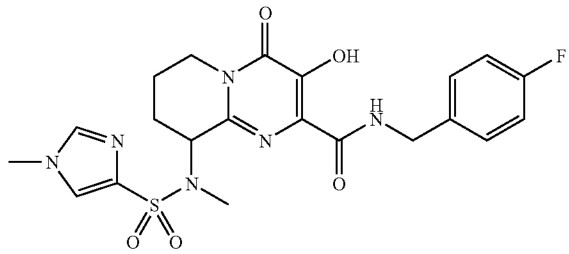 | N-(4-fluorobenzyl)-3-hydroxy-9-{methyl[(1-methyl-1H-imidazol-4-yl)sulfonyl]amino}-4-oxo-6,7,8,9-tetrahydro-4H-pyrido[1,2-a]pyrimidine-2-carboxamide | 491 | C |
| 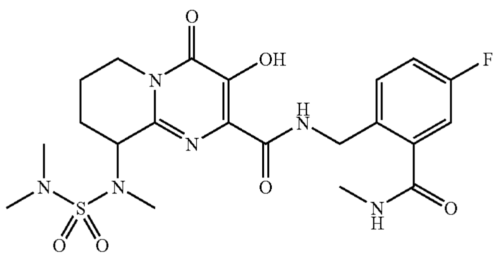 | 9-[[(dimethylamino)sulfonyl]-(methyl)amino]-N-{4-fluoro-2-[(methylamino)carbonyl]benzyl}-3-hydroxy-4-oxo-6,7,8,9-tetrahydro-4H-pyrido[1,2-a]pyrimidine-2-carboxamide | 511 | C |
| 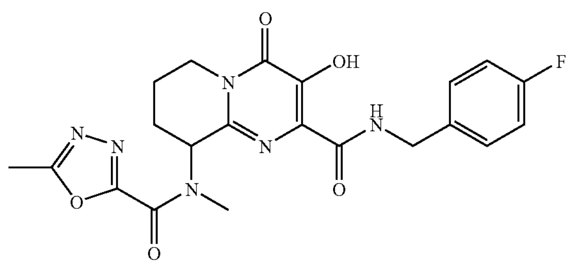 | N-(4-fluorobenzyl)-3-hydroxy-9-{methyl[(5-methyl-1,3,4-oxadiazol-2-yl)carbonyl]amino}-4-oxo-6,7,8,9-tetrahydro-4H-pyrido[1,2-a]pyrimidine-2-carboxamide | 457 | C |
| | 9-{[2-{dimethylamino}-2-oxoethyl]-thio}-N-(4-fluorobenzyl)-3-hydroxy-4-oxo-6,7,8,9-tetrahydro-4H-pyrido[1,2-a]pyrimidine-2-carboxamide | 435 | B |
| 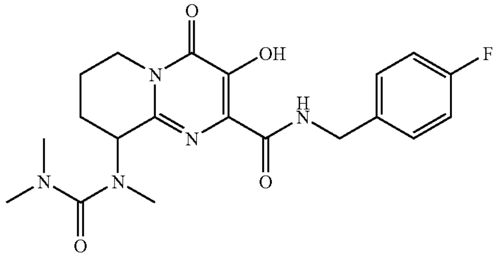 | 9-[[(dimethylamino)carbonyl]-(methyl)amino]-N-(4-fluorobenzyl)-3-hydroxy-4-oxo-6,7,8,9-tetrahydro-4H-pyrido[1,2-a]pyrimidine-2-carboxamide | 418 | C |

| Structure | Name | M+ | Scheme |
|---|---|---|---|
| 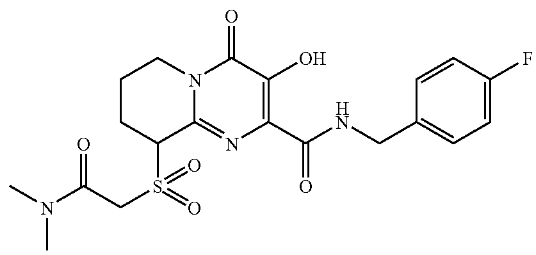 | 9-{[2-(dimethylamino)-2-oxoethyl]-sulfonyl}-N-(4-fluorobenzyl)-3-hydroxy-4-oxo-6,7,8,9-tetrahydro-4H-pyrido[1,2-a]pyrimidine-2-carboxamide | 467 | B |
| 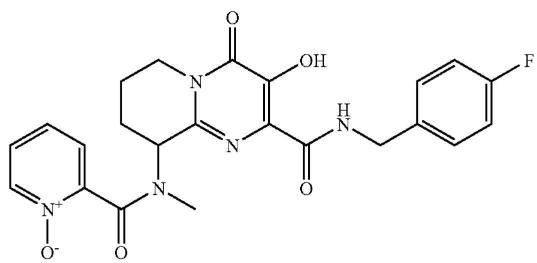 | N-(4-fluorobenzyl)-3-hydroxy-9-{methyl[(1-oxidopyridin-2-yl)carbonyl]amino}-4-oxo-6,7,8,9-tetrahydro-4H-pyrido[1,2-a]pyrimidine-2-carboxamide | 468 | C |
| 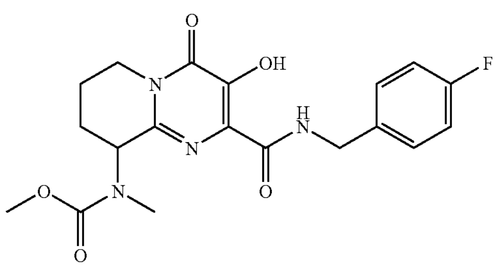 | methyl (2-{[(4-fluorobenzyl)-amino]carbonyl}-3-hydroxy-4-oxo-6,7,8,9-tetrahydro-4H-pyrido[1,2-a]pyrimidin-9-yl)methylcarbamate | 405 | C |
| 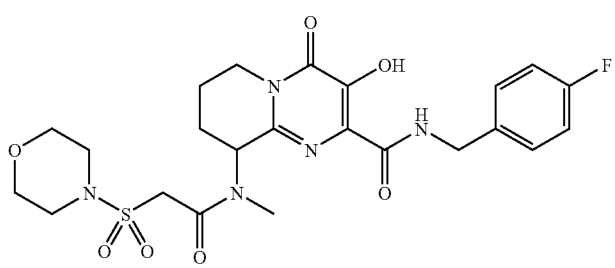 | N-(4-fluorobenzyl)-3-hydroxy-9-{methyl[(morpholin-4-ylsulfonyl)acetyl]amino}-4-oxo-6,7,8,9-tetrahydro-4H-pyrido[1,2-a]pyrimidine-2-carboxamide | 538 | C |
| 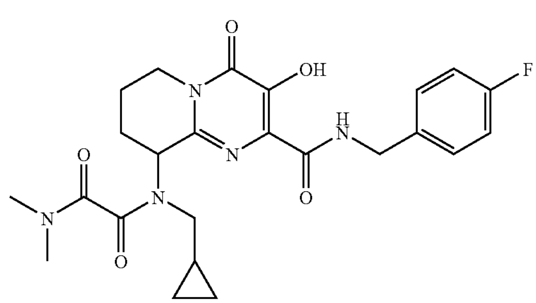 | N-(cyclopropylmethyl)-N-(2-{[(4-fluorobenzyl)amino]carbonyl}-3-hydroxy-4-oxo-6,7,8,9-tetrahydro-4H-pyrido[1,2-a]pyrimidin-9-yl)-N',N'-dimethylethanediamide | 486 | C |

-continued

| Structure | Name | M+ | Scheme |
|---|---|---|---|
| 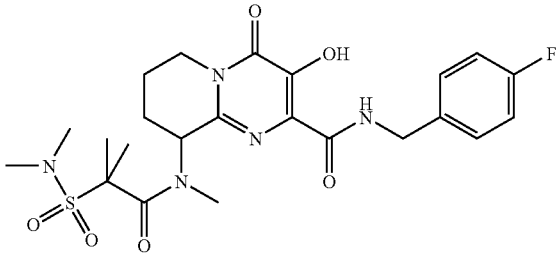 | 9-[{2-[(dimethylamino)sulfonyl]-2-methylpropanoyl}(methyl)amino]-N-(4-fluorobenzyl)-3-hydroxy-4-oxo-6,7,8,9-tetrahydro-4H-pyrido[1,2-a]pyrimidine-2-carboxamide | 524 | C |
| 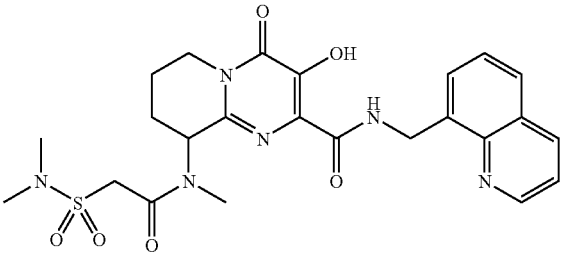 | 9-[{[(dimethylamino)sulfonyl]-acetyl}(methyl)amino]-3-hydroxy-4-oxo-N-(quinolin-8-ylmethyl)-6,7,8,9-tetrahydro-4H-pyrido[1,2-a]pyrimidine-2-carboxamide | 529 | C |
| 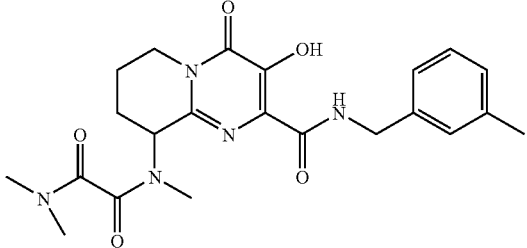 | N-(3-hydroxy-2-{[(3-methylbenzyl)-amino]carbonyl}-4-oxo-6,7,8,9-tetrahydro-4H-pyrido[1,2-a]pyrimidin-9-yl)-N,N',N'-trimethylethanediamide | 442 | C |
| 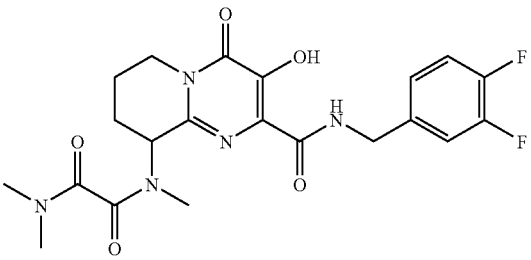 | N-(2-{[(3,4-difluorobenzyl)amino]-carbonyl}-3-hydroxy-4-oxo-6,7,8,9-tetrahydro-4H-pyrido[1,2-a]pyrimidin-9-yl)-N,N',N'-trimethylethanediamide | 464 | C |
| 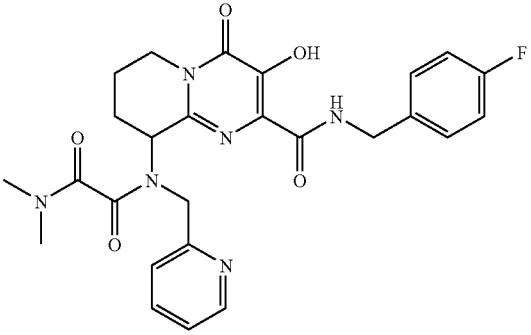 | N-(2-{[(4-fluorobenzyl)amino]-carbonyl}-3-hydroxy-4-oxo-6,7,8,9-tetrahydro-4H-pyrido[1,2-a]pyrimidin-9-yl)-N',N'-dimethyl-N-(pyridin-2-ylmethyl)ethanediamide | 523 | C |

-continued

| Structure | Name | M+ | Scheme |
|---|---|---|---|
| 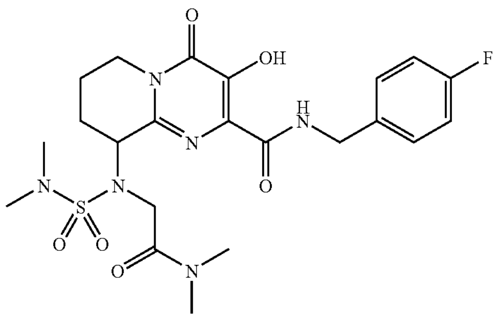 | 9-{(dimethylaminocarbonylmethyl)-[(dimethylamino)sulfonyl]amino}-N-(4-fluorobenzyl)-3-hydroxy-4-oxo-6,7,8,9-tetrahydro-4H-pyrido[1,2-a]pyrimidine-2-carboxamide | 525 | C |
| 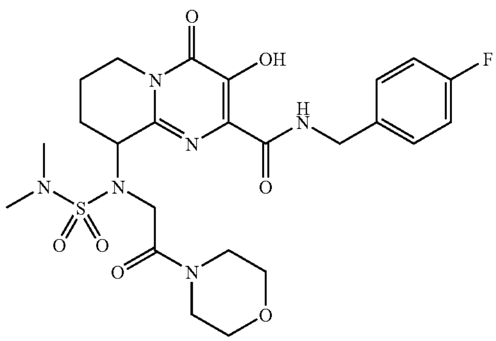 | 9{(4-morpholinylcarbonylmethyl)-(dimethylamino)sulfonyl]amino}-N-(4-fluorobenzyl)-3-hydroxy-4-oxo-6,7,8,9-tetrahydro-4H-pyrido[1,2-a]pyrimidine-2-carboxamide | 567 | C |
| 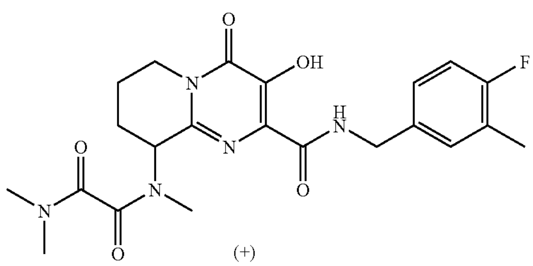 | (+)-N-(2-{[(4-fluoro-3-methylbenzyl)amino]carbonyl}-3-hydroxy-4-oxo-6,7,8,9-tetrahydro-4H-pyrido[1,2-a]pyrimidin-9-yl)-N,N',N'-trimethylethanediamide | 460 | D |
| 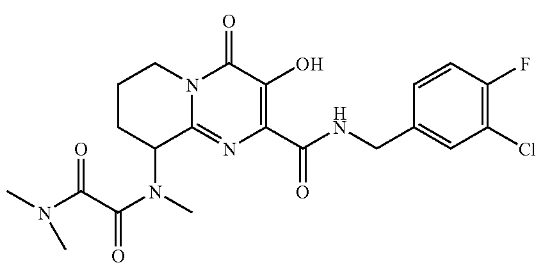 | N-(2-{[(3-chloro-4-fluorobenzyl)-amino]carbonyl}-3-hydroxy-4-oxo-6,7,8,9-tetrahydro-4H-pyrido[1,2-a]pyrimidin-9-yl)-N,N',N'-trimethylethanediamide | 480 | C |
| 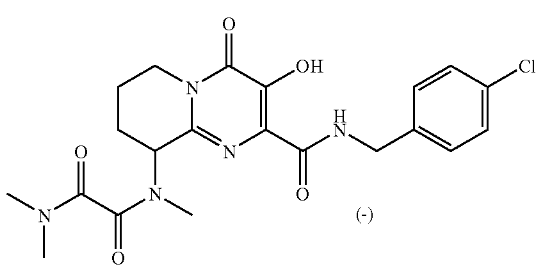 | (−)N-(2-{[(4-chlorobenzyl)amino]-carbonyl}-3-hydroxy-4-oxo-6,7,8,9-tetrahydro-4H-pyrido[1,2-a]pyrimidin-9-yl)-N,N',N'-trimethylethanediamide | 462 | D |

-continued

| Structure | Name | M+ | Scheme |
|---|---|---|---|
| 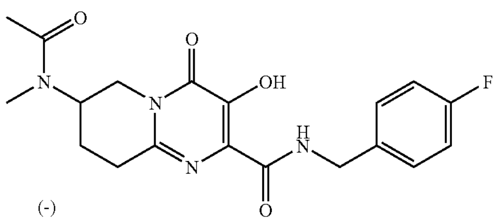 | (−)-(7S)-7-[acetyl(methyl)amino]-N-(4-fluorobenzyl)-3-hydroxy-4-oxo-6,7,8,9-tetrahydro-4H-pyrido[1,2-a]pyrimidine-2-carboxamide | 389 | C |
| 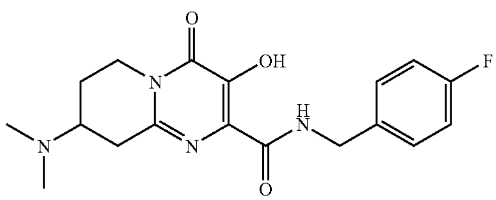 | 8-(dimethylamino)-N-(4-fluorobenzyl)-3-hydroxy-4-oxo-6,7,8,9-tetrahydro-4H-pyrido[1,2-a]pyrimidine-2-carboxamide | 361 | E |
| 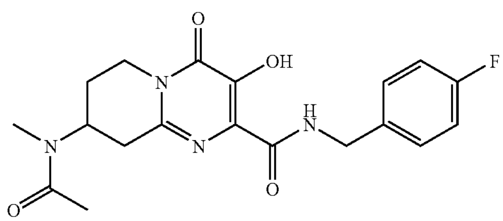 | 8-[acetyl(methyl)amino]-N-(4-fluorobenzyl)-3-hydroxy-4-oxo-6,7,8,9-tetrahydro-4H-pyrido[1,2-a]pyrimidine-2-carboxamide | 389 | E (Ex. 14) |
| 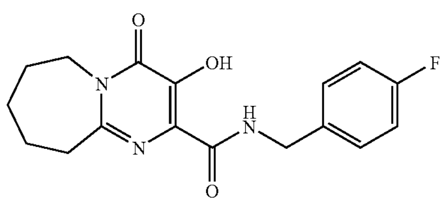 | N-(4-fluorobenzyl)-3-hydroxy-4-oxo-4,6,7,8,9,10-hexahydropyrimido[1,2-a]azepine-2-carboxamide | 332 | a |
| 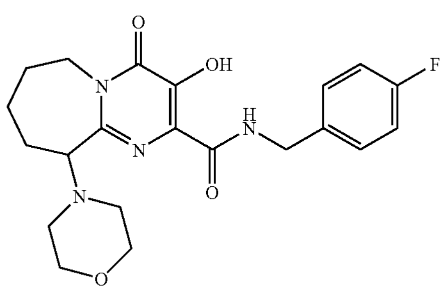 | N-(4-fluorobenzyl)-3-hydroxy-10-morpholin-4-yl-4-oxo-4,6,7,8,9,10-hexahydropyrimido[1,2-a]azepine-2-carboxamide | 417 | B |
| 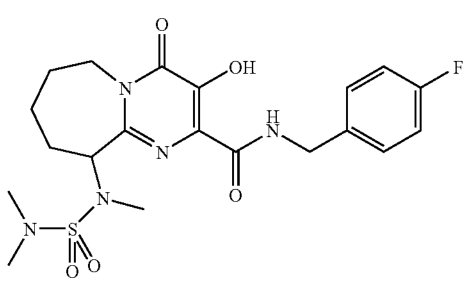 | 10-[[(dimethylamino)sulfonyl](methyl)-amino]-N-(4-fluorobenzyl)-3-hydroxy-4-oxo-4,6,7,8,9,10-hexahydropyrimido-[1,2-a]azepine-2-carboxamide | 468 | C |

-continued

| Structure | Name | M+ | Scheme |
|---|---|---|---|
| 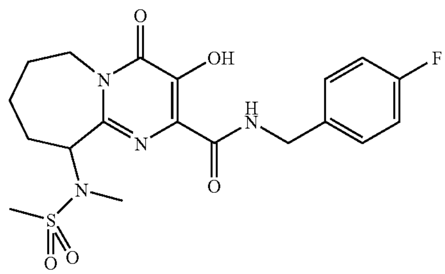 | N-(4-fluorobenzyl)-3-hydroxy-10-[methyl(methylsulfonyl)amino]-4-oxo-4,6,7,8,9,10-hexahydropyrimido-[1,2-a]azepine-2-carboxamide | 439 | C |
| 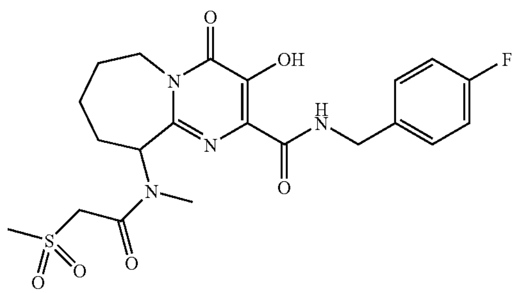 | N-(4-fluorobenzyl)-3-hydroxy-10-{methyl[(methylsulfonyl)acetyl]amino}-4-oxo-4,6,7,8,9,10-hexahydropyrimido[1,2-a]azepine-2-carboxamide | 481 | C |
| 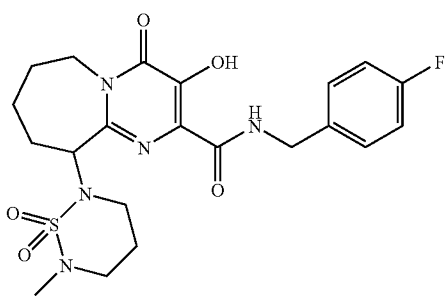 | N-(4-fluorobenzyl)-3-hydroxy-10-(6-methyl-1,1-dioxido-1,2,6-thiadiazinan-2-yl)-4-oxo-4,6,7,8,9,10-hexahydropyrimido[1,2-a]azepine-2-carboxamide | 480 | B |
| 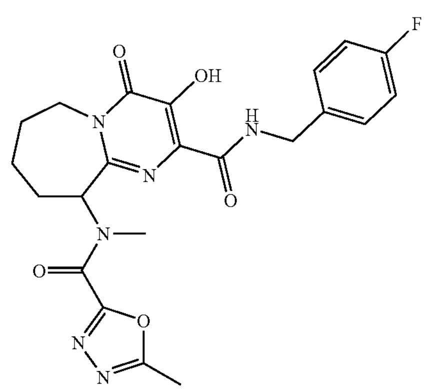 | N-(4-fluorobenzyl)-3-hydroxy-10-{methyl[(5-methyl-1,3,4-oxadiazol-2-yl)carbonyl]amino}-4-oxo-4,6,7,8,9,10-hexahydropyrimido[1,2-a]azepine-2-carboxamide | 471 | C |
| 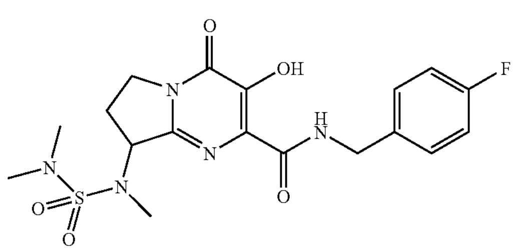 | 8-[[(dimethylamino)sulfonyl](methyl)-amino]-N-(4-fluorobenzyl)-3-hydroxy-4-oxo-4,6,7,8-tetrahydropyrrolo[1,2-a]pyrimidine-2-carboxamide | 440 | C (Ex. 10) |

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula A, or a pharmaceutically acceptable salt thereof:

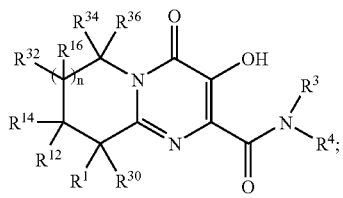

(A)

wherein $R^1$, $R^{12}$, and each $R^{16}$ are independently H, $NR^2R^5$, $OR^2$, $SR^2$, $SOR^2$, $SO_2R^2$, $SO_2NR^2R^5$, $OC(O)NR^2R^5$, $R^{11}$, $C_{1-6}$ alkyl, substituted alkyl, $SR^{18}$, $SO_2R^{18}$, or $N[SO_2N(C_{1-6}$ alkyl)$_2]R^{18}$; wherein substituted alkyl is $C_{1-6}$ alkyl substituted with O—$C_{1-6}$ alkyl, $C_{3-8}$ cycloalkyl, or aryl, wherein the cycloalkyl is optionally substituted with from 1 to 3 $C_{1-6}$ alkyl groups and the aryl is optionally substituted with from 1 to 5 substituents each of which is independently $C_{1-6}$ alkyl, O—$C_{1-6}$ alkyl, $CF_3$, $OCF_3$, halo, CN, or $NO_2$; with the proviso that no more than one of $R^1$, $R^{12}$ and $R^{16}$ is other than H, $C_{1-6}$ alkyl, or substituted alkyl;

$R^2$ is
1) H, or
2) $C_{1-6}$ alkyl which is optionally substituted with aryl, $C_{3-8}$ cycloalkyl, or a 5- or 6-membered heteroaromatic ring containing from 1 to 4 heteroatoms independently selected from N, O and S;

R5 is
1) H,
2) $C_{1-6}$ alkyl, optionally substituted at any carbon atom with halogen, aryl, $SO_2$—$C_{1-6}$ alkyl, $N(C_{1-6}$ alkyl)$_2$, or $SO_2NR^uR^v$, wherein $R^u$ and $R^v$ are each independently a $C_{1-6}$ alkyl group or $R^u$ and $R^v$ together with the N to which they are attached form a 4- to 7-membered saturated heterocyclic ring containing at least one carbon atom and from zero to 3 heteroatoms in addition to the N atom to which $R^u$ and $R^v$ are attached, wherein the additional heteroatoms are independently selected from N, O and S, and in which any ring S atom is optionally oxidized to SO or $SO_2$, and wherein the heterocyclic ring is optionally substituted with from 1 to 3 substituents each of which is independently a $C_{1-6}$ alkyl group,
3) $C(O)C_{1-6}$ alkyl, where the alkyl is optionally substituted at any carbon atom with halogen, aryl, $SO_2$—$C_{1-6}$ alkyl, $N(C_{1-6}$ alkyl)$_2$, or $SO_2NR^{u*}R^{v*}$, wherein $R^{u*}$ and $R^{v*}$ independently have the same definition as $R^u$ and $R^v$ respectively as set forth above,
4) C(O)—$C_{1-6}$ fluoroalkyl,
5) $C(O)R^7$,
6) $C(O)C(O)NR^8R^9$,
7) $SO_2NR^8R^9$,
8) $SO_2C_{1-6}$ alkyl, where the alkyl is optionally substituted at any carbon atom with halogen, aryl, $SO_2$—$C_{1-6}$ alkyl or $N(C_{1-6}$ alkyl)$_2$,
9) $C(O)NR^8R^9$,
10) $SO_2R^7$,
11) $C(O)C(O)R^{10}$, where $R^{10}$ is a 4- to 7-membered saturated heterocyclic ring containing at least one carbon atom and from 1 to 4 heteroatoms independently selected from N, O and S, and in which any ring S atom is optionally oxidized to SO or $SO_2$, and wherein the heterocyclic ring is optionally substituted with from 1 to 3 substituents each of which is independently a $C_{1-6}$ alkyl group,
12) $C(O)O$—$C_{1-6}$ alkyl, or
13) $SO_2R^{20}$, wherein $R^{20}$ is a saturated heterocyclic ring independently having the same definition as $R^{10}$ set forth above;

or alternatively $R^2$ and $R^5$ together with the nitrogen atom to which they are attached form a 4- to 7-membered saturated heterocyclic ring containing at least one carbon atom and from zero to 3 heteroatoms in addition to the N atom to which $R^2$ and $R^5$ are attached, wherein the additional heteroatoms are independently selected from N, O and S, and in which any ring S atom is optionally oxidized to SO or $SO_2$, and wherein the heterocyclic ring is optionally substituted with from 1 to 3 substituents each of which is independently a $C_{1-6}$ alkyl group;

$R^7$ and $R^{11}$ are each independently a 5- or 6-membered unsaturated heterocyclic ring or an unsaturated 9- or 10-membered heterobicyclic fused ring system, wherein the ring or bicyclic ring system contains from 1 to 4 heteroatoms independently selected from N, O and S, and in which any one or more of the N and S atoms is optionally oxidized, and wherein the ring is optionally substituted with from 1 to 3 substituents each of which is independently a $C_{1-6}$ alkyl group;

$R^8$ and $R^9$ are each independently selected from the group consisting of $C_{1-6}$ alkyl and aryl;

$R^{14}$, $R^{30}$, each $R^{32}$, $R^{34}$ and $R^{36}$ are independently:
(1) H,
(2) $C_{1-6}$ alkyl, or
(3) $C_{1-6}$ alkyl substituted with O—$C_{1-6}$ alkyl, $C_{3-8}$ cycloalkyl, or aryl, wherein the cycloalkyl is optionally substituted with from 1 to 3 $C_{1-6}$ alkyl groups and the aryl is optionally substituted with from 1 to 5 substituents each of which is independently $C_{1-6}$ alkyl, O—$C_{1-6}$ alkyl, $CF_3$, $OCF_3$, halo, CN, or $NO_2$;

$R^{18}$ is $C_{1-6}$ alkyl substituted with $C(O)NR^wR^x$, wherein $R^w$ and $R^x$ are each independently a $C_{1-6}$ alkyl group or $R^w$ and $R^x$ together with the N to which they are attached form a 4- to 7-membered saturated heterocyclic ring containing at least one carbon atom and from zero to 3 heteroatoms in addition to the N atom to which $R^w$ and $R^x$ are attached, wherein the additional heteroatoms are independently selected from N, O and S, and wherein any of the ring S atoms is optionally oxidized to SO or $SO_2$, and wherein the saturated heterocyclic ring is optionally substituted with from 1 to 3 substituents each of which is independently a $C_{1-6}$ alkyl group;

$R^3$ is H or $C_{1-6}$ alkyl;

$R^4$ is
1) hydrogen,
2) $C_{1-6}$ alkyl which is optionally substituted with one or more substituents each of which is independently halogen, OH, O—$C_{1-6}$ alkyl, O—$C_{1-6}$ haloalkyl, $NO_2$, $N(R^aR^b)$, $C(O)R^a$, $CO_2R^a$, $SR^a$, $S(O)R^a$, $SO_2R^a$, or $N(R^a)CO_2R^b$,
3) $C_{1-6}$ alkyl which is optionally substituted with one or more substituents each of which is independently halogen, OH, or O—$C_{1-4}$ alkyl, and which is substituted with 1 or 2 substituents each of which is independently:
i) $C_{3-8}$ cycloalkyl,
ii) aryl,
iii) a fused bicyclic carbocycle consisting of a benzene ring fused to a $C_{5-7}$ cycloalkyl,
iv) a 5- or 6-membered saturated heterocyclic ring containing from 1 to 4 heteroatoms independently selected from N, O and S,
v) a 5- or 6-membered heteroaromatic ring containing from 1 to 4 heteroatoms independently selected from N, O and S, or
vi) a 9- or 10-membered fused bicyclic heterocycle containing from 1 to 4 heteroatoms independently selected from N, O and S, wherein at least one of the rings is aromatic,
4) $C_{2-5}$ alkynyl optionally substituted with aryl,
5) $C_{3-8}$ cycloalkyl optionally substituted with aryl,
6) aryl,
7) a fused bicyclic carbocycle consisting of a benzene ring fused to a $C_{5-7}$ cycloalkyl,
8) a 5- or 6-membered saturated heterocyclic ring containing from 1 to 4 heteroatoms independently selected from N, O and S,
9) a 5- or 6-membered heteroaromatic ring containing from 1 to 4 heteroatoms independently selected from N, O and S, or
10) a 9- or 10-membered fused bicyclic heterocycle containing from 1 to 4 heteroatoms independently selected from N, O and S, wherein at least one of the rings is aromatic;
wherein
each aryl in (3)(ii) or the aryl (4), (5) or (6) or each fused carbocycle in (3)(iii) or the fused carbocycle in (7) is optionally substituted with one or more substituents each of which is independently halogen, OH, $C_{1-6}$ alkyl, —$C_{1-6}$ alkylene-$OR^a$, $C_{1-6}$ haloalkyl, O—$C_{1-6}$ alkyl, O—$C_{1-6}$ haloalkyl, CN, $NO_2$, $N(R^a R^b)$, —$C_{1-6}$ alkylene-$N(R^a R^b)$, $C(O)N(R^a R^b)$, $C(O)R^a$, $CO_2R^a$, —$C_{1-6}$ alkylene-$CO_2R^a$, $OCO_2R^a$, $SR^a$, $S(O)R^a$, $SO_2R^a$, $N(R^a)SO_2R^b$, $SO_2N(R^a R^b)$, $N(R^a)C(O)R^b$, $N(R^a)CO_2R^b$, —$C_{1-6}$ alkylene-$N(R^a)CO_2R^b$, aryl, —$C_{1-6}$ alkylene-aryl, O-aryl, or —$C_{0-6}$ alkylene-HetA wherein HetA is a 5- or 6-membered heteroaromatic ring containing from 1 to 4 heteroatoms independently selected from N, O and S, and the heteroaromatic ring is optionally fused with a benzene ring, and is optionally substituted with one or more substituents each of which is independently $C_{1-6}$ alkyl, $C_{1-6}$ haloalkyl, O—$C_{1-6}$ alkyl, O—$C_{1-6}$ haloalkyl, OH, or $CO_2R^a$;
each saturated heterocyclic ring in (3)(iv) or the saturated heterocyclic ring in (8) is optionally substituted with one or more substituents each of which is independently halogen, $C_{1-6}$ alkyl, $C_{1-6}$ haloalkyl, O—$C_{1-6}$ alkyl, O—$C_{1-6}$ haloalkyl, oxo, aryl, or a 5- or 6-membered heteroaromatic ring containing from 1 to 4 heteroatoms independently selected from N, O and S; and
each heteroaromatic ring in (3)(v) or the heteroaromatic ring in (9) or each fused bicyclic heterocycle in (3)(vi) or the fused bicyclic heterocycle in (10) is optionally substituted with one or more substituents each of which is independently halogen, $C_{1-6}$ alkyl, $C_{1-6}$ haloalkyl, O—$C_{1-6}$ alkyl, O—$C_{1-6}$ haloalkyl, OH, aryl, or $C_{1-6}$ alkylene-aryl;

or alternatively $R^3$ and $R^4$ together with the nitrogen to which both are attached form a $C_{3-7}$ azacycloalkyl which is optionally substituted with one or more substituents each of which is independently $C_{1-6}$ alkyl or oxo;
each $R^a$ and $R^b$ is independently hydrogen or $C_{1-6}$ alkyl; and
n is an integer equal to 1.

2. A compound according to claim 1, or a pharmaceutically acceptable salt thereof, which is a compound of Formula I:

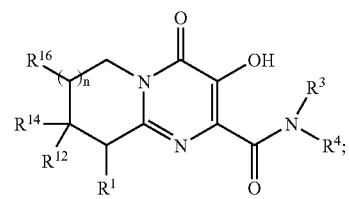

(I)

wherein
$R^1$, $R^{12}$, and each $R^{16}$ are independently H, $NR^2R^5$, $OR^2$, $SR^2$, $SOR^2$, $SO_2R^2$, $SO_2NR^2R^5$, $OC(O)NR^2R^5$, $R^{11}$, $C_{1-6}$ alkyl, $SR^{18}$, $SO_2R^{18}$, or $N[SO_2N(C_{1-6} \text{alkyl})_2]R^{18}$; with the proviso that no more than one of $R^1$, $R^{12}$, and each $R^{16}$ is other than H or $C_{1-6}$ alkyl; and
$R^{14}$ is H or $C_{1-6}$ alkyl.

3. A compound of formula:

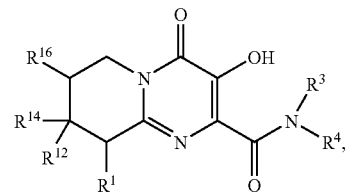

or a pharmaceutically acceptable salt thereof, wherein:
$R^1$, $R^{12}$, and each $R^{16}$ are independently H, $NR^2R^5$, $OR^2$, $SR^2$, $SOR^2$, $SO_2R^2$, $SO_2NR^2R^5$, $OC(O)NR^2R^5$, $R^{11}$, $CH_3$, $SR^{18}$, $SO_2R^{18}$, or $N[SO_2N(C_{1-3} \text{alkyl})_2]R^{18}$; with the proviso that no more than one of $R^1$, $R^{12}$, and $R^{16}$ is other than H or $CH_3$;
$R^2$ is H, $CH_3$, $CH_2CH_3$, $CH_2$-cyclopropyl, $CH_2$-phenyl, $CH(CH)_3$-phenyl, or $CH_2$-pyridinyl;
$R^5$ is
1) H,
2) $C_{1-3}$ alkyl, optionally substituted at any carbon atom with halogen, phenyl, $SO_2CH_3$, $N(CH_3)_2$, or $SO_2N(CH_3)_2$,
3) $C(O)$—$C_{1-3}$ alkyl, where the alkyl group is optionally substituted with halogen, phenyl, $SO_2CH_3$, $N(CH_3)_2$, or $SO_2NR^{u*}R^{v*}$ wherein $R^{u*}$ and $R^{v*}$ are either both $CH_3$ or together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or $SO_2$,
4) $C(O)CF_3$,
5) $C(O)R^7$,

6) C(O)C(O)NR⁸R⁹,

7) SO₂NR⁸R⁹,

8) SO₂—C₁₋₃ alkyl, where the alkyl is optionally substituted with halogen, phenyl, SO₂CH₃ or N(CH₃)₂,

9) C(O)NR⁸R⁹,

10) SO₂R⁷,

11) C(O)C(O)R¹⁰, where R¹⁰ is a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is attached to the rest of the compound via a ring nitrogen and is optionally substituted with from 1 to 3 methyl groups, and wherein any ring S is optionally oxidized to SO or SO₂, 12) C(O)OCH₃, or 13) SO₂R²⁰, wherein R²⁰ is a saturated heterocyclic ring independently having the same definition as R¹⁰ set forth above;

or alternatively R² and R⁵ together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or SO₂;

R⁷ and R¹¹ are each independently an unsaturated heterocycle selected from the group consisting of pyrrolyl, pyrazolyl, imidazolyl, triazolyl, tetrazolyl, oxadiazolyl, pyridinyl, pyrazinyl, pyridazinyl, pyrimidinyl, furyl, thiazolyl, isothiazolyl, oxazolyl, isoxazolyl, quinolinyl, isoquinolinyl, quinazolinyl, cinnolinyl, and triazolopyrimidinyl, in which any one of the N atoms is optionally oxidized and wherein the heterocycle is optionally substituted with from 1 to 3 substituents each of which is methyl;

R⁸ and R⁹ are independently selected from the group consisting of CH₃ and phenyl;

R¹⁴ is H or CH₃;

R¹⁸ is CH₂C(O)NRʷRˣ wherein Rʷ and Rˣ are either both CH₃ or together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or SO₂;

R³ is hydrogen or CH₃; and

R⁴ is C₁₋₃ alkyl substituted with an aryl selected from phenyl and naphthyl or with a heteroaryl selected from pyridinyl, pyrimidinyl, pyrazinyl, quinazolinyl, cinnolinyl, quinolinyl, and isoquinolinyl, wherein the aryl or heteroaryl is optionally substituted with from 1 to 3 substituents each of which is independently halo, CH₃, CF₃, SO₂CH₃, or C(O)NH(CH₃).

4. A compound according to claim 3, or a pharmaceutically acceptable salt thereof, which is a compound of Formula II:

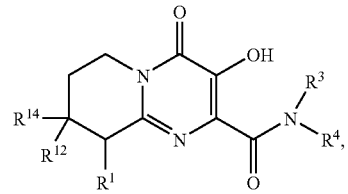

wherein R¹ is H, NR²R⁵, OR², SR², SOR², SO₂R², SO₂NR²R⁵, OC(O)NR²R⁵, R¹¹, SR¹⁸, SO₂R¹⁸, or N[SO₂N(CH₃)₂]R¹⁸;

R⁵ is

1) C₁₋₃ alkyl, optionally substituted at any carbon atom with halogen, phenyl, SO₂CH₃, N(CH₃)₂, or SO₂N(CH₃)₂, 2) C(O)—C₁₋₃ alkyl, where the alkyl group is optionally substituted with halogen, phenyl, SO₂CH₃, N(CH₃)₂, or SO₂NRᵘ*Rᵛ* wherein Rᵘ* and Rᵛ* are either both CH₃ or together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or SO₂,

3) C(O)CF₃,

4) C(O)R⁷,

5) C(O)C(O)NR⁸R⁹,

6) SO₂NR⁸R⁹,

7) SO₂—C₁₋₃ alkyl, where the alkyl is optionally substituted with halogen, phenyl, SO₂CH₃ or N(CH₃)₂,

8) C(O)NR⁸R⁹,

9) SO₂R⁷,

10) C(O)C(O)R¹⁰, where R¹⁰ is a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is attached to the rest of the compound via a ring nitrogen and is optionally substituted with from 1 to 3 methyl groups, and wherein any ring S is optionally oxidized to SO or SO₂, 11) C(O)OCH₃, or 12) SO₂R²⁰, wherein R²⁰ is a saturated heterocyclic ring independently having the same definition as R¹⁰ set forth above;

or alternatively R² and R⁵ together with the nitrogen atom to which they are attached form a saturated heterocyclic ring selected from the group consisting of azetidinyl, pyrrolidinyl, piperidinyl, morpholinyl, thiomorpholinyl, imidazolidinyl, oxazolidinyl, isoxazolidinyl, thiazolidinyl, isothiazolidinyl, thiazinanyl, thiadiazinanyl, and piperazinyl, wherein the saturated heterocyclic ring is optionally substituted with from 1 to 3 methyl groups, and wherein any ring S is optionally oxidized to SO or SO₂;

R¹² is H or CH₃; and

R¹⁴ is H or CH₃.

5. A compound according to claim 4, or a pharmaceutically acceptable salt thereof, wherein:
R$^3$ is hydrogen; and
R$^4$ is:

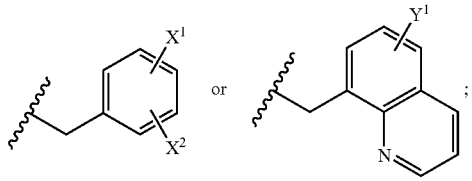

wherein X$^1$ and X$^2$ are each independently hydrogen, bromo, chloro, fluoro, CH$_3$, CF$_3$, SO$_2$CH$_3$, or C(O)NH(CH$_3$); and Y$^1$ is hydrogen, bromo, chloro, fluoro, CH$_3$, or CF$_3$.

6. A compound according to claim 5, or a pharmaceutically acceptable salt thereof, wherein
R$^1$ is H, NR$^2$R$^5$, SCH$_2$C(O)N(CH$_3$)$_2$, SO$_2$CH$_2$C(O)N(CH$_3$)$_2$, or N[SO$_2$N(CH$_3$)$_2$]CH$_2$C(O)N(CH$_3$)$_2$;
R$^5$ is
1) CH$_3$,
2) CH$_2$-phenyl,
3) C(O)CH$_3$,
4) C(O)CH$_2$SO$_2$CH$_3$,
5) C(O)CH$_2$SO$_2$N(CH$_3$)$_2$,
6) C(O)C(CH$_3$)$_2$—SO$_2$N(CH$_3$)$_2$,
7) C(O)CH$_2$N(CH$_3$)$_2$,
8) C(O)CF$_3$,
9) SO$_2$CH$_3$,
10) SO$_2$N(CH$_3$)$_2$,
11) C(O)C(O)N(CH$_3$)$_2$,
12) C(O)N(CH$_3$)$_2$,
13) SO$_2$CH$_2$SO$_2$CH$_3$,
14) C(O)OCH$_3$,
15) C(O)-T, wherein T is:

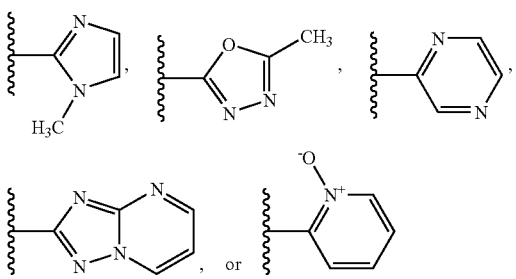

16)

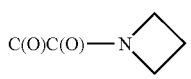

17)

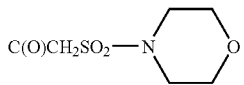

C(O)CH$_2$SO$_2$—

18) SO$_2$-Q, wherein Q is:

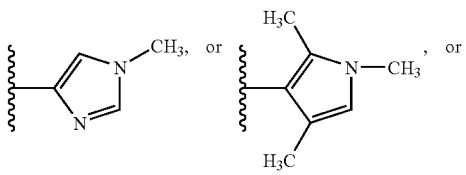

19) SO$_2$R$^{20}$, wherein R$^{20}$ is:

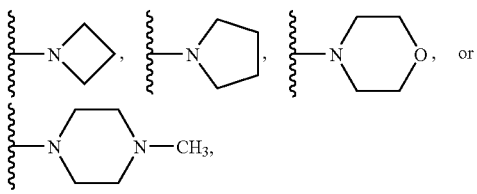

or alternatively R$^2$ and R$^5$ together with the nitrogen atom to which they are attached form a saturated heterocyclic ring selected from the group consisting of

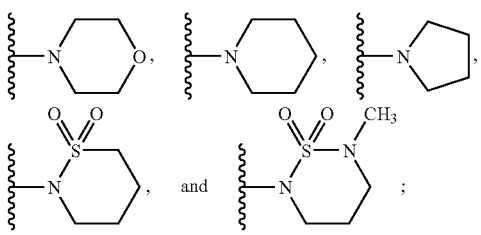

R$^4$ is:
1) p-fluorobenzyl,
2) 3-bromo-4-fluorobenzyl,
3) 3-chloro-4-fluorobenzyl,
4) 4-fluoro-3-methylbenzyl,
5) 3,4-difluorobenzyl,
6) 3-chlorobenzyl,
7) p-chlorobenzyl,
8) 3-chloro-4-methylbenzyl,
9) 3-methylbenzyl,
10) 4-fluoro-2[(methylamino)carbonyl]benzyl, or
11) quinolin-8-ylmethyl;
R$^{12}$ and R$^{14}$ are each independently H or CH$_3$.

7. A compound according to claim 6, or a pharmaceutically acceptable salt thereof, wherein
R$^1$ is NR$^2$R$^5$;
R$^2$ is CH$_3$;
R$^5$ is
1) C(O)CH$_2$SO$_2$CH$_3$,
2) C(O)C(O)N(CH$_3$)$_2$,
3) SO$_2$N(CH$_3$)$_2$, or
4) SO$_2$R$^{20}$, wherein R$^{20}$ is:

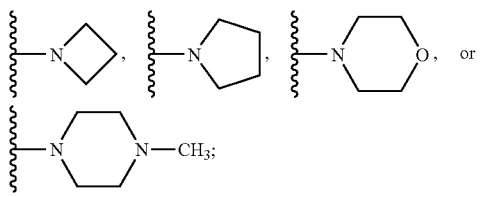

or alternatively $R^2$ and $R^5$ together with the nitrogen atom to which they are attached form

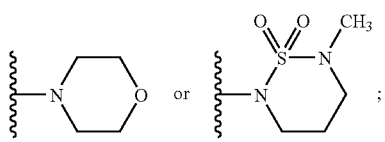

$R^4$ is:
1) p-fluorobenzyl,
2) 4-fluoro-3-methylbenzyl,
3) 3-chlorobenzyl, or
4) 3-chloro-4-methylbenzyl;

$R^{12}$ and $R^{14}$ are both H, except that when $R^5$ is $C(O)C(O)N(CH_3)_2$ and $R^4$ is p-fluorobenzyl, then $R^{12}$ and $R^{14}$ are either both H or both $CH_3$.

8. A compound according to claim 7, or a pharmaceutically acceptable salt thereof, wherein $R^5$ is $C(O)C(O)N(CH_3)_2$, or $SO_2R^{20}$, wherein $R^{20}$ is

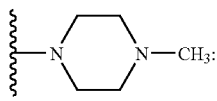

$R^4$ is p-fluorobenzyl or 4-fluoro-3-methylbenzyl;

$R^{12}$ and $R^{14}$ are both H, except that when $R^5$ is $C(O)C(O)N(CH_3)_2$ and $R^4$ is p-fluorobenzyl, then $R^{12}$ and $R^{14}$ are either both H or both $CH_3$.

9. A compound according to claim 4, or a pharmaceutically acceptable salt thereof, which is a compound of formula:

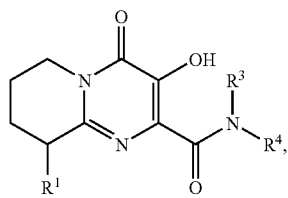

wherein $R^1$ is hydrogen, $NR^2R^5$, $OR^2$, $SR^2$, $SOR^2$, $SO_2R^2$, $SO_2NR^2R^5$, or $OC(O)NR^2R^5$;

$R^3$ is hydrogen;

$R^4$ is

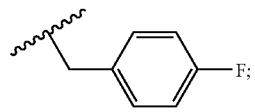

$R^2$ is
1) hydrogen,
2) $CH_3$, or
3)

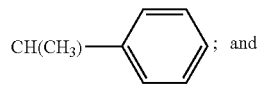
; and $R^5$ is
1) $C(O)CH_3$,
2) $C(O)CH_2SO_2CH_3$,
3) $CH_3$,
4) $C(O)C(O)N(CH_3)_2$,
5) $SO_2CH_3$,
6) $SO_2N(CH_3)_2$,
7) $C(O)CH_2N(CH_3)_2$,
8) $SO_2CH_2SO_2CH_3$,
9) $C(O)CF_3$,
10)

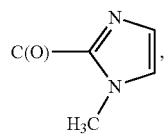

11)

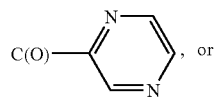
, or

12)

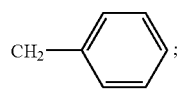
;

or $R^2$ and $R^5$, together with the nitrogen atom to which they are attached, form a heterocyclic ring selected from the group consisting of

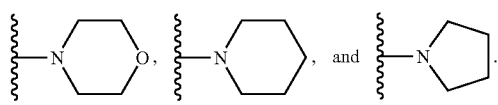

10. A compound according to claim 1, or a pharmaceutically acceptable salt thereof, selected from the group consisting of:

N-(4-fluorobenzyl)-3-hydroxy-4-oxo-6,7,8,9-tetrahydro-4H-pyrido[1,2-a]pyrimidine-2-carboxamide;

9-[acetyl(methyl)amino]-N-(4-fluorobenzyl)-3-hydroxy-4-oxo-6,7,8,9-tetrahydro-4H-pyrido[1,2-a]pyrimidine-2-carboxamide;

N-(4-fluorobenzyl)-3-hydroxy-9-{methyl[(1-methyl-1H-imidazol-2-yl)carbonyl]amino}-4-oxo-6,7,8,9-tetrahydro-4H-pyrido[1,2-a]pyrimidine-2-carboxamide;

N-(4-fluorobenzyl)-3-hydroxy-9-{methyl[(methylsulfonyl)acetyl]amino}-4-oxo-6,7,8,9-tetrahydro-4H-pyrido[1,2-a]pyrimidine-2-carboxamide;

N-(4-fluorobenzyl)-3-hydroxy-9-[methyl(pyrazin-2-ylcarbonyl)amino]-4-oxo-6,7,8,9-tetrahydro-4H-pyrido[1,2-a]pyrimidine-2-carboxamide;

9-[benzyl(methyl)amino]-N-(4-fluorobenzyl)-3-hydroxy-4-oxo-6,7,8,9-tetrahydro-4H-pyrido[1,2-a]pyrimidine-2-carboxamide;

N-(4-fluorobenzyl)-3-hydroxy-9-morpholin-4-yl-4-oxo-6,7,8,9-tetrahydro-4H-pyrido[1,2-a]pyrimidine-2-carboxamide;

N-(4-fluorobenzyl)-3-hydroxy-4-oxo-9-piperidin-1-yl-6,7,8,9-tetrahydro-4H-pyrido[1,2-a]pyrimidine-2-carboxamide;

9-(dimethylamino)-N-(4-fluorobenzyl)-3-hydroxy-4-oxo-6,7,8,9-tetrahydro-4H-pyrido[1,2-a]pyrimidine-2-carboxamide;

N-(4-fluorobenzyl)-3-hydroxy-4-oxo-9-pyrrolidin-1-yl-6,7,8,9-tetrahydro-4H-pyrido[1,2-a]pyrimidine-2-carboxamide;

N1-(2-{[(4-fluorobenzyl)amino]carbonyl}-3-hydroxy-4-oxo-6,7,8,9-tetrahydro-4H-pyrido[1,2-a]pyrimidin-9-yl)-N1,N2,N2-trimethylethanediamide;

N-(4-fluorobenzyl)-3-hydroxy-9-[methyl(methylsulfonyl)amino]-4-oxo-6,7,8,9-tetrahydro-4H-pyrido[1,2-a]pyrimidine-2-carboxamide;

9-[[(dimethylamino)sulfonyl](methyl)amino]-N-(4-fluorobenzyl)-3-hydroxy-4-oxo-6,7,8,9-tetrahydro-4H-pyrido[1,2-a]pyrimidine-2-carboxamide;

N-(4-fluorobenzyl)-3-hydroxy-9-{[(methylsulfonyl)acetyl]amino}-4-oxo-6,7,8,9-tetrahydro-4H-pyrido[1,2-a]pyrimidine-2-carboxamide;

9-[(N,N-dimethylglycyl)(methyl)amino]-N-(4-fluorobenzyl)-3-hydroxy-4-oxo-6,7,8,9-tetrahydro-4H-pyrido[1,2-a]pyrimidine-2-carboxamide;

N-(4-fluorobenzyl)-3-hydroxy-9-(methyl{[(methylsulfonyl)methyl]sulfonyl}amino)-4-oxo-6,7,8,9-tetrahydro-4H-pyrido[1,2-a]pyrimidine-2-carboxamide;

(+)-9-[[(dimethylamino)sulfonyl](methyl)amino]-N-(4-fluorobenzyl)-3-hydroxy-4-oxo-6,7,8,9-tetrahydro-4H-pyrido[1,2-a]pyrimidine-2-carboxamide;

(−)-9-[[(dimethylamino)sulfonyl](methyl)amino]-N-(4-fluorobenzyl)-3-hydroxy-4-oxo-6,7,8,9-tetrahydro-4H-pyrido[1,2-a]pyrimidine-2-carboxamide;

(−)N1-(2-{[(4-fluorobenzyl)amino]carbonyl}-3-hydroxy-4-oxo-6,7,8,9-tetrahydro-4H-pyrido[1,2-a]pyrimidin-9-yl)-N1,N2,N2-trimethylethanediamide;

(+)N1-(2-{[(4-fluorobenzyl)amino]carbonyl}-3-hydroxy-4-oxo-6,7,8,9-tetrahydro-4H-pyrido[1,2-a]pyrimidin-9-yl)-N1,N2,N2-trimethylethanediamide;

(+)—N-(4-fluorobenzyl)-3-hydroxy-4-oxo-9-[[(1S)-1-phenylethyl](trifluoroacetyl)-amino]-6,7,8,9-tetrahydro-4H-pyrido[1,2-a]pyrimidine-2-carboxamide;

(−)—N-(4-fluorobenzyl)-3-hydroxy-4-oxo-9-[[(1S)-1-phenylethyl](trifluoroacetyl)-amino]-6,7,8,9-tetrahydro-4H-pyrido[1,2-a]pyrimidine-2-carboxamide;

N-(4-fluorobenzyl)-3-hydroxy-4-oxo-4,6,7,8-tetrahydropyrrolo[1,2-a]pyrimidine-2-carboxamide;

N-(3-bromo-4-fluorobenzyl)-9-[[(dimethylamino)sulfonyl](methyl)amino]-3-hydroxy-4-oxo-6,7,8,9-tetrahydro-4H-pyrido[1,2-a]pyrimidine-2-carboxamide;

N-(4-fluorobenzyl)-3-hydroxy-9-{methyl[(1,3,5-trimethyl-1H-pyrazol-4-yl)sulfonyl]amino}-4-oxo-6,7,8,9-tetrahydro-4H-pyrido[1,2-a]pyrimidine-2-carboxamide;

9-[{[(dimethylamino)sulfonyl]acetyl}(methyl)amino]-N-(4-fluorobenzyl)-3-hydroxy-4-oxo-6,7,8,9-tetrahydro-4H-pyrido[1,2-a]pyrimidine-2-carboxamide;

9-{ethyl [(methylsulfonyl)acetyl]amino}-N-(4-fluorobenzyl)-3-hydroxy-4-oxo-6,7,8,9-tetrahydro-4H-pyrido[1,2-a]pyrimidine-2-carboxamide;

9-(1,1-dioxido-1,2-thiazinan-2-yl)-N-(4-fluorobenzyl)-3-hydroxy-4-oxo-6,7,8,9-tetrahydro-4H-pyrido[1,2-a]pyrimidine-2-carboxamide;

N-(3,4-difluorobenzyl)-3-hydroxy-9-{methyl[(methylsulfonyl)acetyl]amino}-4-oxo-6,7,8,9-tetrahydro-4H-pyrido[1,2-a]pyrimidine-2-carboxamide;

9-[[(dimethylamino)sulfonyl](ethyl)amino]-N-(4-fluorobenzyl)-3-hydroxy-4-oxo-6,7,8,9-tetrahydro-4H-pyrido[1,2-a]pyrimidine-2-carboxamide;

(+)—N-(4-fluorobenzyl)-3-hydroxy-9-{methyl[(methylsulfonyl)acetyl]amino}-4-oxo-6,7,8,9-tetrahydro-4H-pyrido[1,2-a]pyrimidine-2-carboxamide;

(−)—N-(4-fluorobenzyl)-3-hydroxy-9-{methyl[(methylsulfonyl)acetyl]amino}-4-oxo-6,7,8,9-tetrahydro-4H-pyrido[1,2-a]pyrimidine-2-carboxamide;

N-(2-{[(4-fluoro-3-methylbenzyl)amino]carbonyl}-3-hydroxy-4-oxo-6,7,8,9-tetrahydro-4H-pyrido[1,2-a]pyrimidin-9-yl)-N,N',N'-trimethylethanediamide;

N-(2-{[(3-chloro-4-methylbenzyl)amino]carbonyl}-3-hydroxy-4-oxo-6,7,8,9-tetrahydro-4H-pyrido[1,2-a]pyrimidin-9-yl)-N,N',N'-trimethylethanediamide;

N-(2-{[(3-chlorobenzyl)amino]carbonyl}-3-hydroxy-4-oxo-6,7,8,9-tetrahydro-4H-pyrido[1,2-a]pyrimidin-9-yl)-N,N',N'-trimethylethanediamide;

N-(4-fluorobenzyl)-3-hydroxy-9-(6-methyl-1,1-dioxido-1,2,6-thiadiazinan-2-yl)-4-oxo-6,7,8,9-tetrahydro-4H-pyrido[1,2-a]pyrimidine-2-carboxamide;

(−)—N-(2-{[(4-fluoro-3-methylbenzyl)amino]carbonyl}-3-hydroxy-4-oxo-6,7,8,9-tetrahydro-4H-pyrido[1,2-a]pyrimidin-9-yl)-N,N',N'-trimethylethanediamide;

(−)—N-(2-{[(3-chloro-4-methylbenzyl)amino]carbonyl}-3-hydroxy-4-oxo-6,7,8,9-tetrahydro-4H-pyrido[1,2-a]pyrimidin-9-yl)-N,N',N'-trimethylethanediamide;

(+)—N-(4-fluorobenzyl)-3-hydroxy-9-(6-methyl-1,1-dioxido-1,2,6-thiadiazinan-2-yl)-4-oxo-6,7,8,9-tetrahydro-4H-pyrido[1,2-a]pyrimidine-2-carboxamide;

N-(4-fluorobenzyl)-3-hydroxy-9-[methyl(pyrrolidin-1-ylsulfonyl)amino]-4-oxo-6,7,8,9-tetrahydro-4H-pyrido[1,2-a]pyrimidine-2-carboxamide;

9-[(azetidin-1-ylsulfonyl)(methyl)amino]-N-(4-fluorobenzyl)-3-hydroxy-4-oxo-6,7,8,9-tetrahydro-4H-pyrido[1,2-a]pyrimidine-2-carboxamide;

(−)—N-(4-fluorobenzyl)-3-hydroxy-9-[methyl(morpholin-4-ylsulfonyl)amino]-4-oxo-6,7,8,9-tetrahydro-4H-pyrido[1,2-a]pyrimidine-2-carboxamide;

(+)—N-(4-fluorobenzyl)-3-hydroxy-9-[methyl(morpholin-4-ylsulfonyl)amino]-4-oxo-6,7,8,9-tetrahydro-4H-pyrido[1,2-a]pyrimidine-2-carboxamide;

N-(2-{[(3-bromo-4-fluorobenzyl)amino]carbonyl}-3-hydroxy-4-oxo-6,7,8,9-tetrahydro-4H-pyrido[1,2-a]pyrimidin-9-yl)-N,N',N'-trimethylethanediamide;

9-[[azetidin-1-yl(oxo)acetyl](methyl)amino]-N-(4-fluorobenzyl)-3-hydroxy-4-oxo-6,7,8,9-tetrahydro-4H-pyrido[1,2-a]pyrimidine-2-carboxamide;

(+)-9-[(azetidin-1-ylsulfonyl)(methyl)amino]-N-(4-fluorobenzyl)-3-hydroxy-4-oxo-6,7,8,9-tetrahydro-4H-pyrido[1,2-a]pyrimidine-2-carboxamide;

(−)—N-(2-{[(3-chloro-4-fluorobenzyl)amino]carbonyl}-3-hydroxy-4-oxo-6,7,8,9-tetrahydro-4H-pyrido[1,2-a]pyrimidin-9-yl)-N,N',N'-trimethylethanediamide;

(+)—N-(4-fluoro-3-methylbenzyl)-3-hydroxy-9-[methyl(morpholin-4-ylsulfonyl)amino]-4-oxo-6,7,8,9-tetrahydro-4H-pyrido[1,2-a]pyrimidine-2-carboxamide;

(−)-9-[{[(dimethylamino)sulfonyl]acetyl}(methyl)amino]-N-(4-fluoro-3-methylbenzyl)-3-hydroxy-4-oxo-6,7,8,9-tetrahydro-4H-pyrido[1,2-a]pyrimidine-2-carboxamide;

(−)—N-(4-fluorobenzyl)-3-hydroxy-9-{methyl[(4-methylpiperazin-1-yl)sulfonyl]amino}-4-oxo-6,7,8,9-tetrahydro-4H-pyrido[1,2-a]pyrimidine-2-carboxamide;

(+)—N-(4-fluorobenzyl)-3-hydroxy-9-{methyl[(4-methylpiperazin-1-yl)sulfonyl]amino}-4-oxo-6,7,8,9-tetrahydro-4H-pyrido[1,2-a]pyrimidine-2-carboxamide;

N-(4-fluorobenzyl)-3-hydroxy-9-{methyl[(4-methylpiperazin-1-yl)sulfonyl]amino}-4-oxo-6,7,8,9-tetrahydro-4H-pyrido[1,2-a]pyrimidine-2-carboxamide;

(−)-(7S)-7-amino-N-(4-fluorobenzyl)-3-hydroxy-4-oxo-6,7,8,9-tetrahydro-4H-pyrido[1,2-a]pyrimidine-2-carboxamide;

N-(2-{[(4-fluorobenzyl)amino]carbonyl}-3-hydroxy-8,8-dimethyl-4-oxo-6,7,8,9-tetrahydro-4H-pyrido[1,2-a]pyrimidin-9-yl)-N,N',N'-trimethylethanediamide;

N-(4-fluorobenzyl)-3-hydroxy-9-[methyl([1,2,4]triazolo[1,5-a]pyrimidin-2-ylcarbonyl)amino]-4-oxo-6,7,8,9-tetrahydro-4H-pyrido[1,2-a]pyrimidine-2-carboxamide;

N-(4-fluorobenzyl)-3-hydroxy-9-{methyl[(1-methyl-1H-imidazol-4-yl)sulfonyl]amino}-4-oxo-6,7,8,9-tetrahydro-4H-pyrido[1,2-a]pyrimidine-2-carboxamide;

9-[[(dimethylamino)sulfonyl](methyl)amino]-N-{4-fluoro-2-[(methylamino)carbonyl]benzyl}-3-hydroxy-4-oxo-6,7,8,9-tetrahydro-4H-pyrido[1,2-a]pyrimidine-2-carboxamide;

N-(4-fluorobenzyl)-3-hydroxy-9-{methyl[(5-methyl-1,3,4-oxadiazol-2-yl)carbonyl]amino}-4-oxo-6,7,8,9-tetrahydro-4H-pyrido[1,2-a]pyrimidine-2-carboxamide;

9-{[2-(dimethylamino)-2-oxoethyl]thio}-N-(4-fluorobenzyl)-3-hydroxy-4-oxo-6,7,8,9-tetrahydro-4H-pyrido[1,2-a]pyrimidine-2-carboxamide;

9-[[(dimethylamino)carbonyl](methyl)amino]-N-(4-fluorobenzyl)-3-hydroxy-4-oxo-6,7,8,9-tetrahydro-4H-pyrido[1,2-a]pyrimidine-2-carboxamide;

9-{[2-(dimethylamino)-2-oxoethyl]sulfonyl}-N-(4-fluorobenzyl)-3-hydroxy-4-oxo-6,7,8,9-tetrahydro-4H-pyrido[1,2-a]pyrimidine-2-carboxamide;

N-(4-fluorobenzyl)-3-hydroxy-9-{methyl[(1-oxidopyridin-2-yl)carbonyl]amino}-4-oxo-6,7,8,9-tetrahydro-4H-pyrido[1,2-a]pyrimidine-2-carboxamide;

methyl (2-{[(4-fluorobenzyl)amino]carbonyl}-3-hydroxy-4-oxo-6,7,8,9-tetrahydro-4H-pyrido[1,2-a]pyrimidin-9-yl)methylcarbamate N-(4-fluorobenzyl)-3-hydroxy-9-{methyl[(morpholin-4-ylsulfonyl)acetyl]amino}-4-oxo-6,7,8,9-tetrahydro-4H-pyrido[1,2-a]pyrimidine-2-carboxamide;

N-(cyclopropylmethyl)-N-(2-{[(4-fluorobenzyl)amino]carbonyl}-3-hydroxy-4-oxo-6,7,8,9-tetrahydro-4H-pyrido[1,2-a]pyrimidin-9-yl)-N',N'-dimethylethanediamide;

9-[{2-[(dimethylamino)sulfonyl]-2-methylpropanoyl}(methyl)amino]-N-(4-fluorobenzyl)-3-hydroxy-4-oxo-6,7,8,9-tetrahydro-4H-pyrido[1,2-a]pyrimidine-2-carboxamide;

9-[{[(dimethylamino)sulfonyl]acetyl}(methyl)amino]-3-hydroxy-4-oxo-N-(quinolin-8-ylmethyl)-6,7,8,9-tetrahydro-4H-pyrido[1,2-a]pyrimidine-2-carboxamide;

N-(3-hydroxy-2-{[(3-methylbenzyl)amino]carbonyl}-4-oxo-6,7,8,9-tetrahydro-4H-pyrido[1,2-a]pyrimidin-9-yl)-N,N',N'-trimethylethanediamide;

N-(2-{[(3,4-difluorobenzyl)amino]carbonyl}-3-hydroxy-4-oxo-6,7,8,9-tetrahydro-4H-pyrido[1,2-a]pyrimidin-9-yl)-N,N',N'-trimethylethanediamide;

N-(2-{[(4-fluorobenzyl)amino]carbonyl}-3-hydroxy-4-oxo-6,7,8,9-tetrahydro-4H-pyrido[1,2-a]pyrimidin-9-yl)-N',N'-dimethyl-N-(pyridin-2-ylmethyl)ethanediamide;

9-{(dimethylaminocarbonylmethyl)[(dimethylamino)sulfonyl]amino}-N-(4-fluorobenzyl)-3-hydroxy-4-oxo-6,7,8,9-tetrahydro-4H-pyrido[1,2-a]pyrimidine-2-carboxamide;

9{(4-morpholinylcarbonylmethyl)(dimethylamino)sulfonyl]amino}-N-(4-fluorobenzyl)-3-hydroxy-4-oxo-6,7,8,9-tetrahydro-4H-pyrido[1,2-a]pyrimidine-2-carboxamide;

(+)—N-(2-{[(4-fluoro-3-methylbenzyl)amino]carbonyl}-3-hydroxy-4-oxo-6,7,8,9-tetrahydro-4H-pyrido[1,2-a]pyrimidin-9-yl)-N,N',N'-trimethylethanediamide;

N-(2-{[(3-chloro-4-fluorobenzyl)amino]carbonyl}-3-hydroxy-4-oxo-6,7,8,9-tetrahydro-4H-pyrido[1,2-a]pyrimidin-9-yl)-N,N',N'-trimethylethanediamide;

(−) N-(2-{[(4-chlorobenzyl)amino]carbonyl}-3-hydroxy-4-oxo-6,7,8,9-tetrahydro-4H-pyrido[1,2-a]pyrimidin-9-yl)-N,N',N'-trimethylethanediamide;

(−)-(7S)-7-[acetyl(methyl)amino]-N-(4-fluorobenzyl)-3-hydroxy-4-oxo-6,7,8,9-tetrahydro-4H-pyrido[1,2-a]pyrimidine-2-carboxamide;

8-(dimethylamino)-N-(4-fluorobenzyl)-3-hydroxy-4-oxo-6,7,8,9-tetrahydro-4H-pyrido[1,2-a]pyrimidine-2-carboxamide; and 8-[acetyl(methyl)amino]-N-(4-fluorobenzyl)-3-hydroxy-4-oxo-6,7,8,9-tetrahydro-4H-pyrido[1,2-a]pyrimidine-2-carboxamide.

11. A compound according to claim 10, or a pharmaceutically acceptable salt thereof, selected from the group consisting of:

(−)—N-(4-fluorobenzyl)-3-hydroxy-9-{methyl[(methylsulfonyl)acetyl]amino}-4-oxo-6,7,8,9-tetrahydro-4H-pyrido[1,2-a]pyrimidine-2-carboxamide;

N-(2-{[(4-fluoro-3-methylbenzyl)amino]carbonyl}-3-hydroxy-4-oxo-6,7,8,9-tetrahydro-4H-pyrido[1,2-a]pyrimidin-9-yl)-N,N',N'-trimethylethanediamide;

N-(2-{[(3-chloro-4-methylbenzyl)amino]carbonyl}-3-hydroxy-4-oxo-6,7,8,9-tetrahydro-4H-pyrido[1,2-a]pyrimidin-9-yl)-N,N',N'-trimethylethanediamide;

N-(2-{[(3-chlorobenzyl)amino]carbonyl}-3-hydroxy-4-oxo-6,7,8,9-tetrahydro-4H-pyrido[1,2-a]pyrimidin-9-yl)-N,N',N'-trimethylethanediamide;

N-(4-fluorobenzyl)-3-hydroxy-9-(6-methyl-1,1-dioxido-1,2,6-thiadiazinan-2-yl)-4-oxo-6,7,8,9-tetrahydro-4H-pyrido[1,2-a]pyrimidine-2-carboxamide;

(−)—N-(2-{[(4-fluoro-3-methylbenzyl)amino]carbonyl}-3-hydroxy-4-oxo-6,7,8,9-tetrahydro-4H-pyrido[1,2-a]pyrimidin-9-yl)-N,N',N'-trimethylethanediamide;

(+)—N-(4-fluorobenzyl)-3-hydroxy-9-(6-methyl-1,1-dioxido-1,2,6-thiadiazinan-2-yl)-4-oxo-6,7,8,9-tetrahydro-4H-pyrido[1,2-a]pyrimidine-2-carboxamide;

N-(4-fluorobenzyl)-3-hydroxy-9-[methyl(pyrrolidin-1-ylsulfonyl)amino]-4-oxo-6,7,8,9-tetrahydro-4H-pyrido[1,2-a]pyrimidine-2-carboxamide;

9-[(azetidin-1-ylsulfonyl)(methyl)amino]-N-(4-fluorobenzyl)-3-hydroxy-4-oxo-6,7,8,9-tetrahydro-4H-pyrido[1,2-a]pyrimidine-2-carboxamide;

(−)—N-(4-fluorobenzyl)-3-hydroxy-9-[methyl(morpholin-4-ylsulfonyl)amino]-4-oxo-6,7,8,9-tetrahydro-4H-pyrido[1,2-a]pyrimidine-2-carboxamide;

(+)—N-(4-fluorobenzyl)-3-hydroxy-9-[methyl(morpholin-4-ylsulfonyl)amino]-4-oxo-6,7,8,9-tetrahydro-4H-pyrido[1,2-a]pyrimidine-2-carboxamide;

(+)-9-[(azetidin-1-ylsulfonyl)(methyl)amino]-N-(4-fluorobenzyl)-3-hydroxy-4-oxo-6,7,8,9-tetrahydro-4H-pyrido[1,2-a]pyrimidine-2-carboxamide;

(−)-9-[{[(dimethylamino)sulfonyl]acetyl}(methyl)amino]-N-(4-fluoro-3-methylbenzyl)-3-hydroxy-4-oxo-6,7,8,9-tetrahydro-4H-pyrido[1,2-a]pyrimidine-2-carboxamide;

(−)—N-(4-fluorobenzyl)-3-hydroxy-9-{methyl[(4-methylpiperazin-1-yl)sulfonyl]amino}-4-oxo-6,7,8,9-tetrahydro-4H-pyrido[1,2-a]pyrimidine-2-carboxamide;

(+)—N-(4-fluorobenzyl)-3-hydroxy-9-{methyl[(4-methylpiperazin-1-yl)sulfonyl]amino}-4-oxo-6,7,8,9-tetrahydro-4H-pyrido[1,2-a]pyrimidine-2-carboxamide;

N-(4-fluorobenzyl)-3-hydroxy-9-{methyl[(4-methylpiperazin-1-yl)sulfonyl]amino}-4-oxo-6,7,8,9-tetrahydro-4H-pyrido[1,2-a]pyrimidine-2-carboxamide; and N-(2-{[(4-fluorobenzyl)amino]carbonyl}-3-hydroxy-8,8-dimethyl-4-oxo-6,7,8,9-tetrahydro-4H-pyrido[1,2-a]pyrimidin-9-yl)-N,N',N'-trimethylethanediamide.

12. A pharmaceutical composition comprising a therapeutically effective amount of a compound according to claim 1, or a pharmaceutically acceptable salt thereof, and a pharmaceutically acceptable carrier.

13. A combination comprising therapeutically effective amount of a compound according to claim 1, or a pharmaceutically acceptable salt thereof, and a therapeutically effective amount of an antiviral selected from the group consisting of HIV protease inhibitors, non-nucleoside HIV reverse transcriptase inhibitors and nucleoside HIV reverse transcriptase inhibitors.

14. A method for treating infection by HIV or for treating AIDS in a subject in need thereof which comprises administering to the subject an effective amount of a compound according to claim 1, or a pharmaceutically acceptable salt thereof.

* * * * *